US010984915B2

(12) United States Patent
Ito et al.

(10) Patent No.: US 10,984,915 B2
(45) Date of Patent: Apr. 20, 2021

(54) MEDICAL/CARE SUPPORT METHOD, MEDICAL/CARE SUPPORT SYSTEM, AND MEDICAL/CARE SUPPORT PROGRAM

(71) Applicant: Embrace Co., Ltd., Tokyo (JP)

(72) Inventors: Manabu Ito, Tokyo (JP); Yasuko Sagasaki, Tokyo (JP); Yoshihiro Ogura, Tokyo (JP)

(73) Assignee: EMBRACE CO., LTD., Tokyo (JP)

( * ) Notice: Subject to any disclaimer, the term of this patent is extended or adjusted under 35 U.S.C. 154(b) by 0 days.

(21) Appl. No.: 14/895,394

(22) PCT Filed: Jun. 3, 2014

(86) PCT No.: PCT/JP2014/064754
§ 371 (c)(1),
(2) Date: Dec. 2, 2015

(87) PCT Pub. No.: WO2014/196535
PCT Pub. Date: Dec. 11, 2014

(65) Prior Publication Data
US 2016/0117464 A1    Apr. 28, 2016

(30) Foreign Application Priority Data

Jun. 3, 2013    (JP) .............................. JP2013-117415
Jul. 18, 2013    (JP) .............................. JP2013-149980

(51) Int. Cl.
*G16H 80/00*      (2018.01)
*G16H 10/60*      (2018.01)
(Continued)

(52) U.S. Cl.
CPC ............. *G16H 80/00* (2018.01); *G16H 10/60* (2018.01); *G16H 40/20* (2018.01); *G16H 40/67* (2018.01); *G16H 15/00* (2018.01)

(58) Field of Classification Search
CPC ........ G06Q 50/24; G16H 10/60; G16H 40/20; G16H 80/00
See application file for complete search history.

(56) References Cited

U.S. PATENT DOCUMENTS

2001/0026377 A1*   10/2001   Ikegami ................ G06T 1/0021
                                                                           358/401
2002/0099568 A1*   7/2002   Turner ................... G06Q 10/10
                                                                             705/2

(Continued)

FOREIGN PATENT DOCUMENTS

JP      2008-140174 A      6/2008
JP      4658225 B2      3/2011
KR     10-1192330 B1      10/2012

OTHER PUBLICATIONS

Extended (Supplementary) Search Report dated Dec. 15, 2016, issued in counterpart European Application No. 14807166.5 (9 pages).

(Continued)

*Primary Examiner* — Jonathan Durant
(74) *Attorney, Agent, or Firm* — Westerman, Hattori, Daniels & Adrian, LLP

(57) ABSTRACT

A medical/care support method is provided, which enables medical or care workers having different special fields such as physicians and nurses to share the medical or care information of each patient or care-needing person while protecting the privacy of the patient or care-needing person, and to support the provision of better-quality medical or care service to the patient or care-needing person based on the medical or care information shared. A patient ID, a disease ID, and a medical facility ID are associated and stored, thereby generating a group G11. A patient P1 designated by patient group registration participates in the group G11 after the patient's approval of an invitation request. Medical (Continued)

workers M1 and M2 and patient-related persons R1, R2, and R4 participate in the group G11 as supporters in response to respective invitation requests.

24 Claims, 41 Drawing Sheets

(51) Int. Cl.
*G16H 40/20* (2018.01)
*G16H 40/67* (2018.01)
*G16H 15/00* (2018.01)

(56) References Cited

U.S. PATENT DOCUMENTS

| | | | |
|---|---|---|---|
| 2007/0019616 A1* | 1/2007 | Rantapuska | H04L 12/1822 370/352 |
| 2011/0093281 A1* | 4/2011 | Plummer | G06F 19/363 705/2 |
| 2011/0125844 A1* | 5/2011 | Collier | H04L 12/00 709/204 |
| 2012/0066140 A1* | 3/2012 | Hegeman | G06Q 10/10 705/319 |
| 2012/0331567 A1 | 12/2012 | Shelton | |
| 2013/0035946 A1* | 2/2013 | Ratan | G06F 19/3418 705/2 |

OTHER PUBLICATIONS

International Search Report dated Oct. 21, 2014, issued in counterpart application No. PCT/JP2014/064754 (2 pages).
Office Action dated Mar. 21, 2018, issued in counterpart Korean Application No. 10-2015-7037265, with English translation. (15 pages).
EIR tow a?, [online], EIR Inc., Apr. 7, 2013, Internet <URL:https://web.archive.org/web/20130407041623/http://www.eir-note.com/index.html>.
Riyosha Toroku, [online], EIR Inc., Apr. 7, 2013, Internet <URL:https://web.archive.org/web/20130407041415/http://www.eir-note.com/features_a_users_html>.
Kanja Toroku, [online], EIR Inc., Apr. 7, 2013, Internet <URL:https://web.archive.org/web/20130407042740/http://www.eir-note.com/features_patient.html>.
Shisetsukan Renkei Toroku, [ online] , EIR Inc., Apr. 7, 2013, Internet <URL:https://web.archive.org/web/20130407043336/http://www.eir-note.com/features_a_relation_html>.
International Preliminary Report on Patentability dated Dec. 8, 2015, issued in counterpart application No. PCT/JP2014/064754.

* cited by examiner

FIG. 4A

USER TABLE

| USER ID | LOGIN ID | PW | REG. DATE | STATUS |
|---|---|---|---|---|
| 100 | sumida@test.com | tKswU8yq | 2012/12/10 | effective |
| 200 | nozaki@test.com | fvXEd5Re | 2012/11/20 | effective |
| 300 | yamada@test.com | acD1V5tp | 2012/12/25 | effective |

FIG. 4B

PATIENT TABLE

| PATIENT ID | USER ID | NAME | GENDER | BIRTHDATE | E-MAIL | ADDRESS | TEL |
|---|---|---|---|---|---|---|---|
| 1 | 100 | Hisae SUMIDA | female | 1945/7/18 | sumida@test.com | 1-2-3 Chuo-cho, Meguro-ku | 03-1234-5678 |

FIG. 4C

MEDICAL WORKER TABLE

| WORKER ID | USER ID | FACILITY ID | NAME | GENDER | BIRTHDATE | OCCUPATION |
|---|---|---|---|---|---|---|
| 1 | 200 | 1000 | Taro NOZAKI | male | 1963/8/5 | physician |

FIG. 4D

MEDICAL FACILITY TABLE

| FACILITY ID | NAME | TYPE | TREATMENT SUBJECT | ADDRESS | TEL | HP | CONSUL. HOUR | STATION |
|---|---|---|---|---|---|---|---|---|
| 1000 | Nozaki Clinic | medical clinic | Internal, Surgery, Psychosomatic, Psychiatry | 1-2-3, Monzennakacho, Koto-ku | 03-2345-6789 | http://www.nozaki-hp.xxx | Weekday: 10-18 Closed: Sun, Hol | Monzen-nakacho |

FIG. 5A

MEDICAL FACILITY PATIENT TABLE

| FAC PATIENT ID | FAC ID | PAT ID | APPROVAL | PAT NO. | NAME | GENDER | BIRTHDATE |
|---|---|---|---|---|---|---|---|
| 101 | 1000 | 1 | Yes | 123 | Hisae SUMIDA | female | 1945/7/18 |

| INSURANCE | FINAL CHECK-UP | ADDRESS | TEL | E-MAIL | PASSCODE |
|---|---|---|---|---|---|
| National Health | 2012/12/25 | 1-2-3, Chuo-cho, Meguro-ku | 03-1234-5678 | sumida@test.com | srXjR7L2dBmnwO2psAyte |

FIG. 5B

DISEASE TABLE

| DISEASE ID | FACILITY PATIENT ID | DISEASE NAME |
|---|---|---|
| 1 | 101 | Alzheimer |

FIG. 5C

GROUP TABLE

| GROUP ID | GROUP NAME | DISEASE ID |
|---|---|---|
| 10001 | Alzheimer treatment | 1 |

FIG. 5D

GROUP PARTICIPATION TABLE

| GROUP PART ID | USER ID | GROUP ID | ACCESIBLE TIMELINE |
|---|---|---|---|
| 1 | 100 | 10001 | C2 |
| 2 | 200 | 10001 | C1,C2 |

FIG. 6A

INVITATION REQUEST TABLE

| INV. REQUEST ID | SOURCE USER ID | DESTINATION USER ID | APPROVAL | PERMISSION |
|---|---|---|---|---|
| 1 | 200 | 201 | approved | permitted |

FIG. 6B

| DESTINATION E-MAIL | PASSPHRASE | GROUP ID | ACCESSIBLE TIMELINE |
|---|---|---|---|
| yamanaka@test.com | Nickmane is racoon dog | 10001 | C1,C2 |

FIG. 6C

TIMELINE TABLE

| TIMELINE ID | GROUP ID | TYPE NAME |
|---|---|---|
| 1 | 10001 | M. WORKER SIDE |
| 2 | 10001 | PATIENT SIDE |

MEDICAL INFORMATION SHARING RULE TABLE

| USER ID | FACILITY ID | SHARING RULE NAME |
|---|---|---|
| 100 | 1000 | In Facility |
| 100 | 1001 | Comprehensively |

FIG. 6D

NFC TERMINAL TABLE

| FACILITY ID | TERMINAL NO. | FAC. PATIENT ID | PASSCODE |
|---|---|---|---|
| 1000 | 3079372621 | 101 | srXjR7L2dBmnwO2psAyte |
| 1001 | 2850365002 | 102 | TixIR5Bv3EIshei8Wegkese |

FIG. 7A

MESSAGE TRANSMISSION RESERVATION TABLE

| RESERV ID | DESTINATION USER ID | SOURCE USER ID | MESSAGE | SCHEDULED DATE |
|---|---|---|---|---|
| 1 | 200 | 100 | 3 days passed from drug prescription. Do you take it as instructed? | 2012/12/29 |

FIG. 7B

PATIENT ATTRIBUTE TABLE

| ATTR ID | PATIENT ID | ATTR NAME | VALUE |
|---|---|---|---|
| 1 | 101 | medical examination guide in 2013 | Yet |

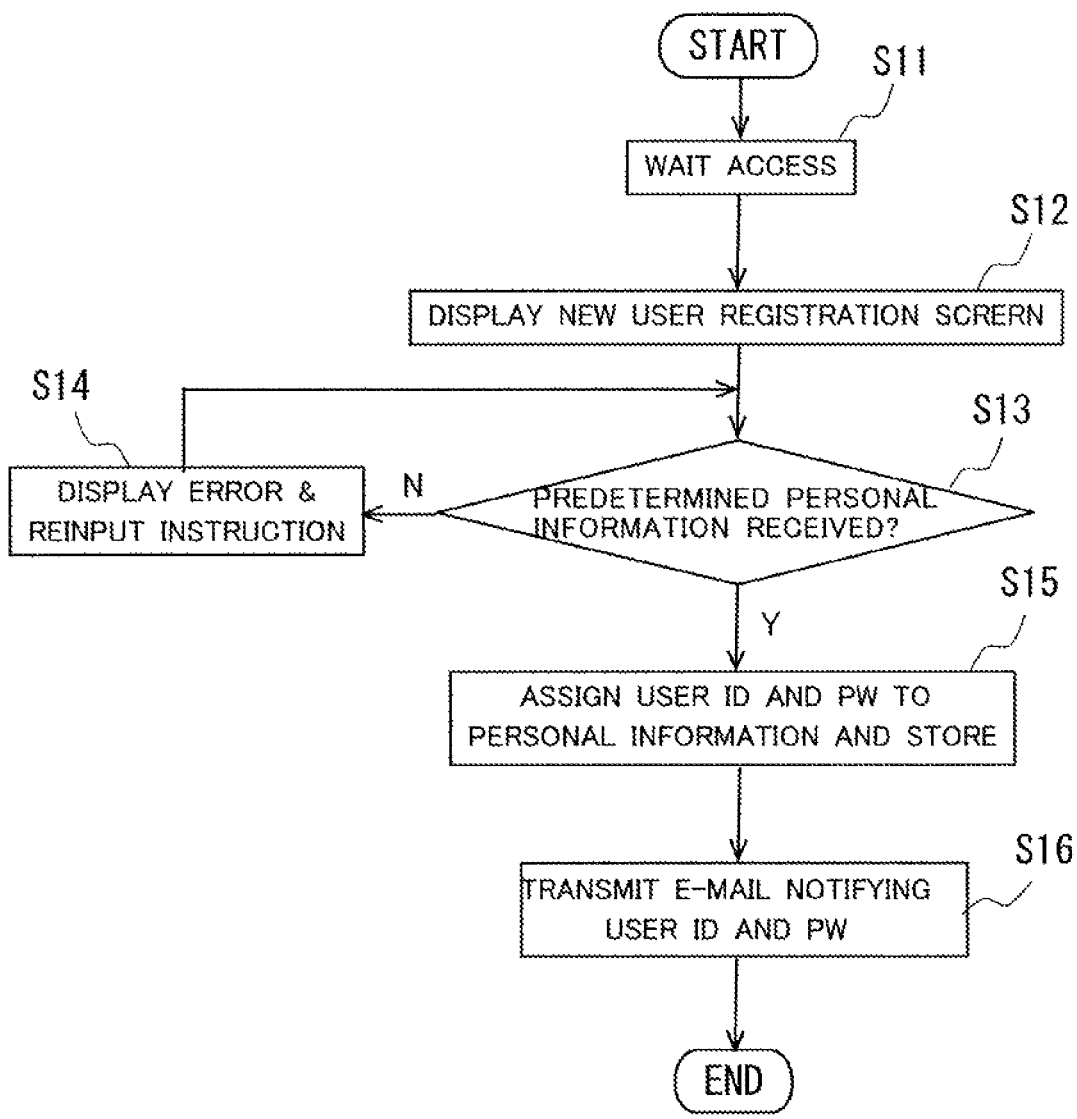

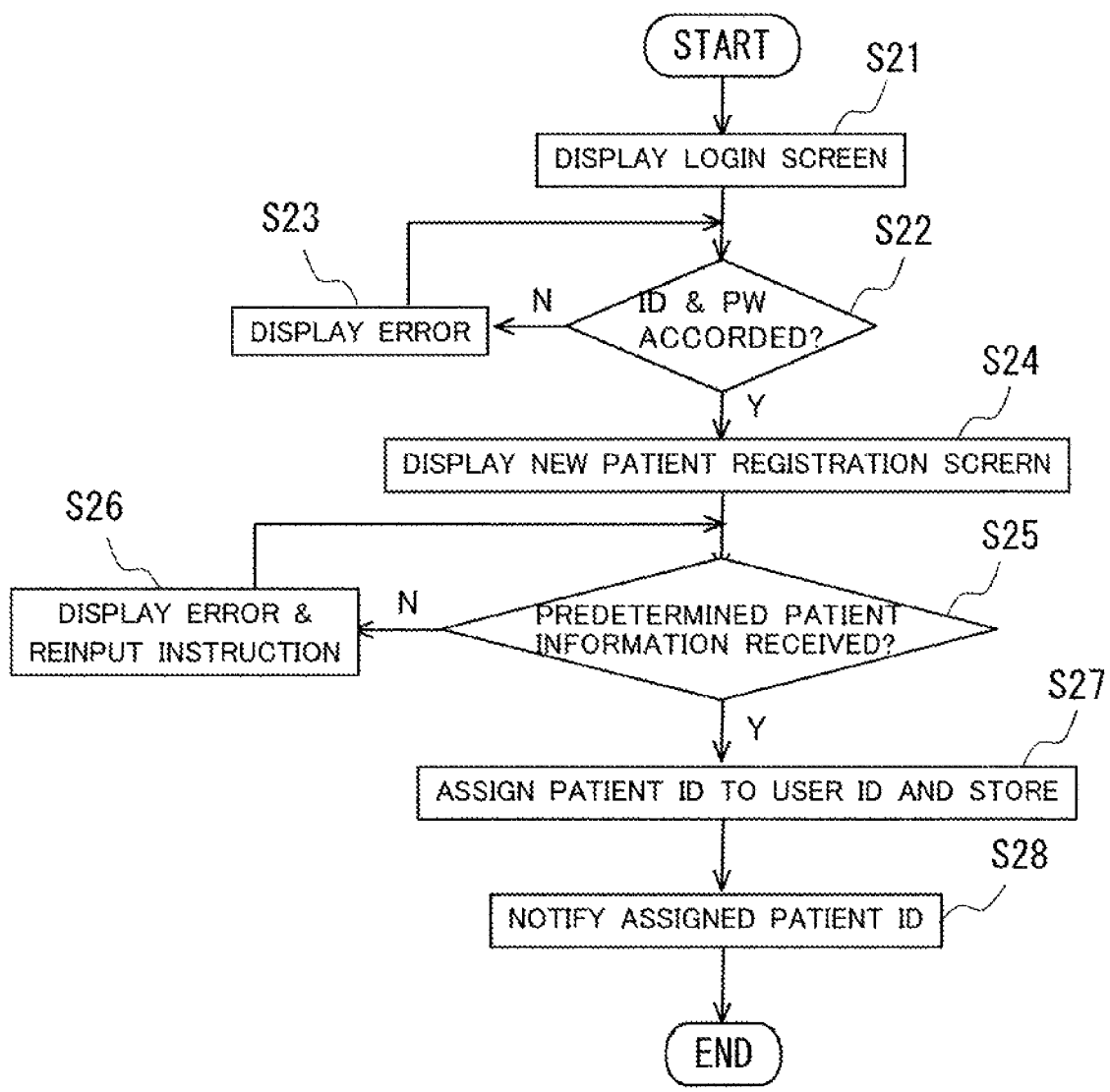

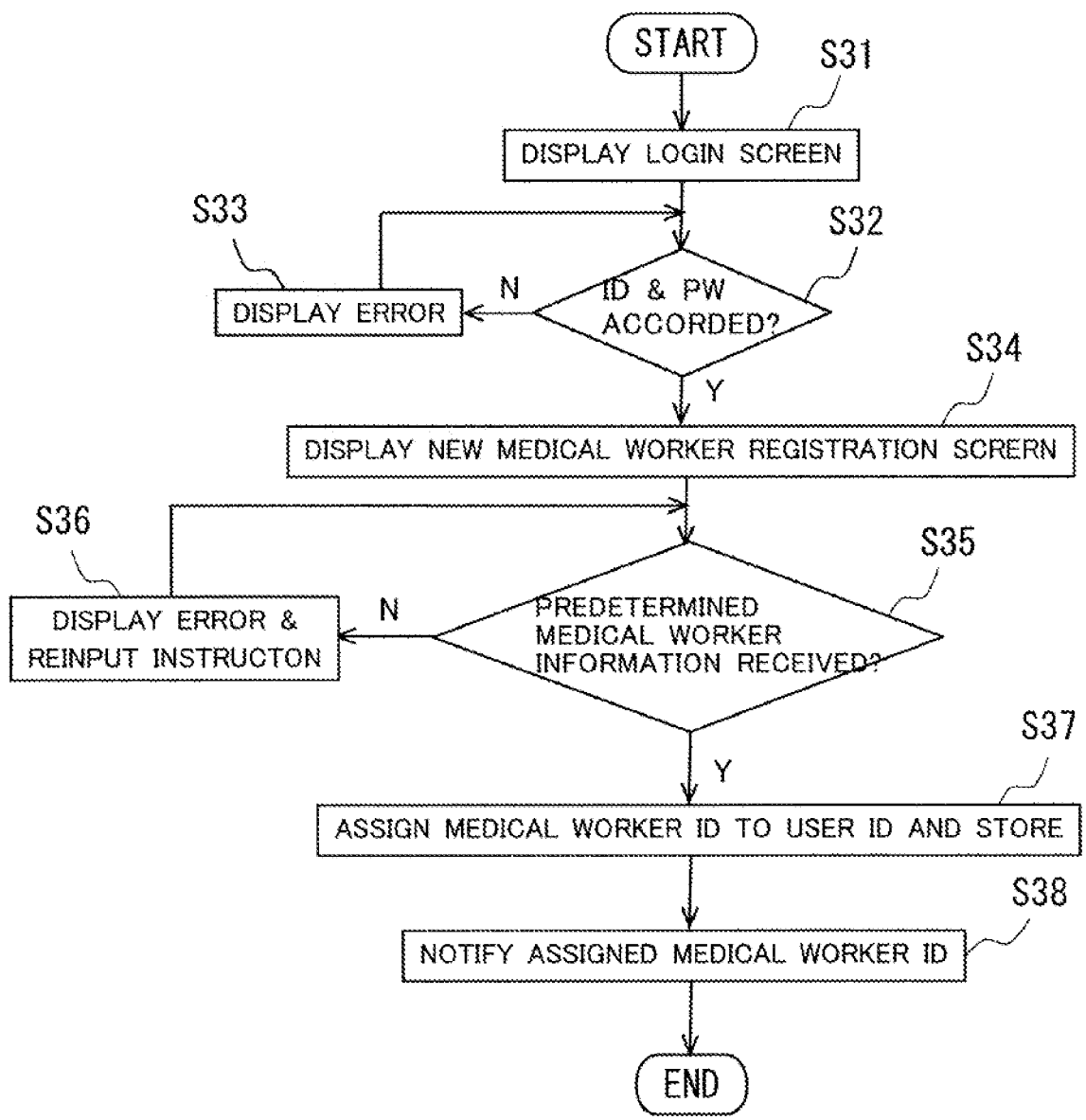

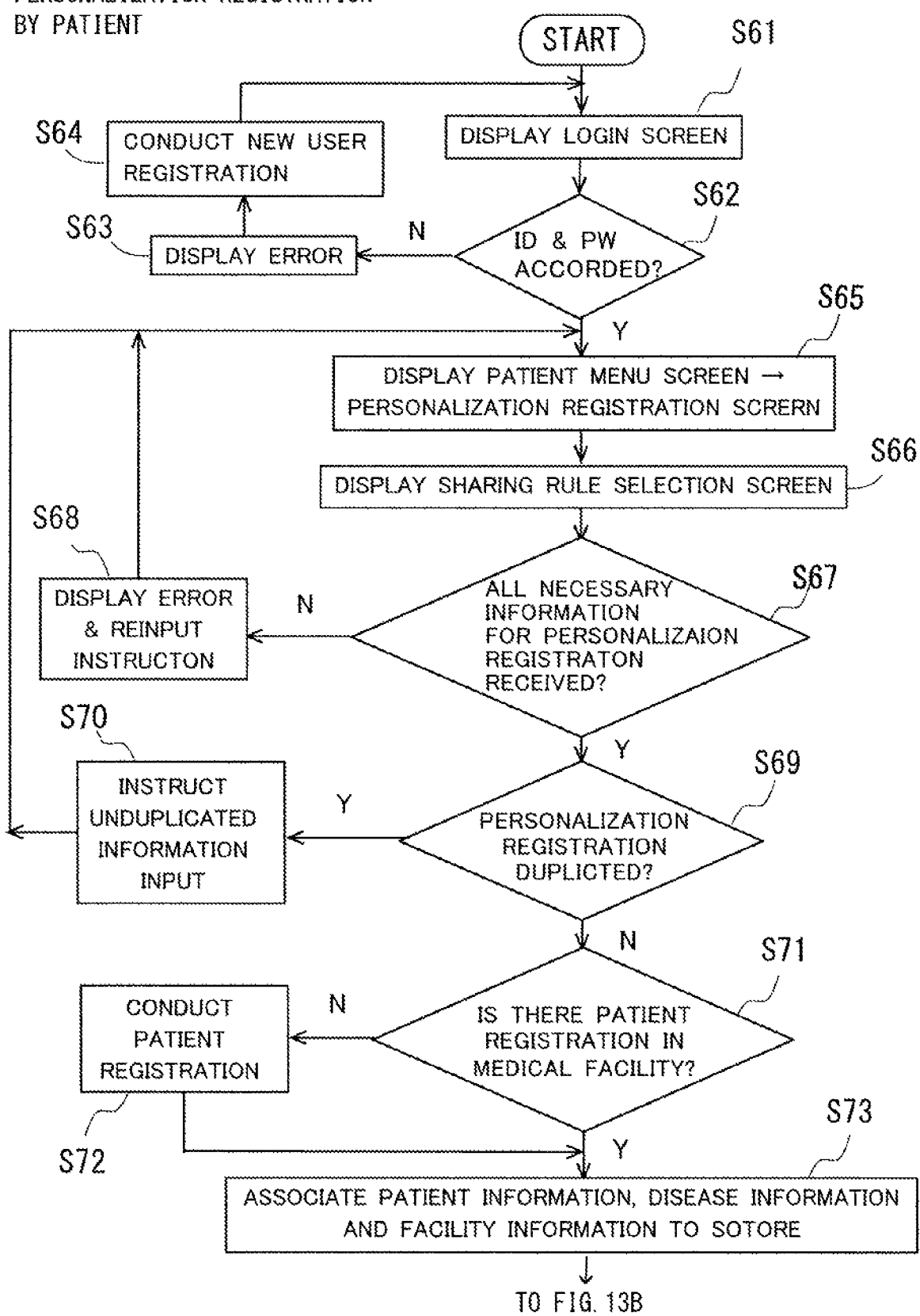

OPERATION FLOW OF
PERSONALIZATION REGISTRATION
BY PATIENT (CONTINUED)

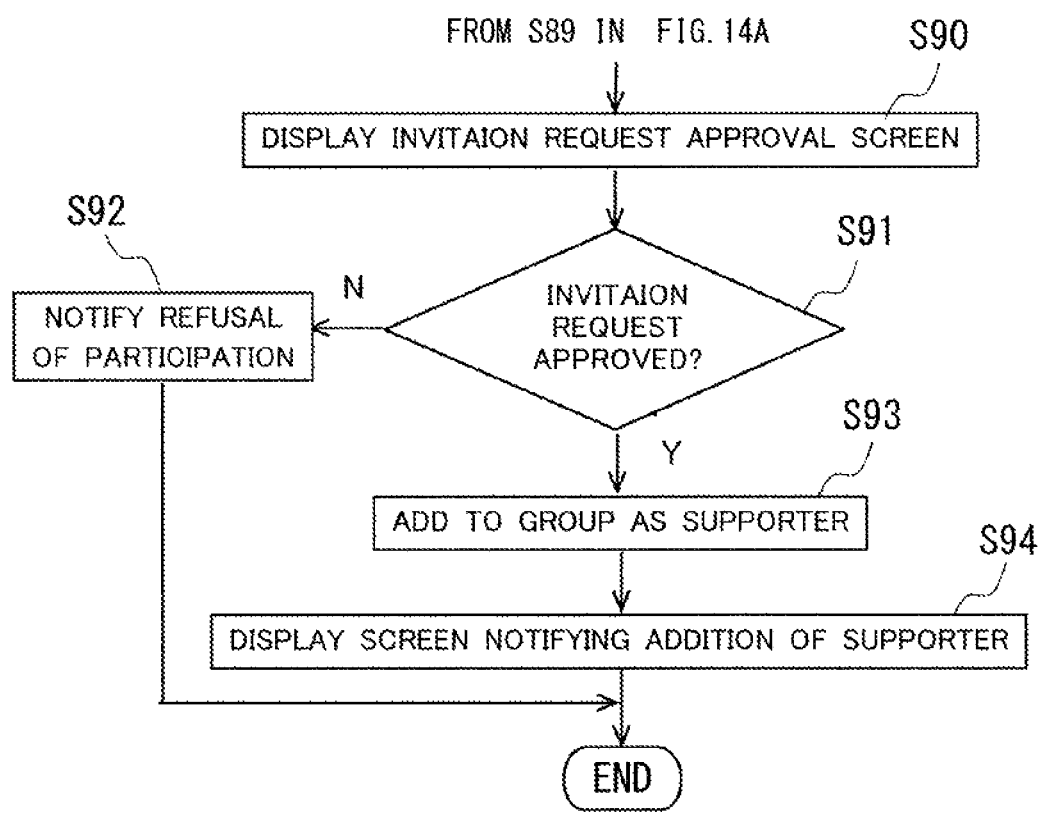

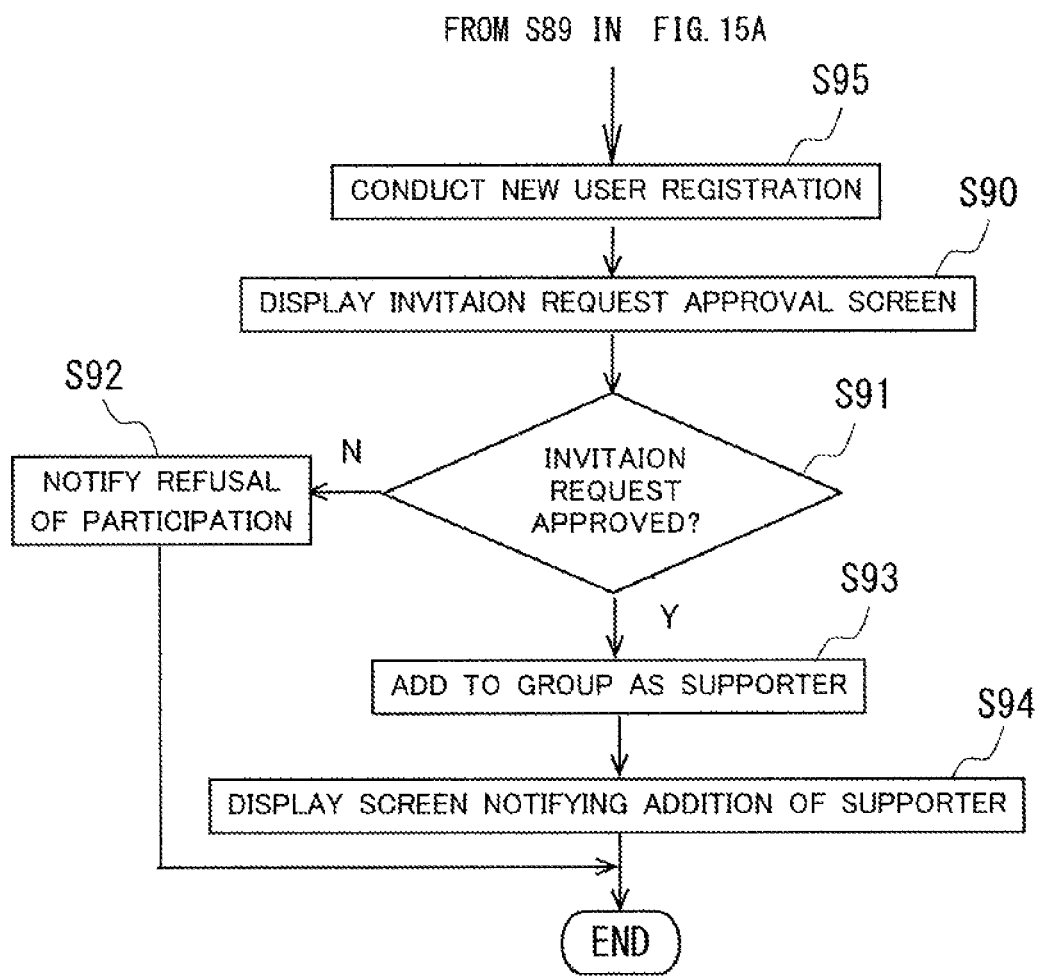

FIG. 16A

NEW USER REGISTRATION SCREEN

NEW USER REGISTRATION

YOU WILL BE REGISTERED IN MEDICAL SUPPORT SYSTEM AS A NEW USER. PLEASE SELECT REGISTRATION TYPE, INPUT THR FOLLOWING, AND CLICK TRANSMIT BUTTON.

YOUR NAME [          ]
E-MAIL ADERESS [          ]
TYPE    ⊙ PATIENT    ○ MEDICAL WORKER

[ TRANSMIT ]

FIG. 16B

LOGIN SCREEN

LOGIN

YOU WILL LOGIN MEDICAL SUPPORT SYSTEM.
PLEASE INPUT YOUR USER ID AND PASSWORD AND CLICK TRANSMIT BUTTON.

USER ID

PASSWORD

TRANSMIT

FIG. 17A

NEW PATIENT REGISTRATION SCREEN

---

NEW PATIENT REGISTRATION

YOU WILL BE REGISTERED IN MEDICAL SUPPORT SYSTEM AS A NEW PATIENT.
PLEASE INPUT THE FOLLOWING AND CLICK TRANSMIT BUTTON.

| | |
|---|---|
| NAME | Hisae SUMIDA |
| ADDRESS | |
| GENDER | ○ MALE　⦿ FEMALE |
| BIRTHDATE | |
| TELEPHONE | |
| E-MAIL | |

[ TRANSMIT ]

FIG. 17B

NEW MEDICAL WORKER REGISTRATION SCREEN

NEW MEDICAL WORKER REGISTRATION

YOU WILL BE REGISTERED IN MEDICAL SUPPORT SYSTEM AS A NEW MEDICAL WORKER.
PLEASE INPUT THE FOLLOWING AND CLICK TRANSMIT BUTTON.

| Field | Value |
|---|---|
| NAME | Taro NOZAKI |
| GENDER | ● MALE   ○ FEMALE |
| BIRTHDATE | |
| OCCUPATION | ● PHYSICIAN   ○ NURSE   ○ OTHER |
| FACILITY NAME | |
| FACILITY TYPE | |
| TREATMENT SUBJECT | |
| FACILITY ADDRESS | |
| TELEPHONE | |
| HOME PAGE | |
| CONSULTATION HOUR | |
| NEAREST STATION | |

TRANSMIT

FIG. 18

PERSONALIZATION REGISTRATION REQUEST SCREEN
UESD FOR REQUEST BY MEDICAL WORKER

---

PERSONALIZATION REGISTRATION REQUEST

PLEASE INPUT E-MAIL ADDRESS OF A PATIENT TO WHOM "NOZAKI CLINIC" IS REGISTERED AS HIS/HER PERSONALIZED MEDICAL FACIILITY, AND CLICK TRANSMIT BUTTON.

E-MAIL ADDRESS  _____

[ TRANSMIT ]

FIG. 19

APPROVAL SCREEN FOR PERSONALIZATION REGISTRATION
REQUEST BY MEDICAL WORKER

---

APPROVAL FOR PERSONALIZATION REGISTRATION

YOU HAVE BEEN REQUESTED TO REGISTER NOZAKI CLINIC AS YOUR PERSONALIZED FACLITY FOR DIABETES.
PLEASE INPUT YOUR PASSCODE AND SELECT DESIRED INFORMATION SHARING RULE; THEN, CLICK "APPROVE REGISTRATION" OR "REFUSE REGISTRATION" BUTTON

PASSCODE

INFORMATION SHARING RULE

- Rule 1 (Share in Facility)
- Rule 2 (Share complehensively)
- Rule 3 (Refuse share)

APPROVE REGISTER    REFUSE REGISTER

FIG. 20

PERSONALIZATION REGISTRATION REQUEST SCREEN
UESD FOR REQUEST BY PATIENT

PERSONALIZATION REGISTRATION REQUEST

PLEASE RETRIEVE MEDICAL FACILITY YOU WANTS TO CONDUCTE PERSONALIZATION REGISTRATION.

| INPUT KEYWORD | Retrieve |

TRANSMIT

FIG. 21

RETRIEVAL RESULT SCREEN OF MEDICAL FACILITY USED
FOR REQUEST BY PATIENT

| RETRIEVAL RESULT |
|---|
| FOLLOWING MEDICAL FACILITIES WERE FOUND. PLEASE SELECT A FACILITY YOU WANT TO REGISTER AND CLICK "PERSONALIZATION REGISTRATEION" BUTTON. |

| NOZAKI Clinic<br>1-2-3, Monzen-nakacho,<br>Koto-ku, Tokyo | Personalization<br>Registrattion |
|---|---|
| YAMADA CLINIC<br>4-5-6, Takaban, Meguro-ku,<br>Tokyo | Personalization<br>Registrattion |

FIG. 22

CONFIRMATION SCREEN FOR PERSONALIZATION
REGISTRATION REQUEST BY PATIENT

---

CONFIRMATION FOR PERSONALIZATION REGISTRATION

NOZAKI CLINIC WILL BE REGISTERED AS YOUR PERSONALIZED
FACLITY FOR DIABETES.
PLEASE INPUT YOUR PASSCODE AND SELECT DESIRED INFORMATION
SHARING RULE; THEN, CLICK "REGISTER" BUTTON

PASSCODE

INFORMATION SHARING RULE
- Rule 1 (Share in Facility)
- Rule 2 (Share comprehensively)
- Rule 3 (Refuse share)

[REGISTER]   [CANCEL]

FIG. 23
SUPPORTER INVITATION SCREEN TO EXISTING USER
INVITATION TO GROUP (DIABETES) OF Ms. Hisae SUMIDA IN NOZKI CLINIC
PLEASE SELECT SUPPORTERS TO BE INVITED FROM THE LIST BELOW.
| | | |
|---|---|---|
| 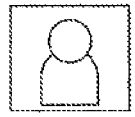 | Hanako YAMADA | Invite |
| 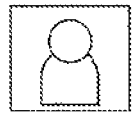 | Ichiro SUZUKI | Invite |
| 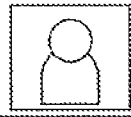 | Jiro SATO | Invite |
| 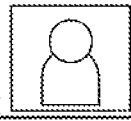 | Michiko NAKAMURA | Invite |

FIG. 24

SUPPORTER INVITATION PERMISSION SCREEN TO EXISTING USER

---

INVITATION TO GROUP (DIABETES) OF Ms. Hisae SUMIDA IN NOZKI CLINIC

Ms. Hanako YAMADA AND Mr. ichiro SUZUKI ARE BEING INVITED AS SUPPORTERS TO THE GROUP (DIABETES) OF Ms. Hisae SUMIDA IN NOZAKI CLINIC.
DO YOU PERMIT THIS INVITATION?

| PERMIT | REFUSE |

SUPPORTER INVITATION APPROVAL SCREEN FOR EXISTING USER

FIG. 26

SUPPORTER INVITATION SCREEN TO NON-USER

INVITATION TO GROUP (DIABETES) OF Ms. Hisae SUMIDA IN NOZKI CLINIC

PLEASE INPUT E-MAIL ADRESS AND PASSPHRASE OF A PERSON YOU WANT TO INVITE AS A SUPPORTER, AND CLICK "INVITE" BUTTON.

E-MAIL ADDRESS
PASSPHRASE (*)PASSPHRASE IS USED AS PASSWORD FOR PERSONAL IDENTIFICATION. THIS PASSPHRASE WILL NOT BE EXPOSED TO THAT PERSON.

INVITE

FIG. 27

SUPPORTER INVITATION APPROVAL SCREEN FOR NON-USER

INVITATION TO GROUP (DIABETES) OF Ms. Hisae SUMIDA IN NOZKI CLINIC HAS REACHED.

YOU ARE BEING INVITED AS A SUPPORTER TO THE GROUP (DIABETES) OF Ms. Hisae SUMIDA IN NOZAKI CLINIC.
DO YOU PARTICIPATE?
IF YOU PARTICIPATE, USER REGISTRATION IS NEEDED IN ADVANCE; PLEASE INPUT THE FOLLOWING AND CLICK "TRANSMIT" BUTTON.

E-MAIL ADDRESS
PASSPHRASE

TRANSMIT

FIG. 28

SUPPORTER INVITATION PERMISSION SCREEN TO NON-USER

INVITATION TO GROUP (DIABETES) OF Ms. Hisae SUMIDA IN NOZKI CLINIC

Ms. Yoko YAMAMOTO IS BEING INVITED AS A SUPPORTER TO THE GROUP (DIABETES) OF Ms. Hisae SUMIDA IN NOZAKI CLINIC.
DO YOU PERMIT THIS INVITATION?

| PERMIT | REFUSE |

FIG. 33

INTEGRATED MEDICAL INFORMATION OF Mr. A

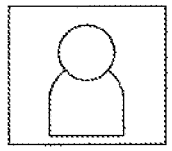

Mr. A
AGE: 83

MEDICAL INFORMATION IN CLINIC X
NAME: A          BIRTHDATE: 1930/10/10
DISEASE NAME: DIABETES
NOTE: FIRST VISIT IN OCTOBER 2012; STAY WITH HIS SON AND YOUNGER BROTHER; LETTER OF INTRODUCTION FROM DOC. XX IN HOSPITAL XXX

| TO PHYSICIAN-SIDE TIMELINE | TO PATIENT-SIDE TIMELINE |

MEDICAL INFORMATION IN CLINIC Y
NAME: A          BIRTHDATE: 1930/10/10
DISEASE NAME: LUNG CANCER
NOTE: MEDICAL HISTORY, ASTHMA, DIABETES; NEEDED CARE LEVEL 3; NAUSEA & VOMITING; NOW SYMPTOMS OF DIGESTIVE ORGANS REDUCED, TAKING MEALS BY HIMSELF

| TO PHYSICIAN-SIDE TIMELINE | TO PATIENT-SIDE TIMELINE |

FIG. 34

PATIENT GROUP REGISTRATION SCREEN

| PATIENT GROUP REGISTRATION |
|---|
| A PATIENT WILL BE REGISTERED IN MEDICAL SUPPORT SYSTEM.<br>PLEASE INPUT PATIENT'S NAME AND HIS/HER DISEASE NAME, AND CLICK TRANSMIT BUTTON.<br><br>PATIENT'S NAME [                ]<br>DISEASE NAME [                ]<br><br>[ TRANSMIT ] |

MEDICAL/CARE SUPPORT METHOD, MEDICAL/CARE SUPPORT SYSTEM, AND MEDICAL/CARE SUPPORT PROGRAM

TECHNICAL FIELD

The present invention relates to a medical/care support method, a medical/care support system, and a medical/care support program and more particularly, to a medical/care support method, a medical/care support system, and a medical/care support program that make it possible to view and inputting/outputting medical information and/or care information about individual patients or care-needing persons and to send/receive messages using user terminals by way of a network, thereby supporting the provision of good-quality medical service or care service through the cooperation of medical workers and/or care workers who belong to various occupation categories, such as physicians, nurses, nutritionists, and care managers whose special fields are different from each other.

BACKGROUND ART

In recent years, due to the declining birthrate and aging population, the number of people (medical service users) who utilize a variety of medical services in medical facilities (e.g., hospitals, clinics, home-visit nursing stations) in the same time period has kept increasing. Medical services are provided by specialists such as physicians, nurses, dentists, dental hygienists and so on (which will be termed "medical specialists" hereinafter) who have different special fields, such as internal medicine, surgery, orthopedic surgery, otolaryngology, ophthalmology, and dentistry and thus, many specialists who belong to multiple occupation categories are involved in medical services. Moreover, it is often that medical services which belong to different special fields are provided in medical facilities which are located at different positions. Therefore, currently, medical information about individual medical service users (i.e., patients) are independently stored and utilized in the respective medical facilities which are located at different positions without relevance.

Incidentally, it is much preferred if a patient can utilize the result of diagnosis, treatment, examination, and/or operation for a specific disease which he or she has already undergone in a medical facility, when the same patient undergoes diagnosis, treatment, examination, and/or operation for the same disease or a different one in a different medical facility later. This is because the medical specialists have an advantage that the diagnostic accuracy and curative effects are raised due to the increased medical information which is available to diagnosis and/or treatment, and because the patient has an advantage that the expenses and labor on attending medical facilities are saved due to cancellation of duplicated diagnosis, treatment, and/or examination. In addition, the government also has an advantage that the medical expenses which the government pays to the medical facilities decreases.

In this way, it is highly beneficial if the situation where the medical information about each patient can be shared by medical specialists who are involved with medical treatment of the same patient in different medical facilities can be realized with an information system. However, since the medical information about each patient is personal information of the patient, it is necessary to obtain the patient's approval of sharing his/her medical information. Moreover, it is also necessary to obtain the approval of the medical specialists (physicians) who possess the medical information about each patient. Accordingly, it is necessary to incorporate the approval process of both the patient and the medical specialists into the information system.

The aforementioned circumstances are applicable to long-term care services. This is because not only care supporters (caregivers) such as care managers and helpers but also physicians and nurses may be stationed in care-related facilities, and because even if they are not stationed in care-related facilities, the care-related facilities are in cooperation with external medical facilities in such a way that medical services can be quickly received periodically or according to necessity. In this case, care-needing persons utilize medical services along with care services and thus, the medical information and the care information about the care-needing persons (who are patients also) will be shared by the medical facilities and the care-related facilities. If the aforementioned information system capable of sharing the medical information is applied to such the case, the problem about information sharing which occurs in the cooperation among the specialists belonging to multiple occupation categories, which is regarded as a challenge in home care, can be solved; this is highly effective.

As a prior art relevant to the present invention, for example, there is a care support system disclosed in Patent Literature 1. This care support system supports all groups and/or persons relevant to long-term care, such as community general support centers, caring enterprises, and the families of care-needing persons, in such a way that the groups and/or persons can share the care information and that the care-needing persons can utilize suitable care services and the care staff can provide the said care services based on the care information thus shared.

With this care service system, a user information table, a staff information table, and a long-term care insurance information table are provided; an attribute judgment section judges whether or not the information received from a user terminal or a care staff terminal is in accordance with the information included in the staff information table or the long-term care insurance information table. Then, if the information received from the user or care staff terminal is in accordance with, a registration section assigns a new user information ID to the user or care staff who has sent the information and generates a new user information table to store the said table based on the user information ID thus assigned, a user ID associated with the information which has been judged in accorded with, and the information received. If the information received from the user or care staff terminal is not in accordance with, the registration section assigns a new user information ID and a new user ID to the user or care staff who has sent the information and generates a new user information table and a new staff attribute table or a new long-term care insurance information table and stores these tables based on the user information ID and the user ID thus assigned and the information received. Subsequently, a service providing section transmits the care service information which has been requested by the user or staff terminal to the said terminal by way of a network based on the stuff information table and the long-term care insurance information table.

In this way, the care support system of Patent Literature 1 makes it possible for all the groups and/or persons relevant to long-term care such as community general support centers, caring enterprises, and the families of care-needing persons to share the "care information".

PRIOR ART LITERATURE

Patent Literature

[Patent Literature 1] Japanese Examined Patent Publication No. 4,658,225

SUMMARY OF THE INVENTION

Problems to be Resolved by the Invention

With the care service system of Patent Literature 1 having the aforementioned structure, all the groups and/or persons relevant to care such as community general support centers, caring enterprises, and the families of care-needing persons are able to share the "care information". However, this system is unable to be applied to the case where "medical information" about the disease(s) of each patient is shared among a plurality of medical facilities. The reason of this is as follows:

Specifically, first, the medical information about each patient includes a variety of information about the respective diseases which belong to different special fields and therefore, the said medical information is usually stored in a plurality of medical facilities (e.g., hospitals, clinics, home-visit nursing stations) which are located at different positions. In addition, since each of the medical facilities is unable to know whether or not a certain patient has received diagnosis or treatment in another medical facility unless the patient notifies the current medical facility that he/she has received diagnosis or treatment in a different medical facility. Accordingly, an information system for sharing the medical information stored in the medical facilities needs to have a subsystem that enables patients to apply a statement and that authenticates the identification of the applicant. Moreover, this information system needs to have a structure that enables the medical facilities to make an inquiry to the patient also. However, the care service system of Patent Literature 1 does not have such the subsystem and the structure as described here.

Furthermore, three is a case where a patient does not want to share his/her own medical information with others because he/she dislikes about his/her disease being known to others, or a case where a patient accepts the sharing of his/her own medical information with limited persons. For this reason, it is necessary for the information system to include the structure that enables the patient himself/herself to reflect his/her intention of whether or not he/she wants to have his/her medical information shared and the structure that enables the patient to reflect his/her intention of how wide the permissible range of sharing is to be defined when the patient wants to share his/her medical information. However, the care service system of Patent Literature 1 does not have such the structures as described here.

The present invention was created while taking the aforementioned circumstances into consideration. An object of the present invention is to provide a medical/care support method, a medical/care support system, and a medical/care support program that make it possible for medical workers or care workers (which may be termed "service workers" in combination later) who belong to various occupation categories such as physicians, nurses, nutritionists, and care managers whose special fields are different from each other to share the medical information or care information of each patient or care-needing person (which may be termed a "service recipient" in combination later) while protecting the privacy of the patient or care-needing person, and to support the provision of better-quality medical service or care service to the patient or care-needing person based on the medical information or care information thus shared.

Another object of the present invention is to provide a medical/care support method, a medical/care support system, and a medical/care support program that make it possible for not only medical workers but also a patient or care-needing person to make a request for sharing the medical or care information of the patient or care-needing person and that is able to easily authenticate personal identification of the patient or care-needing person who has received the request for sharing or who has made the request for sharing.

Still another object of the present invention is to provide a medical/care support method, a medical/care support system, and a medical/care support program that make it possible for a patient or care-needing person to designate the sharing range of his/her medical or care information when the said patient or care-needing person approves sharing his/her medical information or care information.

The other objects not specifically mentioned will become clear to those skilled in the art from the following description and drawings attached.

Means for Solving the Problems (1) A medical/care support method according to the first aspect of the present invention is a medical/care support method for supporting provision of medical/care service by making it possible to view medical/care information about specific patients or care-needing persons on user terminals by way of a network in response to requests from the user terminals; which comprises:

assigning user identification information to respective users utilizing the medical/care service by way of the user terminals to store the user identification information;

assigning service recipient identification information to the patients or care-needing persons as the users to store the service recipient identification information so as to be associated with the user identification information;

assigning service worker identification information to medical workers or care workers as the users to store the service worker identification information so as to be associated with the user identification information;

assigning service-related facility identification information to service-related facilities to which the medical workers or care workers belong to store the service-related facility identification information so as to be associated with the service worker identification information;

generating a group having a unique group identification information in association with the service recipient identification information; and adding, in response to sending of an invitation request which includes designation of an inviting person and an invited person and which is performed using the user terminal, the invited person as the user to the group as a group member, under a condition that the invitation request is approved by the invited person using the user terminal and that permission is obtained by a predetermined administrator using the user terminal;

wherein the medical/care information of the patient or care-needing person corresponding to the service recipient identification information pertaining to the group can be shared among the medical workers or care workers as the invited persons who have been added to the group as the group members by way of the user terminals.

With the medical/care support method according to the first aspect of the present invention, since the group having the unique group identification information is generated in association with the service recipient identification information which the patient or care-needing person as the user has, the group is generated for each of the patients or care-needing persons. Therefore, if the medical workers or care workers who provide medical service or care service to the patient or care-needing person pertaining to the group are added to the group as the group members, the medical workers or care workers thus added will be able to share the medical/care information about the patient or care-needing person pertaining to the group by way of the user terminals.

Accordingly, the medical or care information of each patient or care-needing person can be shared while protecting the privacy of the patient or care-needing person and at the same time, better-quality medical service or care service can be provided to the patient or care-needing person pertaining to the group based on the medical or care information thus shared.

Moreover, in response to sending of the invitation request which includes designation of the inviting person and the invited person and which is performed using the user terminal, the invited person as the user is added to the group as the group member under the condition that the invitation request is approved by the invited person using the user terminal and that permission is obtained by the predetermined administrator using the user terminal. Therefore, there arises no anxiety that someone is added to the group as the group member without being contrary to the intention of the invited person and/or the administrator (e.g., the director of a hospital) and there arises no problem in the medical service or care service for the patient or care-needing person due to addition of the invited person as the group member to the group.

(2) In a preferred embodiment of the medical/care support method according to the first aspect of the present invention, when a personalization registration request which has been sent by way of the user terminal is received, the service recipient identification information designated by the personalization registration request and the service-related facility identification information designated by the personalization registration request are stored so as to be associated with each other; and personalized facility information about the group corresponding to the group identification information is generated by associating the service recipient identification information designated by the personalization registration request and the service-related facility identification information designated by the personalization registration request with each other.

(3) In another preferred embodiment of the medical/care support method according to the first aspect of the present invention, a number of the groups having the same service recipient identification information is n (n is an integer equal to 2 or greater), and each of the groups is associated with a corresponding one of the service-related facility identification information, wherein the medical/care information of the n groups is viewable interactively by way of the user terminals.

(4) In still another preferred embodiment of the medical/care support method according to the first aspect of the present invention, whether or not the personalization registration request is approved is inquired to the patient or care-needing person corresponding to the service recipient identification information designated by the personalization registration request while urging selection of a sharing rule for the medical/care information of his/her own; wherein when the personalization registration request is approved by the patient or care-needing person, the sharing rule selected is stored.

(5) In a further preferred embodiment of the medical/care support method according to the first aspect of the present invention, the service recipient identification information of the group is associated with disease identification information of the patient or care-needing person corresponding to the service recipient identification information.

(6) In a further preferred embodiment of the medical/care support method according to the first aspect of the present invention, identity verification for approving the personalization registration request by the service recipient pertaining to the personalization registration request is performed using a passcode which is generated based on a service recipient number (patient number or care-needing person number) or an insured person number (health insurance number, long-term care insurance number) in the service-related facility pertaining to the personalization registration request.

(7) In a further preferred embodiment of the medical/care support method according to the first aspect of the present invention, identity verification of the user pertaining to the invitation request is performed using a telephone number or a passphrase of the user pertaining to the invitation request.

(8) In a further preferred embodiment of the medical/care support method according to the first aspect of the present invention, when the patient or care-needing person pertaining to the personalization registration request approves the personalization registration request, a short-distance wireless communication terminal in which a terminal number and URL information assigned to the service-related facility pertaining to the personalization registration request have been stored is used; wherein the URL information is transmitted to the user terminal by contacting the short-distance wireless communication terminal with the user terminal, thereby displaying a personalization registration approval screen on the user terminal.

(9) In a further preferred embodiment of the medical/care support method according to the first aspect of the present invention, the medical/care information shared among the group members who belong to the group is displayed on the user terminal as a timeline.

(10) In a further preferred embodiment of the medical/care support method according to the first aspect of the present invention, the medical/care information shared among the group members who belong to the group is displayed in such a way as to be divided into an area that allows all the group members to view the medical/care information and an area that allows only the medical workers or care workers who belong to the group to view the medical/care information.

(11) A medical/care support system according to the second aspect of the present invention is a medical/care support system for supporting provision of medical/care service by making it possible to view medical/care information about specific patients or care-needing persons on user terminals by way of a network in response to requests from the user terminals; which comprises:

user identification information storing means for assigning user identification information to respective users utilizing the medical/care service by way of the user terminals to store the user identification information;

service recipient identification information storing means for assigning service recipient identification information to the patients or care-needing persons as the users to store the service recipient identification information so as to be associated with the user identification information;

service worker identification information storing means for assigning service worker identification information to medical workers or care workers as the users to store the service worker identification information so as to be associated with the user identification information;

service-related facility identification information storing means for assigning service-related facility identification information to service-related facilities to which the medical workers or care workers belong to store the service-related facility identification information so as to be associated with the service worker identification information;

group management means for generating a group having a unique group identification information in association with the service recipient identification information; and invitation request management means for adding, in response to sending of an invitation request which includes designation of an inviting person and an invited person and which is performed using the user terminal, the invited person as the user to the group as a group member, under a condition that the invitation request is approved by the invited person using the user terminal and that permission is obtained by a predetermined administrator using the user terminal;

wherein the medical/care information of the patient or care-needing person corresponding to the service recipient identification information pertaining to the group can be shared among the medical workers or care workers as the invited persons which have been added to the group as the group members by way of the user terminals.

With the medical/care support system according to the second aspect of the present invention, since the group having the unique group identification information is generated by the group management means in association with the service recipient identification information which the patient or care-needing person as the user has, the group is generated for each of the patients or care-needing persons. Therefore, if the medical workers or care workers who provide medical service or care service to the patient or care-needing person pertaining to the group are added to the group as the group members, the medical workers or care worker thus added will be able to share the medical/care information about the patient or care-needing person pertaining to the group by way of the user terminals.

Accordingly, the medical or care information of each patient or care-needing person can be shared while protecting the privacy of the patient or care-needing person and at the same time, better-quality medical service or care service can be provided to the patient or care-needing person pertaining to the group based on the medical or care information thus shared.

Moreover, in response to sending of the invitation request which includes designation of the inviting person and the invited person and which is performed using the user terminal, the invited person as the user is added by the invitation request management means to the group as the group member under the condition that the invitation request is approved by the invited person using the user terminal and that permission is obtained by the predetermined administrator using the user terminal. Therefore, there arises no anxiety that someone is added to the group as the group member without being contrary to the intention of the invited person and/or the administrator (e.g., the director of a hospital) and there arises no problem in the medical service or care service for the patient or care-needing person due to addition of the invited person as the group member to the group.

(12) In a preferred embodiment of the medical/care support system according to the second aspect of the present invention, when a personalization registration request which has been sent by way of the user terminal is received, the service recipient identification information designated by the personalization registration request and the service-related facility identification information designated by the personalization registration request are stored so as to be associated with each other; and personalized facility information about the group corresponding to the group identification information is generated by associating the service recipient identification information designated by the personalization registration request and the service-related facility identification information designated by the personalization registration request with each other.

(13) In another preferred embodiment of the medical/care support system according to the second aspect of the present invention, a number of the groups having the same service recipient identification information is n (n is an integer equal to 2 or greater), and each of the groups is associated with a corresponding one of the service-related facility identification information, wherein the medical/care information of the n groups is viewable integratively by way of the user terminals.

(14) In still another preferred embodiment of the medical/care support system according to the second aspect of the present invention, whether or not the personalization registration request is approved is inquired to the patient or care-needing person corresponding to the service recipient identification information designated by the personalization registration request while urging selection of a sharing rule for the medical/care information of his/her own; wherein when the personalization registration request is approved by the patient or care-needing person, the sharing rule selected is stored.

(15) In a further preferred embodiment of the medical/care support system according to the second aspect of the present invention, the service recipient identification information of the group is associated with disease identification information of the patient or care-needing person corresponding to the service recipient identification information.

(16) In a further preferred embodiment of the medical/care support system according to the second aspect of the present invention, identity verification for approving the personalization registration request by the service recipient pertaining to the personalization registration request is performed using a passcode which is generated based on a service recipient number (patient number or care-needing person number) or an insured person number (health insurance number, long-term care insurance number) in the service-related facility pertaining to the personalization registration request.

(17) In a further preferred embodiment of the medical/care support system according to the second aspect of the present invention, identity verification of the user pertaining to the invitation request is performed using a telephone number or a passphrase of the user pertaining to the invitation request.

(18) In a further preferred embodiment of the medical/care support system according to the second aspect of the present invention, when the patient or care-needing person pertaining to the personalization registration request approves the personalization registration request, a short-distance wireless communication terminal in which a terminal number and URL information assigned to the service-related facility pertaining to the personalization registration request have been stored is used; wherein the URL information is transmitted to the user terminal by contacting the short-distance wireless communication terminal with the user terminal, thereby displaying a personalization registration approval screen on the user terminal.

(19) In a further preferred embodiment of the medical/care support system according to the second aspect of the present invention, the medical/care information shared among the group members who belong to the group is displayed on the user terminal as a timeline.

(20) In a further preferred embodiment of the medical/care support system according to the second aspect of the present invention, the medical/care information shared among the group members who belong to the group is displayed in such a way as to be divided into a region that allows all the group members to view the medical/care information and a region that allows only the medical workers or care workers who belong to the group to view the medical/care information.

(21) A medical/care support program according to the third aspect of the present invention is a medical/care support program for supporting provision of medical/care service by making medical/care information about specific patients or care-needing persons viewable on user terminals by way of a network in response to requests from the user terminals; which comprises processes to be executed by a computer, the processes comprises:

assigning user identification information to respective users utilizing the medical/care service by way of the user terminals to store the user identification information;

assigning service recipient identification information to the patients or care-needing persons as the users to store the service recipient identification information so as to be associated with the user identification information;

assigning service worker identification information to medical workers or care workers as the users to store the service worker identification information so as to be associated with the user identification information;

assigning service-related facility identification information to service-related facilities to which the medical workers or care workers belong to store the service-related facility identification information so as to be associated with the service worker identification information;

generating a group having a unique group identification information in association with the service recipient identification information; and adding, in response to sending of an invitation request which includes designation of an inviting person and an invited person and which is performed using the user terminal, the invited person as the user to the group as a group member, under a condition that the invitation request is approved by the invited person using the user terminal and that permission is obtained by a predetermined administrator using the user terminal;

wherein the medical/care information of the patient or care-needing person corresponding to the service recipient identification information pertaining to the group can be shared among the medical workers or care worker as the invited persons who have been added to the group as the group members by way of the user terminals.

With the medical/care support program according to the third aspect of the present invention, because of the same reason as the aforementioned medical/care support method according to the first aspect of the present invention, the medical or care information of each patient or care-needing person (i.e., service recipient) can be shared among medical workers or care workers (i.e., service workers) who belong to various occupation categories such as physicians, nurses, nutritionists, and care managers whose special fields are different from each other while protecting the privacy of the patient or care-needing person and at the same time, the provision of better-quality medical service or care service to the patient or care-needing person based on the medical or care information thus shared can be supported.

(22) In a preferred embodiment of the medical/care support program according to the third aspect of the present invention, when a personalization registration request which has been sent by way of the user terminal is received, the service recipient identification information designated by the personalization registration request and the service-related facility identification information designated by the personalization registration request are stored so as to be associated with each other; and personalized facility information about the group corresponding to the group identification information is generated by associating the service recipient identification information designated by the personalization registration request and the service-related facility identification information designated by the personalization registration request with each other.

(23) In another preferred embodiment of the medical/care support program according to the third aspect of the present invention, a number of the groups having the same service recipient identification information is n (n is an integer equal to 2 or greater), and each of the groups is associated with a corresponding one of the service-related facility identification information, wherein the medical/care information of the n groups is viewable integratively by way of the user terminals.

(24) In still another preferred embodiment of the medical/care support program according to the third aspect of the present invention, whether or not the personalization registration request is approved is inquired to the patient or care-needing person corresponding to the service recipient identification information designated by the personalization registration request while urging selection of a sharing rule for the medical/care information of his/her own; wherein when the personalization registration request is approved by the patient or care-needing person, the sharing rule selected is stored.

(25) In a further preferred embodiment of the medical/care support program according to the third aspect of the present invention, the service recipient identification information of the group is associated with disease identification information of the patient or care-needing person corresponding to the service recipient identification information.

(26) In a further preferred embodiment of the medical/care support program according to the third aspect of the present invention, identity verification for approving the personalization registration request by the service recipient pertaining to the personalization registration request is performed using a passcode which is generated based on a service recipient number (patient number or care-needing person number) or an insured person number (health insurance number, long-term care insurance number) in the service-related facility pertaining to the personalization registration request.

(27) In a further preferred embodiment of the medical/care support program according to the third aspect of the present invention, identity verification of the user pertaining to the invitation request is performed using a telephone number or a passphrase of the user pertaining to the invitation request.

(28) In a further preferred embodiment of the medical/care support program according to the third aspect of the present invention, when the patient or care-needing person pertaining to the personalization registration request approves the personalization registration request, a short-distance wireless communication terminal in which a terminal number and URL information assigned to the service-related facility pertaining to the personalization registration request have been stored is used; wherein the URL information is transmitted to the user terminal by contacting the short-distance wireless communication terminal with the user terminal, thereby displaying a personalization registration approval screen on the user terminal.

(29) In a further preferred embodiment of the medical/care support program according to the third aspect of the present invention, the medical/care information shared among the group members who belong to the group is displayed on the user terminal as a timeline.

(30) In a further preferred embodiment of the medical/care support program according to the third aspect of the present invention, the medical/care information shared among the group members who belong to the group is displayed in such a way as to be divided into a region that allows all the group members to view the medical/care information and a region that allows only the medical workers or care workers who belong to the group to view the medical/care information.

Advantageous Effects of the Invention

With the medical/care support method according to the first aspect of the present invention, the medical/care support system according to the second aspect of the present invention, and the medical/care support program according to the third aspect of the present invention, the medical or care information of each patient or care-needing person can be shared by medical or care workers who belong to various occupation categories such as physicians, nurses, nutritionists, and care managers whose special fields are different from each other while protecting the privacy of the patient or care-needing person and at the same time, the provision of better-quality medical or care service to the patient or care-needing person based on the medical or care information thus shared can be supported.

BRIEF DESCRIPTION OF THE DRAWINGS

FIGS. 4A, 4B, 4C, and 4D are diagrams showing structure examples of tables used in the medical support system according to the embodiment of the present invention; wherein FIG. 4A shows the structure of a user table, FIG. 4B shows the structure of a patient table, FIG. 4C shows the structure of a medical worker table, and FIG. 4D shows the structure of a medical facility table.

FIGS. 5A, 5B, 5C, and 5D are diagrams showing structure examples of tables used in the medical support system according to the embodiment of the present invention; wherein FIG. 5A shows the structure of a medical facility patient table, FIG. 5B shows the structure of a disease table, FIG. 5C shows the structure of a group table, and FIG. 5D shows the structure of a group participation table.

FIGS. 6A, 6B, 6C, and 6D are diagrams showing structure examples of tables used in the medical support system according to the embodiment of the present invention; wherein FIG. 6A shows the structure of an invitation request table, FIG. 6B shows the structure of a timeline table, FIG. 6C shows the structure of a medical information sharing table, and FIG. 6D shows the structure of a NFC terminal management rule table.

FIGS. 7A and 7B are diagrams showing structure examples of tables used in the medical support system according to the embodiment of the present invention; wherein FIG. 7A shows the structure of a message transmission reservation table, and FIG. 7B shows the structure of a patient attribute table.

FIG. 10 is a flowchart showing a series of actions for new user registration by an applicant for utilizing the medical support service in the medical support system according to the embodiment of the present invention.

FIG. 11A is a flowchart showing a series of actions for new patient registration by a user of the medical support service in the medical support system according to the embodiment of the present invention.

FIG. 11B is a flowchart showing a series of actions for new medical worker registration by a user of the medical support service in the medical support system according to the embodiment of the present invention.

FIG. 13A is a flowchart showing a series of actions for personalization registration by a patient in the medical support system according to the embodiment of the present invention.

FIG. 14B is a flowchart showing a series of actions for supporter invitation of the existing users by a medical worker or patient in the medical support system according to the embodiment of the present invention, which is subsequent to FIG. 14A.

FIG. 15B is a flowchart showing a series of actions for supporter invitation of non-users by a medical worker or patient in the medical support system according to the embodiment of the present invention, which is subsequent to FIG. 15A.

FIG. 16A is an explanatory diagram showing an example of a "new user registration screen" used in the medical support system according to the embodiment of the present invention.

FIG. 16B is an explanatory diagram showing an example of a "login screen" used in the medical support system according to the embodiment of the present invention.

FIG. 17A is an explanatory diagram showing an example of a "new patient registration screen" used in the medical support system according to the embodiment of the present invention.

FIG. 17B is an explanatory diagram showing an example of a "new medical worker registration screen" used in the medical support system according to the embodiment of the present invention.

FIG. 18 is an explanatory diagram showing an example of a "personalization registration request screen" in the case of a medical worker's request used in the medical support system according to the embodiment of the present invention.

FIG. 19 is an explanatory diagram showing an example of a "personalization registration approval screen" in the case of a medical worker's request used in the medical support system according to the embodiment of the present invention.

FIG. 20 is an explanatory diagram showing an example of a "personalization registration request screen" in the case of a patient's request used in the medical support system according to the embodiment of the present invention.

FIG. 21 is an explanatory diagram showing an example of a retrieval result screen of medical facilities in the case of a patient's request used in the medical support system according to the embodiment of the present invention.

FIG. 22 is an explanatory diagram showing an example of a "personalization registration confirmation screen" in the case of a patient's request used in the medical support system according to the embodiment of the present invention.

FIG. 23 is an explanatory diagram showing an example of a "supporter invitation screen" in the case of inviting an existing user used in the medical support system according to the embodiment of the present invention.

FIG. 24 is an explanatory diagram showing an example of a "supporter invitation approval/disapproval screen" in the case of inviting an existing user used in the medical support system according to the embodiment of the present invention.

FIG. 26 is an explanatory diagram showing an example of a "supporter invitation screen" in the case of inviting a non-user used in the medical support system according to the embodiment of the present invention.

FIG. 27 is an explanatory diagram showing an example of a "supporter invitation approval screen" in the case of inviting a non-user used in the medical support system according to the embodiment of the present invention.

FIG. 28 is an explanatory diagram showing an example of a "supporter invitation approval/disapproval approval" in the case of inviting a non-user used in the medical support system according to the embodiment of the present invention.

FIG. 33 is an explanatory diagram showing integrated medical information about the patient A used in the medical support system according to the embodiment of the present invention.

FIG. 34 is an explanatory diagram showing an example of a patient group registration screen used in the medical support system according to the embodiment of the present invention.

EMBODIMENTS FOR CARRYING OUT THE INVENTION

Figure 1:
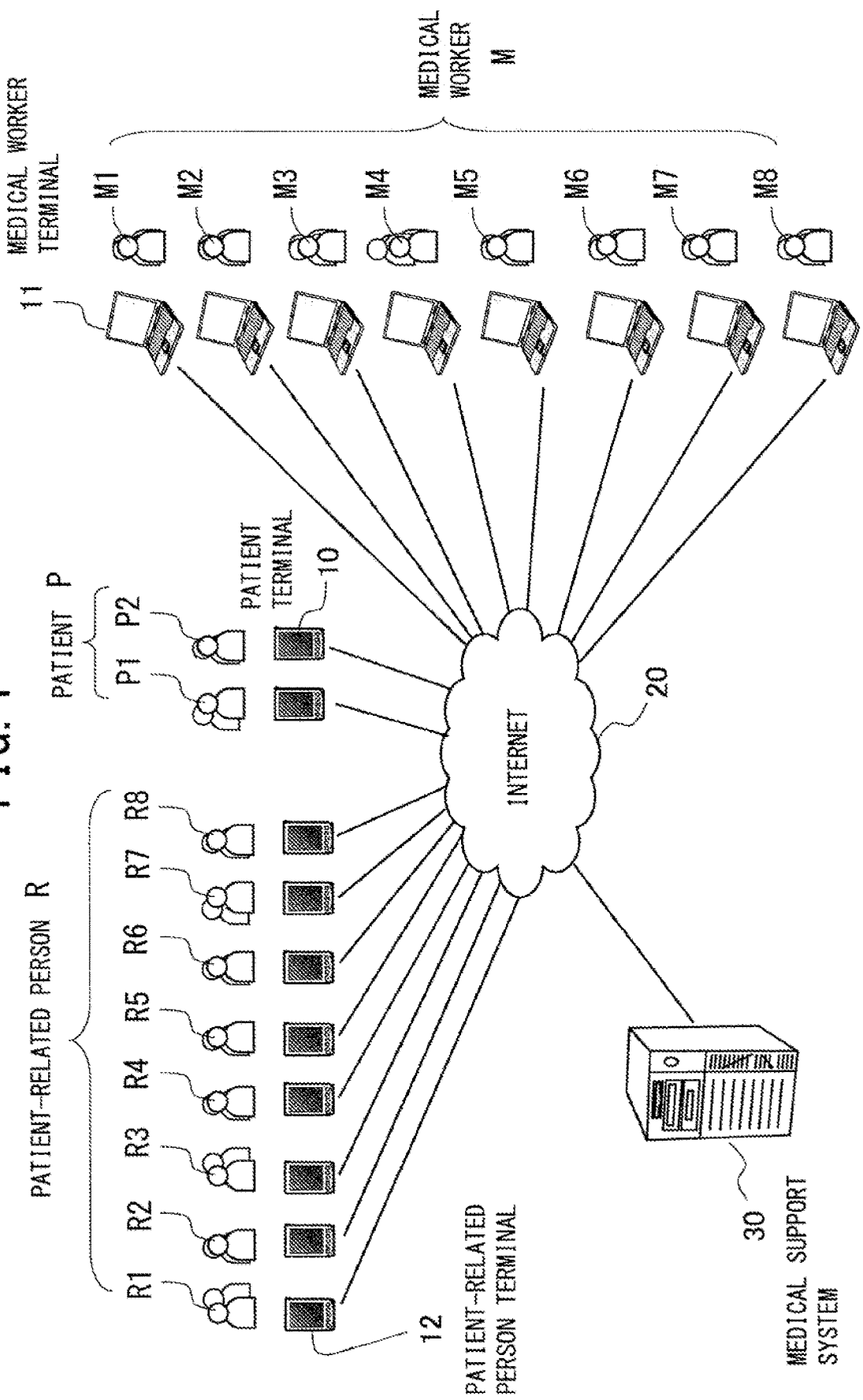
FIG. 1 is a conceptual diagram showing the state of a usage of a medical support system according to an embodiment of the present invention.

Preferred embodiments of the present invention will be described below while referring to the drawings attached.

[Utility Form of Medical Support Service]

The overall configuration of a utility form of a medical support service provided by a medical support system according to an embodiment of the present invention is shown in FIG. 1.

In the following explanation, when respective patients are discriminated, they are denoted as a "patient P1", a "patient P2", and so on, and when respective patients are not discriminated, they are denoted as "patients P". Similarly, when respective medical workers are discriminated, they are denoted as a "medical worker M1", a "medical worker M2", and so on, and when respective medical workers are not discriminated, they are denoted as "medical workers M". When respective patient-related persons are discriminated, they are denoted as a "patient-related person R1", a "patient-related person R2", and so on, and when respective patient-related persons are not discriminated, they are denoted as "patient-related persons R". When respective medical facilities are discriminated, they are denoted as a "medical facility F1", a "medical facility F2", and so on, and when respective medical facilities are not discriminated, they are denoted as "medical facilities F". When respective groups are not discriminated, they are denoted as "groups G", and when respective groups are discriminated, they are denoted as a "group G11", a "group G12", and so on.

As shown in FIG. 1, this medical support service is configured to be used by the patients P, the patient-related persons R, or the medical workers M who want to use this service from patient terminals 10 which the patients P possess, medical worker terminals 11 which the medical workers M operate, or patient-related person terminals 12 which the patient-related persons R possess (these terminals may be termed in combination "user terminals" later) by way of the Internet 20 as a communication network after they conduct their user registration in a prescribed manner.

The patients P, the patient-related persons R, or the medical workers M who have completed their user registration will be "users" of this medical support service. Since this service is realized by the medical support system 30, it may be said that the "users" of this service are the "users" of this system 30. The patients P, the patient-related persons R, or the medical workers M who have not completed their user registration are unable to use this service.

If an instruction is sent to the medical support system 30 from any one of the user terminals 10, 11 or 12 by way of the Internet 20, a variety of actions and functions such as "user registration", "group generation", "invitation to a group", "transmission/reception of messages (communication)", "personalization registration", and "viewing medical information" which will be explained later, will be carried out by the operations of the hardware and software installed into the system 30. Moreover, by doing so, the medical information and exchanged messages for each patient P can be shared among the medical workers M, or among the patient P and the medical workers M, or among the patient P, the medical workers M, and the patient-related persons R, and at the same time, better-quality medical service can be provided to each patient P based on the medical information and the messages thus shared.

The patient terminals 10 and the patient-related person terminals 12 are usually mobile terminals such as portable telephones and smartphones, and each patient P and each patient-related person R possess terminals of his/her own. However, desktop or notebook type personal computers or touch-panel type terminals may be used for this purpose. The medical worker terminals 11 are often mounted in medical facilities and thus, desktop or notebook type personal computers are usually used for this purpose; however, it is needless to say that touch-panel type terminals or mobile terminals may be used for the terminals 11. In summary, it is sufficient that these terminals 10, 11, and 12 are terminal devices which are capable of transmission, reception, and display of information to the medical support system 30 by way of the Internet 20, and the form and structure of the terminals 10, 11, and 12 do not matter.

Each patient P suffers from one or more diseases and receives medical services such as diagnosis and treatment in a specific medical facility F from the medical workers M who belong to this facility. To simplify the explanation, a case where only two patients P1 and P2 utilize this medical support service is assumed in this embodiment. However, it is needless to say that more patients P utilize this medical support service in a real world.

The patient-related person P indicates a person who has a relationship with the patient P in some form, such as a family member, relation, friend, acquaintance of each patient P. Even a medical worker M may be a patient-related person of a patient P if he/she is a family member, relation, friend, or acquaintance of the patient P. Here, a case where eight patient-related persons R1, R2, R3, R4, R5, R6, R7, and R8 have participated in is assumed. However, it is needless to say that more or less patient-related persons R utilize this medical support service according to the circumstances of the patient P in a real world.

The medical worker M indicates a person who is engaged in medical treatment in a medical facility, such as a physician and a nurse. The medical worker M belongs to a medical facility F such as a clinic (a small-sized physician's office) having a special field, a hospital (a middle- or large-sized medical facility), and a home-visit nursing station, and provides medical services such as diagnosis and treatment to his/her patients P in the facility F. Here, a case where only eight medical workers M1, M2, M3, M4, M5, M6, M7, and M8 have participated in is assumed. However, it is needless to say that more or less medical workers M participate in a real world.

The medical facility F indicates a facility in which medical service is provided to the patients P by the medical workers M, for example, a small-sized physician's office (a clinic), a hospital having a larger scale than the clinic, and a home-visit nursing station. It is sufficient that the medical facility F is a facility that provides some sort of medical services such as diagnosis, treatment, nursing, care, inspection, operation, and consultation, and the form and scale of the facility F do not matter.

In addition, it is assumed in FIG. 1 that the patients P, the medical workers M, and the patient-related persons R possess terminals 10, 11, and 12 of his/her own; however, the present invention is not limited to this. Since the patients P, the medical workers M, and the patient-related persons R have their identification information (user ID) which can be uniquely discriminated, and they are discriminated even if they log in to the medical support system 30 from the same terminal, commonly using the same terminal by a plurality of persons does not cause any problem.

Figure 2:
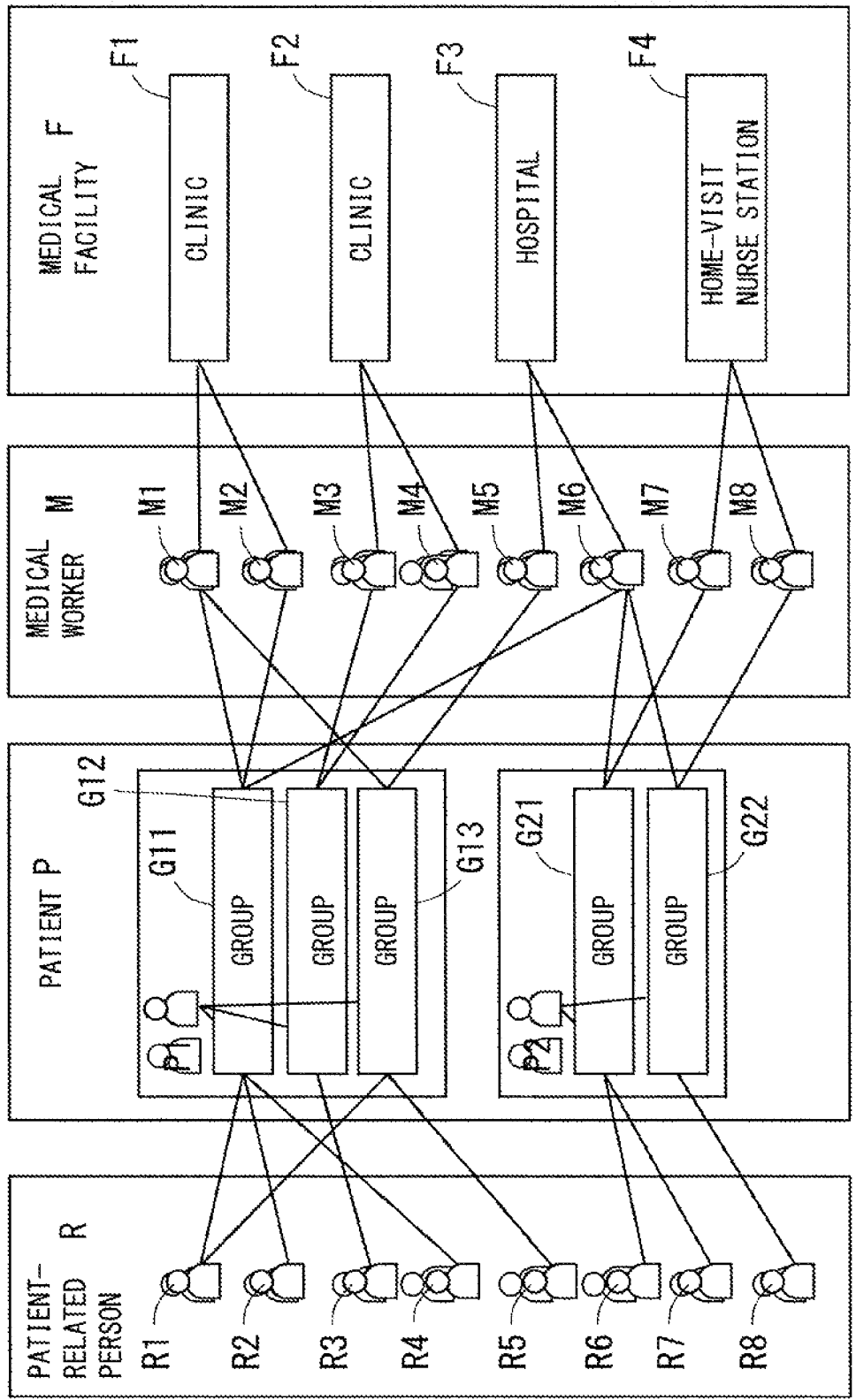
FIG. 2 is an explanatory diagram showing the relationships among the patients, patient-related persons, medical workers, and medical facilities which participate in the medical support system according to the embodiment of the present invention.

FIG. 2 is an explanatory diagram showing the relationships among the patients P1 and P2, the patient-related persons R1 to R8, and the medical workers M1 to M8 who utilize the medical support system 30 according to this embodiment, in other words, who are the users of the system 30.

In the medical support system 30, one group G is registered for each disease of each patient P. In other words, different groups G are generated for the respective diseases of each patient P. Usually, the persons who have participated in each group G (participants) (i.e., group members) include at least one medical worker M who belongs to the medical facility F in which the patient P receives medical treatment or the like, and a patient-related person or persons R who has/have been added according to the necessity, in addition to the patient P himself/herself. Therefore, it is usual that the group members of each group G include the patient P himself/herself, the medical worker M in charge, and the patient-related person or persons R.

It is usual that any one of the medical facilities F to which the medical workers M who have participated in each group G belong is subjected to "personalization registration" to the group G (and therefore, to the patient P) in question. The facility F which has been subjected to "personalization registration" is burdened with the principal responsibility of overall medical treatment policy for the disease of the patient P pertaining to the group G.

However, the composition of the group members is not limited to such the case as described above. For example, there are a case where only the patient P and the medical workers M are included as the group members, and a case where only the medical workers M are included as the group members (where both the patient P and the patient-related persons R are not included). For example, the former case arises when the patient P does not want to have his/her medical information known to the patient-related persons R. The latter case arises when the medical workers M want to share the medical information of their patient P whom these medical workers M are concerned with but do not want to have the same medical information known to the patient P. In addition, in the case where the patient P is not included in the group members, the patient's approval for sharing his/her medical information is unable to be obtained in the medical support system 30 and thus, the patient's approval needs to be obtained outside the system 30. For example, the patient's approval can be obtained in written form. Obviously, only the approval process by the patient P using a digitized form for patient's approval, which is prepared in advance, may be added to the system 30 for the sake of convenience. Needless to say, a subsystem for obtaining an approval for sharing his/her medical information from the patient P may be incorporated into the system 30 separately.

The participants (group members) excluding the patient P himself/herself in each group G are called "supporters" regardless of whether they are medical workers M or patient-related persons R. This is because they are the ones that support the patient P in some form. Therefore, it may be said that the group members of each group G include the patient P himself/herself and at least one supporter, if the patient P is included. If the patient P is not included, it may be said that the group members of each group G include only supporters.

In this embodiment, as seen from FIG. 2, the patient P1 suffers from three diseases (here, diabetes, hyperlipemia, and gout), and groups G11, G12, and G13 are generated for these three diseases, and medical facilities F are associated with each of the groups G11, G12, and G13. Concretely speaking, a clinic F1 is subject to personalization registration for the group G11 for treating diabetes, a clinic F2 is subject to personalization registration for the group G12 for treating hyperlipemia, and a hospital F3 is subject to personalization registration for the group G13 for treating gout. In this way, here, the patient P1 belongs to the three groups G11, G12, and G13. As explained later, medical workers M, who belong to one of the clinics F1 and F2 and the hospital F3 which are subjected to personalization registration, belong to the groups G11, G12, and G13.

The patient P2 suffers from two diseases (here, Alzheimer's disease and hypertension), and groups G21 and G22 are generated for these two diseases, and medical facilities F are associated with each of the groups G21 and G22. Concretely speaking, the hospital F3 is subject to personalization registration for the group G21 for treating Alzheimer's disease, and a home-visit nursing station F4 is subject to personalization registration for the group G22 for treating hypertension. In this way, here, the patient P2 belongs to the two groups G21 and G22. As explained later, medical workers M, who belong to one of the hospital F3 and the home-visit nursing station F which are subjected to personalization registration, belong to the groups G21 and G22.

As explained above, the group G 11 is a group for treating diabetes of the patient P1, the group G 12 is a group for treating hyperlipemia of the patient P1, and the group G 13 is a group for treating gout of the patient P1. The group G 21 is a group for treating Alzheimer's disease of the patient P2, and the group G 22 is a group for treating hypertension of the patient P2. In this way, a group G is prepared for each disease of each patient P and therefore, the medical information about a specific disease of a specific patient P is shared in each group G. Consequently, higher supporting effect on the treatment of the disease in question can be expected and as a result, better-quality medical service will be provided.

A medical worker M1 is a physician who belongs to the clinic F1 and belongs to the group G11 for treating diabetes of the patient P1 and the group G 13 for treating gout of the patient P1 as a supporter. A medical worker M2 is a nurse who belongs to the same clinic F1 as the worker M1 and belongs to the group G11 for treating diabetes of the patient P1 as a supporter.

A medical worker M3 is a physician who belongs to the clinic F2 and belongs to the group G12 for treating hyperlipemia of the patient P1 as a supporter. A medical worker M4 is a nurse who belongs to the same clinic F2 as the worker M3 and belongs to the group G12 for treating hyperlipemia of the patient P1 as a supporter.

A medical worker M5 is a physician who belongs to the hospital F3 and belongs to the group G13 for treating diabetes of the patient P1 as a supporter. A medical worker M6 is a physician who belongs to the same hospital F3 as the worker M5, and belongs to the group G11 for treating diabetes of the patient P1, the group G21 for treating Alzheimer's disease of the patient P2, and the group G22 for treating hypertension of the patient P2 as a supporter.

A medical worker M7 is a nurse who belongs to the home-visit nursing station F4 and belongs to the group G21 for treating Alzheimer's disease of the patient P2 as a supporter. A medical worker M8 is a nurse who belongs to the same home-visit nursing station F4 as the worker M7 and belongs to the group G22 for treating hypertension of the patient P2 as a supporter.

A patient-related person R1 is a member of the family of the patient P1 and belongs to the group G11 for treating diabetes of the patient P1 and the group G13 for treating gout of the patient P1 as a supporter. A patient-related person R2 is a relation of the patient P1 and belongs to the group G11 for treating diabetes of the patient P1 as a supporter. A patient-related person R3 is a member of the family of the patient P1 and belongs to the group G12 for treating hyperlipemia of the patient P1 as a supporter. A patient-related person R4 is a friend of the patient P1 and belongs to the group G11 for treating diabetes of the patient P1 as a supporter. A patient-related person R5 is a friend of the patient P1 and belongs to the group p G13 for treating gout of the patient P1 as a supporter.

A patient-related person R6 is a member of the family of the patient P2 and belongs to the group G21 for treating Alzheimer's disease of the patient P2 as a supporter. A patient-related person R7 is a relation of the patient P2 and belongs to the group G21 for treating Alzheimer's disease of the patient P2 as a supporter. A patient-related person R8 is a member of the family of the patient P2 and belongs to the group G22 for treating hypertension of the patient P2 as a supporter.

As explained above, in the medical support system 30 according to this embodiment, the groups G11, G12, and G13 are respectively formed for the three diseases (here, diabetes, hyperlipemia, and gout) of the patient P1, and the clinics F1 and F2 and the hospital F3 are personalization-registered for these groups G11, G12, and G13. Therefore, the medical workers M1 and M2 who belong to the clinic F1 are in charge of treatment for the disease (here, diabetes) of the group G11 of the patient P1 as attending physicians. The medical workers M3 and M4 who belong to the clinic F2 are in charge of treatment for the disease (here, hyperlipemia) of the group G12 of the patient P1 as attending physicians. The medical workers M5 and M6 who belong to the hospital F3 are in charge of treatment for the disease (here, gout) of the group G13 of the patient P1 as attending physicians.

The patient-related persons R1, R2, and R4 who belong to the group G11 of the patient P1 support the patient P1 by, for example, giving some advice to the patient P1 and the medical workers M1 and M2 about a treatment plan for diabetes. Among the patient P1, the medical workers M1 and M2, and the patient-related persons R1, R2, and R4 who belong to the group G11, the medical information about diabetes and communications (message exchange) can be shared according to the sharing rule which has been approved by the patient P1.

The patient-related person R3 who belong to the group G12 of the patient P1 supports the patient P1 by, for example, giving some advice to the patient P1 and the medical workers M3 and M4 about a treatment plan for hyperlipemia. Among the patient P1, the medical workers M3 and M4, and the patient-related person R3 who belong to the group G12, the medical information about hyperlipemia and communications (message exchange) can be shared according to the sharing rule which has been approved by the patient P1.

The patient-related persons R1 and R5 who belong to the group G13 of the patient P1 supports the patient P1 by, for example, giving some advice to the patient P1 and the medical workers M5 and M6 about a treatment plan for gout. Among the patient P1, the medical workers M5 and M6, and the patient-related persons R1 and R5 who belong to the group G13, the medical information about gout and communications (message exchange) can be shared according to the sharing rule which has been approved by the patient P1.

Similarly, the groups G21 and G22 are respectively formed for the two diseases (here, Alzheimer's disease and hypertension) of the patient P2, and the hospital F3 and the home-visit nursing station F4 are personalization-registered for the two groups G21 and G22. Therefore, the medical workers M5 and M6 who belong to the hospital F3 are in charge of treatment for the disease (here, Alzheimer's disease) of the group G21 of the patient P2 as attending physicians. The medical workers M7 and M8 who belong to the home-visit nursing station F4 are in charge of treatment for the disease (here, hypertension) of the group G22 of the patient P2 as attending physicians.

The patient-related persons R6 and R7 who belong to the group G21 of the patient P2 support the patient P2 by, for example, giving some advice to the patient P2 and the medical workers M6 and M7 about a treatment plan for Alzheimer's disease. Among the patient P2, the medical workers M6 and M7, and the patient-related persons R6 and R7 who belong to the group G21, the medical information about Alzheimer's disease and communications (message exchange) can be shared according to the sharing rule which has been approved by the patient P2.

The patient-related person R8 who belongs to the group G22 of the patient P2 support the patient P2 by, for example, giving some advice to the patient P2 and the medical workers M6 and M8 about a treatment plan for hypertension. Among the patient P2, the medical workers M6 and M8, and the patient-related person R8 who belong to the group G22, the medical information about hypertension and communications (message exchange) can be shared according to the sharing rule which has been approved by the patient P2.

The functions necessary for realizing the aforementioned sharing the medical information and communications (message exchange) are provided by the medical support system 30 in response to requests or instructions from the patient terminals 10, the medical worker terminals 11, or the patient-related person terminals 12, as described later.

[Structure and Functions of Medical Support System]

Figure 3:
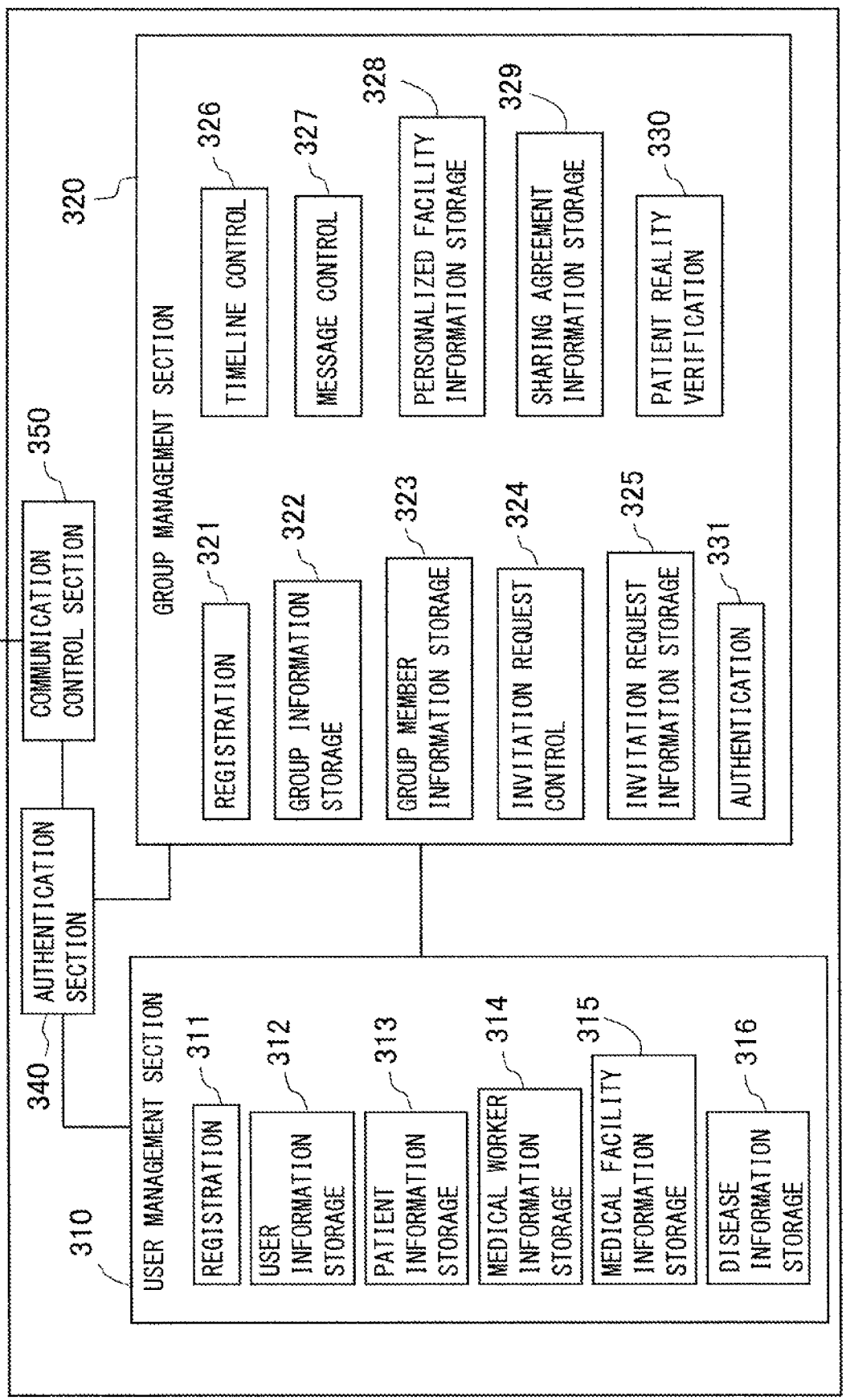
FIG. 3 is a functional block diagram showing the internal structure of the medical support system according to the embodiment of the present invention.

Next, the structure and functions of the medical support system 30 according to this embodiment will be explained below with reference to FIG. 3. FIG. 3 is a functional block diagram showing the internal structure of the medical support system 30.

As shown in FIG. 3, the medical support system 30 according to this embodiment comprises a user management section 310, a group management section 320, an authentication section 340, and a communication control section 350.

The communication control section 350 is a section for enabling the transmission and reception of information between the medical support system 30 and the user terminals (i.e., the patient terminals 10, the medical worker terminals 11, and the patient-related person terminals 12) by way of the Internet 20 as a communication network provided outside the system 30. Since the communication process of the communication control section 350 is carried out in a known manner, the explanation about it is omitted here.

The authentication section 340 is a section for personal authentication about whether or not a person who accesses the medical support system 30 by way of the Internet 20 from the user terminal 10, 11, or 12 is an authorized user who is registered as a user by the system 30.

The authentication section 340 is connected to the Internet 20 provided outside the medical support system 30 by way of the communication control section 350. The user management section 310 and the group management section 320 conduct transmission and reception of information to/from the patient terminals 10, the medical worker terminals 11, and the patient-related person terminals 12 which exist outside the system 30 under the condition of obtaining prescribed personal authentication in the authentication section 340. As long as a person is authenticated by the authentication section 340 as an authorized user, the access to the user management section 310 and the group management section 320 by the said person is permitted. The said user will be able to utilize the medical support service provided by the system 30 only after that.

The user authentication process by the authentication section 340 is carried out in a known manner. For example, a prescribed login screen (see FIG. 16B) is displayed on the user terminal 10, 11, or 12 in response to the request of a user and then, it is judged whether the user identification information (ID) and the password (PW) inputted on this screen are in accordance with those registered in the user management section 310. If the ID and PW are in accordance with the registered ones, the user is judged an authorized user, permitting the access to the user management section 310 and the group management section 320. If the ID and/or PW is/are not in accordance with the registered ones, the user is judged an unauthorized user, refusing the access to the user management section 310 and the group management section 320.

Next, the user management section 310 will be explained below.

The user management section 310 is a section for management of the registration (user registration) of respective users who utilize the medical services provided by the medical facilities F, or respective users who support the former users, that is, the patients P, the medical workers M, and the patient-related persons R; and for management of the registered users. The user management section 310 comprises a registration subsection 311, a user information storage subsection 312, a patient information storage subsection 313, a medical worker information storage subsection 314, a medical facility information storage subsection 315, and a disease information storage subsection 316.

The registration subsection 311 is formed by software for controlling the operation of this subsection 311 and controls the operation relating to the overall user registration in the user management section 310. For example the registration subsection 311 displays a prescribed user registration screen (see FIG. 16A) on the user terminal 10, 11, or 12 which has accessed the medical support system 30, and urges the person who wants to use the medical support service (the applicant for use) to input and send his/her prescribed personal information. If the prescribed personal information is transmitted to the system 30 from the user terminal 10, 11, or 12 in response to the urging, registration subsection 311 stores the personal information thus transmitted in the user information storage subsection 312 as the "user information" of the aforementioned applicant for use. Moreover, the registration subsection 311 reads out and utilizes the user information stored in the user information storage subsection 312, and corrects and deletes the stored user information, according to the necessity.

The user information storage subsection 312 is formed by an information storage medium such as a hard disk and software for controlling the operation such as recording, reproduction, and deletion of information with respect to the medium. The user information storage subsection 312 stores the user information, i.e., the necessary information of the patients P, the medical workers M, and the patient-related persons R as the users, in response to the instruction of the registration subsection 311. At this time, the user information storage subsection 312 assigns uniquely discriminable "user identification information" (user IDs) to the respective users.

The user information is stored, for example, in the form of the user table shown in FIG. 4A. The items of this user table are "user ID" (user identification information) assigned to the respective users, "login ID" and "password" necessary for the respective users to log in the medical support system 30, "registration date" which is a date on which each user is registered in the system 30, and a "status" which shows the effectiveness or ineffectiveness of the registration of each user. As the "login ID" assigned to the respective users, "e-mail addresses" which the users applied at the time of registration; this is to keep one-to-one correspondence between the "user IDs" assigned and the applicants for user registration (applicants for use). However, the e-mail address may be set as a separate item, and optional character strings with uniqueness or the like may be respectively assigned to the login IDs. "Password" is assigned for user authentication. "Registration date" is an item for recording the date on which the medical service has become available to each user. "Status" is an item for recording whether the user is in the available state where the user registration is effective and the medical service is available to the user in question or in the unavailable state where the user registration is ineffective and the medical service is unavailable to the user in question.

The patient information storage subsection 313 is formed by an information storage medium such as a hard disk and software for controlling the operation such as recording, reproduction, and deletion of information with respect to the medium. The patient information storage subsection 313 stores the personal information of the patients P in response to the instruction of the registration subsection 311. At this time, the patient information storage subsection 313 assigns uniquely discriminable "patient ID" to each patient P in response to the instruction of the registration subsection 311. The "patient ID" corresponds to "patient identification information" and to "service recipient identification information" also.

The personal information of the patients P is stored, for example, in the form of the patient table shown in FIG. 4B. The items of this patient table are "patient ID" (service recipient identification information) assigned to the respective patients P, "user ID" (user identification information) the respective users have, and "patient's name", "gender", "birthdate", "e-mail address", "address", and "telephone number" of the respective patients P. As the "e-mail address", the e-mail addresses which the users applied at the time of registration are used; however, another different e-mail address may be used for this purpose.

The medical worker information storage subsection 314 is formed by an information storage medium such as a hard disk and software for controlling the operation such as recording, reproduction, and deletion of information with respect to the medium. The medical worker information storage subsection 314 stores the personal information of the medical workers M in response to the instruction of the registration subsection 311. At this time, the subsection 314 assigns uniquely discriminable "medical worker ID" to the respective medical workers M. The "medical worker ID" corresponds to the "medical worker identification information" and to the "service worker identification information" also.

The personal information of the medical workers M is stored, for example, in the form of the medical worker table shown in FIG. 4C. The items of this medical worker table are "medical worker ID" (service worker identification information) assigned to the respective medical workers M, "user ID" (user identification information) which the respective medical workers have, and "medical facility ID" assigned to the respective medical facilities F to which the medical workers M belong, and "medical worker's name", "gender", "birthdate", and "occupation category" of the respective medical workers M. In the field of "occupation category", the occupation category such as physician and nurse is stored.

The medical facility information storage subsection 315 is formed by an information storage medium such as a hard disk and software for controlling the operation such as recording, reproduction, and deletion of information with respect to the medium. The medical-related facility information storage subsection 315 stores the necessary information of the medical facilities F in response to the instruction of the registration subsection 311. At this time, the subsection 315 assigns uniquely discriminable "medical-related facility ID" to the respective medical-related facilities F. The "medical facility ID" corresponds to the "medical facility identification information".

The necessary information of the medical facilities F is stored, for example, in the form of the medical facility table shown in FIG. 4D. The items of this medical facility table are "medical facility ID" (medical facility identification information) assigned to the respective medical facilities F, and "facility name", "facility type", "treatment subjects", "address", "telephone number", "homepage (HP)", "consultation hour", and "nearest station" of the respective medical facilities F. In the field of "facility type", the type of the medical facilities F such as medical clinic, hospital, and home-visit nursing station is stored.

The disease information storage subsection 316 is formed by an information storage medium such as a hard disk and software for controlling the operation such as recording, reproduction, and deletion of information with respect to the medium. The disease information storage subsection 316 stores the disease information in response to the instruction of the registration subsection 311. At this time, the subsection 316 assigns uniquely discriminable "disease ID" to the respective diseases. The "disease ID" corresponds to the "disease identification information".

The disease information is stored, for example, in the form of the disease table shown in FIG. 5B. The items of this disease table are the "disease ID" (disease identification information) assigned to the respective diseases, and "medical facility patient ID" defined by the medical facility patient table shown in FIG. 5A and "disease name". The "medical facility patient ID" is the identification information for showing the relationship (linkage) between the patients P and the medical facilities F which are personalization-registered to the patients P. In addition, the "disease ID is associated with the "medical facility patient ID" in the disease table; this is because the use of the "medical facility patient ID" facilitates the association or linkage between the "disease ID" and the "medical facility patient ID".

Next, the group management section 320 will be explained below.

The group management section 320 is a section for managing the groups G which are registered and formed for each disease of each patient P in the medical support system 30. For example, the group management section 320 performs a lot of functions such as registration of new groups, storage of the group member information, control of the invitation requests, timelines, messages, and personalization registration. The group management section 320 comprises a registration subsection 321, a group information storage subsection 322, a group member information storage subsection 323, an invitation request control subsection 324, an invitation request information storage subsection 325, a timeline control subsection 326, a message control subsection 327, a personalized facility information storage subsection 328, a sharing agreement information storage subsection 329, a patient reality verification subsection 330, and an authentication subsection 331.

The registration subsection 321 is formed by software for controlling the operation of this subsection 321 and generates and registers groups G for each disease of each patient P in response to the request of the medical workers M or the patients P. Moreover, this subsection 321 performs the process pertaining to the "personalization registration" (concretely speaking, the associating operation among the patients P, the diseases, and the medical facilities F) in response to the request of the medical workers M or the patients P.

It is the case where a medical worker M conducts the "patient personalization registration" that a groups G is generated in response to the request of a medical worker M. The "patient personalization registration" indicates that a patient P to whom a medical facility F to which the medical worker M belongs gives medical treatment and the disease of the said patient are registered in the medical support system 30. At this time, the medical worker M designates the patient P to whom the medical facility F to which he or she belongs gives medical treatment and his/her disease for registration in the system 30. This is to make it possible to share the medical information of the patient P in the medical facility F the worker M belongs to. The registration subsection 321 automatically generates a group G in synchronization with the "patient personalization registration", and stores the information pertaining to the group G thus generated in the group information storage subsection 322.

The number of the initial group members of the group G generated in this way is zero excluding the case where prescribed members (default members) are automatically invited. Both of the medical worker M who has conducted the "patient personalization registration" and the patient P who has been the target for the "patient personalization registration" are not included in the initial group members. To include the medical worker M who has conducted the "patient personalization registration" in the group members, the said medical worker M needs to send an invitation request to the worker M himself/herself and to approve the invitation request by himself/herself. Similarly, to include the patient P who has been the target of the "patient personalization registration" in the group members, the said patient P needs to send an invitation request to the said patient P himself/herself and to approve the invitation request by himself/herself.

It is the case where a patient P conducts a request for "personalization registration" that a groups G is generated in response to the request of a patient P. At this time, the patient P selects one of the medical facilities F from which the patient P himself/herself receives medical treatment or those from which the patient P himself/herself tries to receive medical treatment, and makes a request for "personalization registration" in order to obtain an approval from the facility F thus selected. This is to designate a medical facility F from which the patient P wants to receive medical treatment primarily and which is burdened with the principal responsibility of overall medical treatment policy of the said patient P. The registration subsection 321 generates a group G automatically in synchronization with the "personalization registration" and stores the information pertaining to the group G thus generated (group information) in the group information storage subsection 322. In addition, concretely speaking, the patient P, the disease, and the medical facility F are associated with each other in the "personalization registration".

With respect to the group G thus generated also, the number of the initial group members is zero excluding the case where default members are automatically invited. Both of the patient P who has requested the "personalization registration" and the medical worker M in the medical facility which has been the target for the "personalization registration" are not included in the initial group members. To include the patient P who has requested the "personalization registration" in the group members, the said patient P needs to send an invitation request to the patient P himself/herself and to approve the invitation request by the patient P himself/herself. Similarly, to include the medical worker M who has been related with the "personalization registration" in the group members, the said patient P who has requested the "personalization registration" needs to send an invitation request to the said medical worker M and to approve the invitation request by the said worker M.

The group information storage subsection 322 is formed by an information storage medium such as a hard disk and software for controlling the operation such as recording, reproduction, and deletion of information with respect to the medium. The group information storage subsection 322 stores the group information, that is, the information indicating what disease and which patient P are related with each group G and which facility F is registered as a "personalized facility".

The "group information" is stored, for example, in the form of the group table shown in FIG. 5C. This group table includes "group ID" as the group identification information, "group name" which indicates what disease the group is related with, and "patient ID" defined by the disease table shown in FIG. 5B, as the items.

The group member information storage subsection 323 is formed by an information storage medium such as a hard disk and software for controlling the operation such as recording, reproduction, and deletion of information with respect to the medium. The group member information storage subsection 323 stores the group member information, that is, the information pertaining to the patient P himself/herself which may be said the owner of each group G, and the medical workers M and the patient-related persons R who have participated in each group G as the supporters for the patient P.

The "group member information" is stored, for example, in the form of the group participation table shown in FIG. 5D. This group participation table includes "group participation ID" as the identification information attached to the action of "group participation" in one group G, "user ID" of the user who has participated in the group G in question, "group ID" of the group G in which the user has participated, and "accessible timeline" for designating the timeline to which each member is accessible, as the items. By using such the group participation table as described here, the group members who belong to each group G can be recorded and at the same time, which timeline which one of the group members can access in each group G (i.e., what access authority each of the group members has) can be recorded.

The invitation request control subsection 324 is formed by software for controlling the operation of this subsection 324. The invitation request control subsection 324 controls the "invitation request" which is sent to the non-group members (i.e., the patient P, the medical workers M, or the patient-related persons R) who are designated as the ones who are wished to participate in the group G. The invitation request control subsection 324 sends an invitation request to the non-group members thus designated in the form of e-mail in response to the instruction from a user, i.e., a medical worker M, a patient P, or a patient-related person R. Also, the section 324 receives replies (which indicate whether or not the invitation request is approved) from the user who has received the invitation request.

The invitation request is an invitation letter in the form of e-mail which are sent to the users who are wished to participate in a desired group G to be group members thereof. The transmission of an invitation request can be performed by any one of the patients P, the medical workers M, and the patient-related persons R. However, "permission" of a prescribed administrator needs to be obtained before transmission of an invitation request to the users who are wished to participate in a group G. This is determined by the administrator while considering the point of whether or not the users to be invited are appropriate as the group members and whether or not some hindrance will arise due to the participation of these users. As the administrator, a "medical worker-side administrator" and a "patient-side administrator" are appointed. The "medical worker-side administrator" is a medical worker M (which is a user also) having an authority to "permit" or "refuse" the transmission of an invitation request, and is established for each medical facility F or each group. As the "medical worker-side administrator", for example, a director or a head official of a clinic is designated. The "patient-side administrator" is a patient P himself/herself (which is a user also) or a user (e.g., a family member or a friend of a patient P) to whom an authority to "permit" or "refuse" the transmission of an invitation request has been given from the patient P, and is established for each patient P or each group. As the "patient-side administrator", for example, a parent, a spouse, a child or a close friend of the patient P is designated.

Usually, even in the case where a medical worker M transmits an invitation request and in the case where a patient P or a patient-related person R transmits an invitation request, it is prescribed that invitation requests are unable to be transmitted without permission obtained from both of the "medical worker-side administrator" and the "patient-side administrator". In other words, the approval and disapproval of transmission of invitation requests is configured in such a way as to be decided while considering both of the circumstances of the medical workers M and those of the patient P. This is because if a person becomes a group member, he/she can view the medical information and messages of the patient P and therefore, who becomes a group member will affect largely to both of the patient P and the medical workers M. However, the present invention is not limited to this. It may be prescribed that invitation requests can be transmitted if permission is obtained from any one of the "medical worker-side administrator" and the "patient-side administrator", or that invitation requests can be transmitted if permission is obtained from the "medical worker-side administrator" only. This point may be determined according to the necessity or desire.

In this way, in the medical support system 30, "permission" from at least one of the "medical worker-side administrator" and the "patient-side administrator" is necessary to "complete" the transmission of invitation requests ("completeness of invitation"). This is to prevent any problem from occurring due to addition of group members.

It is sufficient for a user who receives the invitation request which has been transmitted after obtaining the "permission" of both or at least one of the "medical worker-side administrator" and the "patient-side administrator" to "approve" the invitation if he/she participates in the group G designated by the said invitation request. By doing so, the user in question will be added as a group member automatically. If the user in question does not participate in the group G, it is sufficient to "refuse" the invitation. In this way, the user who has received the invitation request can choose the participation or non-participation in the group G by deciding whether or not to "approve" the invitation.

The user who has approved the invitation will be a member of the group G. All the group members (concretely, the medical workers M and the patient-related persons R) except for the patient P will become supporters for the said patient P. The medical information and messages about the patient P are shared among the group members according to the sharing rule which has been chosen by the patient P. Accordingly, for example, in the case where a second opinion about his/her own disease is wanted from a medical worker M of another medical facility F or in the case where patient-related persons R (e.g., a family member, relative, or friend of the patient P) who want the patient P to know about the medial treatment progress of his/her disease are present, an invitation request will be transmitted to these persons. By doing so, the medical information about a specific disease of each patient P in a medical facility F can be shared among the medical workers M including the medical workers in other medical facilities, the patient-related persons R, and the patient P himself/herself while securing the uniqueness.

The setting of the "medical worker-side administrator" and the "patient-side administrator" is stored in the invitation request information storage subsection 325. The "approval" processes by the "medical worker-side administrator" and the "patient-side administrator" are carried out by the invitation request control subsection 324. The generation and transmission of invitation requests and the reception of replies from the recipients of the invitation requests are carried out by the invitation request control subsection 324.

The invitation request information storage subsection 325 is formed by an information storage medium such as a hard disk and software for controlling the operation such as recording, reproduction, and deletion of information with respect to the medium. The invitation request information storage subsection 325 stores the "invitation request information", that is, a variety of the information which indicates to whom who transmits an invitation request and the information pertaining to the approval/disapproval of the invitation request by the administrators. Moreover, this subsection 325 stores the content of the replies from the recipients of the invitation request (approval and refusal of the invitation request) and the setting of the "medical worker-side administrator" and the "patient-side administrator" also.

The "invitation request information" is stored, for example, in the form of the invitation request table shown in FIG. 6A. This invitation request table includes as the items "invitation request ID" assigned to each invitation request, "invitation request source ID" which is the identification information of the user who transmits an invitation request, "invitation request approval/disapproval" which is the identification information indicating whether or not an invitation request may be transmitted, "invitation request approval" which is the identification information indicating whether or not the invitation request has been approved by the invited persons, "invitation destination user ID" which is the identification information of the destination to which an invitation request is to be transmitted, "invitation destination e-mail address" and "invitation destination passphrase" of the destination to which an invitation request is to be transmitted, "group ID" which is the identification information of the group to which persons are invited, and "accessible timeline" which indicates the code of a timeline to which the group members are accessible. In this way, in this invitation request table, if a destination e-mail address to which an invitation request is to be transmitted and an invitation destination passphrase which has been settled are known, an invitation request can be transmitted to anybody anytime.

Incidentally, the invitation request table in FIG. 6A includes the "invitation destination passphrase". This is to confirm whether or not the recipient of an invitation request is a formal destination invited, in other words, whether or not the recipient is a principal using this passphrase. To participate in the group of the invitation source pertaining to an invitation request, the recipient of the invitation request needs to access the URL described in the e-mail as the invitation request and to input the passphrase in the invitation request approval screen displayed therein. The recipient is unable to participate in the group in question unless the inputted passphrase is in accordance with the "invitation destination passphrase" stored in the invitation request table; therefore, personal identification of the invitation destination can be made easily.

The timeline control subsection 326 is formed by software for controlling the operation of this subsection 326. The timeline control subsection 326 controls the "timeline" (i.e., the information display area) which is assigned to each group G. Concretely speaking, an information display area called "timeline" is assigned to a newly generated group G, and the medical information to be shared is displayed in the timeline in a predetermined order (for example, in the order of contribution time). Since the information to be displayed and the parameters such as the display time are transmitted to the group management subsection 330 from a medical worker terminal 11 by way of the Internet 20, the timeline control subsection 335 displays the information thus transmitted in the timeline according to the parameters.

Figure 9:
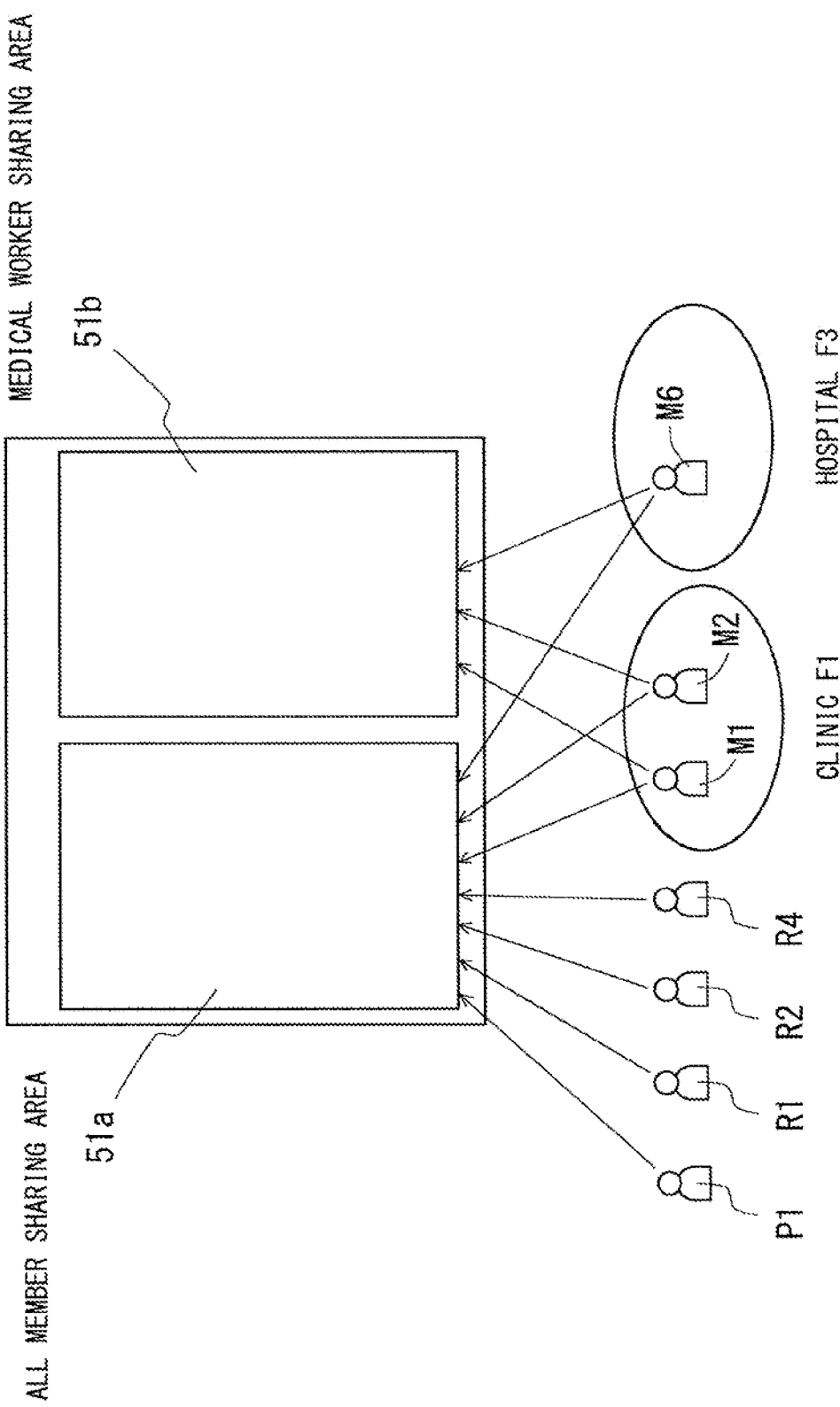
FIG. 9 is an explanatory diagram showing the relationships among the display areas generated for each disease of each patient which are formed by the medical support system according to the embodiment of the present invention, and the persons who can access the display areas.

An example of the timeline is shown in FIG. 9. The timeline 51 is generated for the group G11 of the patient P1 for treating diabetes, which comprises an all member sharing area 51a and a medical worker sharing area 51b. In the all member sharing area 51a, the information to be shared among all the members of the group G11 is displayed. In the medical worker sharing area 51b, the information to be shared among only the medical workers of the group G11 is displayed. Accordingly, the medical information displayed in the all member sharing area 51a can be shared among all the members of the group G11, and the medical workers M1 and M2 who belong to the clinic F1, the medical worker M6 who belongs to the hospital F3, and the patient-related persons R1, R2, and R4, in addition to the patient P1, are able to make contributions and to view the information freely. Unlike this, the medical information displayed in the medical worker sharing area 51b can be shared among only the medical workers of the group G11, and the medical workers M1 and M2 who belong to the clinic F1, and the medical worker M6 who belongs to the hospital F3 are able to make contributions and to view the information freely.

The message control subsection 327 is formed by software for controlling the operation of this subsection 327. The message control subsection 327 controls the transmission and reception of the messages which are addressed from one of the group members to another. This control uses the message transmission reservation table shown in FIG. 7A. The items of this message transmission reservation table are "transmission reservation ID" which is the identification information assigned to each transmission reservation, "destination user ID" which is the identification information of the user to which a message is to be transmitted, "sender user ID" which is the identification information of the user who will transmits a message, "message" which is the content to be transmitted, and "scheduled transmission date and time" which is the scheduled date and time on which a message will be transmitted.

The patient attribute table shown in FIG. 7B, which is prepared for storing the attribute of each patient P, is used when the message control subsection 336 transmits selectively a predetermined message to a part of the patients P. This table comprises as the items "patient attribute ID" which is the identification information attached to the attribute of each patient P, "patient ID" of each patient P, "attribute name" of each patient P, and "attribute value" of each patient P. The value of "medical examination guide in 2013" stored in "attribute name" indicates that an "announcement for guiding a medical examination in 2013" needs to be transmitted to this patient P, and the value of "yet" stored in "attribute value" indicates that the "announcement for guiding a medical examination in 2013" is not transmitted yet. Therefore, if the value of "medical examination guide in 2013" is stored in the "attribute name" and the patient ID where the value of the "attribute value" is "yet" is chosen, the "announcement for guiding a medical examination in 2013" can be transmitted to the patients P having the same attribute in a lump. Since this transmission can be reserved using the message transmission reservation table, it is very convenient.

The personalized facility information storage subsection 328 is formed by an information storage medium such as a hard disk and software for controlling the operation such as recording, reproduction, and deletion of information with respect to the medium. The personalized facility information storage subsection 328 stores the "personalized facility information" which is utilized in the process of "personalization registration" (associating the patient P, the disease, and the medical facility F) and which is generated therein.

The personalization registration process is as follows. As explained above, there are the case where the "personalization registration" is performed in response to the request of a medical worker M and the case where it is performed in response to the request of a patient P. In the former case, a medical worker M makes an inquiry "Do you make a personalization registration?" to a patient P whom the medical worker M takes charge of. If the patient P approves it, the registration subsection 321 conducts the personalization registration. In the latter case, a patient P makes an inquiry "I want to make a personal registration of your facility to me. Are you OK?" to a medical facility F (to which a desired medical worker M belongs) from which the patient receives medical treatment or that from which the patient P tries to receive medical treatment. If the facility F (the medical worker M) approves it, the registration subsection 321 conducts the personalization registration.

To realize the aforementioned inquiry for personalization registration, the invitation request function and the reception function for receiving replies to the invitation request, both of which are provided in the invitation request control subsection 324, are used. In other words, in the invitation request requesting a user to participate in a group G, a comment having the meaning of "An invitation to a group has reached. Do you participate in it?" is included. On the other hand, in the invitation request asking for the personalization registration request, the aforementioned comment is included. These two invitation requests are different only at this point, and the remainder is the same. Therefore, it may be said that e-mails for personalization registration request (a request for personalization registration) is a special case of e-mails for invitation request (a request for participating a group).

For example, when a medical worker M who belongs to a certain medical facility F requests a patient P who receives medical treatment for a disease from the medical worker M to make a personalization registration of the said facility F for the said disease, the registration subsection 321 displays a prescribed personalization registration request screen on the medical worker terminal 11 in response to the instruction of the said worker M. On the said screen, the said worker M is urged to input an e-mail address of the patient P pertaining to personalization registration and to transmit a personalization registration request. If an e-mail address is inputted and the "transmit" button is clicked, the registration subsection 321 transmits an e-mail for requesting a personalization registration in the same form as the invitation request to the said e-mail address. If the patient P who receives the e-mail for personalization registration request clicks the "approve" button included in the said e-mail, the registration subsection 321 generates "personalized facility information" in association with the information about the patient P, the disease, and the facility F pertaining to the personalization registration, and stores the "personalized facility information" thus generated in the personalized facility information storage subsection 328.

Before transmitting an e-mail for personalization registration request to a patient P, the registration subsection 321 checks whether or not personalized facility information has been generated for the same medical facility F about the same disease of the same patient P. If the same personalized facility information is present, the registration subsection 321 does not generate new personalized facility information, and displays the fact of the existence of the same personalized facility information on the medical worker terminal 11 to finish the personalization registration process. This is to surely prevent duplication of personalization registration, thereby preventing the situation where duplicated medical information about the same disease of the same patient P exists in the same medical facility F. It is only the case where the same personalized facility information does not exist that the registration subsection 321 generates new personalized facility information and stores it in the personalized facility information storage subsection 322.

The medical worker M who belongs to the medical facility F which has been subjected to personalization registration, and the patient P need to be members of the same group G. This is because the fact that both of the medical worker M and the patient P in question are members of the same group G is a requirement for sharing the medical information of the patient P and the messages among the group members to thereby improve the medical service which is provided by the medical worker M to the patient P. However, the timing for becoming a member of a group G may be before or after the personalization registration. A group G is generated in the case where a medical worker M conducts "patient group registration" and in the case where a patient conducts "personalization registration", and the number of initial group members of a group G thus generated is zero except that prescribed members (default members) are automatically invited. Therefore, it is preferred to send an invitation request to the medical workers M and the patient P who are related to personalization registration as early as possible, thereby urging the workers M and the patient P in question to participate in the group G.

The aforementioned "personalization registration" is conducted based on the approval of a patient P to a personalization registration request by a medical worker M. However, a patient P himself/herself may conduct personalization registration spontaneously about the medical facility F from which the said patient P receives medical treatment for a certain disease thereof. In this case, the registration subsection 321 displays a prescribed personalization registration screen on the patient terminal 10 in response to the instruction of the patient P and urges the patient P to designate a medical facility F which the patient P wants to conduct personalization registration. For example, on the patient terminal 10, the registration subsection 321 guides a patient P to select and designate a medical facility F which the patient P wants to be personalization-registered from the medical facilities F registered in the medical support system 30, and urges the patient P to retrieve the registered facilities F to designate a desired one. If the patient P designates a specific medical facility F and clicks the "personalization registration" button, the registration subsection 321 generates "personalized facility information" by associating the information about the patient P, the disease, and the medical facility F with each other, and stores the "personalized facility information" thus generated in the personalized facility information storage subsection 328. In this case, the patient P himself/herself who conducts the personalization registration may be set as a default member. If so, the patient P himself/herself will be a group member from the initial generation of a group G and thus, transmission of an invitation request will be unnecessary.

For example, in the case where the patient P1 conducts personal registration of the medical facilities F1 and F2 spontaneously, the medical information about different diseases of the patient P1, which has been dealt separately in the facilities F1 and F2 because whether or not the patient P1 is the same person is unknown, will be able to be found that of the same person in the medical supports system 30. For this reason, the medical information which is stored separately in different medical facilities can be integratively managed, stored, and viewed as the medical information of the same patient in the system 30. Similarly, in the case where the patient P1 conducts personal registration of three or more medical facilities F1, F2, F3 . . . spontaneously, the medical information about the disease(s) stored in these facilities F1, F2, F3 . . . is integrated as the medical information of the same patient P1 in the system 30 and can be managed in a centralized fashion therein.

The "personalized facility information" is stored, for example, in the form of the medical facility patient table shown in FIG. 5A. The items of this medical facility patient table are "medical facility patient ID" which is assigned to each patient P who receives medical treatment in each medical facility F, "medical facility ID" which is defined by the medical facility table shown in FIG. 4D, "patient number" of the patient P in the medical facility F, and "patient name", "gender", "birthdate", "insurance", "final check-up date", "address", "telephone number", "e-mail address", and "passcode" of the patient P. The "medical facility patient ID" is the identification information showing the relationship between the patient P and the medical facility F which is personalization-registered by the patient P, and may be said the "personalized facility identification information" or "medical facility-patient relationship identification information". The "patient number" is the identification information of the patient P who receives medical treatment in the said medical facility F. The "passcode" is the information assigned to each patient P for identity verification and is used when the patient P approves the personalization registration request.

The "personalized facility information" is stored in the personalized facility information storage section 328 in the manner as described above; however, during this process, the registration subsection 321 displays a prescribed sharing agreement screen on the patient terminal 10 and makes an inquiry whether or not the patient P agrees to share his/her medical information about a specific disease in the medical facility F pertaining to the personalization registration. If the reply is "not to agree to share", the section 328 conducts the personalization registration under the condition that the medical information is not shared. The reply "not to agree to share" also is stored in the sharing agreement information storage subsection 323; however, in this case, the advantage obtained from personalization registration is only the transmission, reception, and sharing of messages among the group members and sharing them.

In addition, when the patient P does not agree to share his/her medical information, the medical support system 30 may be configured in such a way that personalization registration itself is not conducted.

In the medical support system 30, an agreement to share the medical information cannot be obtained from the patient P until personalization registration is conducted and therefore, the medical information cannot be shared among the medical workers M who belong to the group G. However, if so, it is inconvenient and in addition, there is a wish to share the medical information among the medical workers M for the purpose of improving the medical service. For this reason, if an agreement to share the medical information is obtained in writing from the patient P outside the medical support system 30, the medical information can be shared in the system 30 by making such a setting as described here. However, the sharing range in this case is limited to the medical workers M who belong to the group G.

The registration subsection 321 displays a prescribed sharing rule selection screen in the aforementioned inquiry screen for sharing the medical information and urges to select the selection rule, i.e., the sharing range of the medical information. For example, the sharing rules comprise two alternatives, one of which is "to share only in the medical facility F pertaining to personalization registration" and the other is "to share in all the group members, including the inside of the medical facility F pertaining to personalization registration, and the patient P himself/herself pertaining to personalization registration". When one of the sharing rules is selected, the registration subsection 321 stores the reply of "to agree to share" and the sharing rule thus selected in the sharing agreement information storage subsection 329.

Needless to say, the sharing rules may include three or more alternatives. In this case, an alternative of "to share the medical information of the patient P excluding the messages" may be added to the aforementioned two alternatives.

The aforementioned selection process for selecting the sharing rule of the medical information of the patient P is the same in the case of personalization registration by a medical worker M and in the case of personalization registration by a patient P also.

The sharing agreement information storage subsection 329 is formed by an information storage medium such as a hard disk and software for controlling the operation such as recording, reproduction, and deletion of information with respect to the medium. The sharing agreement information storage subsection 329 stores the indication of intention of "to agree the sharing of his/her own medical information" (sharing agreement information) which has been generated by the registration subsection 321, and the sharing rule selected.

The sharing agreement information and the sharing rule selected are stored, for example, in the form of the medical information sharing table shown in FIG. 6C. The items of the medical information sharing table are "user ID" of each patient P, "medical facility ID" of the medical facility F which has been personalization-registered, and "sharing rule" with which the patient P has agreed. In the medical information sharing table shown in FIG. 6C, the patient P whose user ID is "100" gives "approval to share in the facility" in the medical facility F whose medical facility ID is "1000" and "approval to share comprehensively" in the medical F whose medical facility ID is "1001".

Here, "approval to share in the facility" indicates that, for example, the patient P agreed the sharing only in the clinic F1 which the patient P has personalization-registered, in other words, only among the medical workers M1 and M2 who belong to the clinic F1. This means that the medical information of the patient P1 about diabetes is restrictively shared among the medical workers M1 and M2 of the clinic F1 who belong to the group G11.

"Approval to share comprehensively" indicates that the patient P agreed the sharing among not only the medical workers M1 and M2 who belong to the clinic F2 but also the patient P1 himself/herself and the patient-related person R3 of the patient P1 who has participated as a supporter. This means that the medical information of the patent P1 about hyperlipemia is shared among the medical workers M3 and M4 of the clinic F2 who belong to the group G12, the patient P1 himself/herself, and the patient-related person R3, in other words, it is shared among all the group members.

In addition, in the medical information sharing table shown in FIG. 6C, in the case where the intention of not agreeing to share is expressed, although personalization registration is conducted, the sharing disagreement information is not stored in the medical information sharing table.

However, it is needless to say that the sharing disagreement information may be stored in the medical information sharing table.

The patient reality verification subsection 330 is formed by software for controlling the operation of this subsection 330 and verifies "whether or not the patient P who has requested a personalization registration exists really", in other words, "whether or not the said patient P is a person himself/herself and is not a masquerade by another person". It is preferred that this patient reality verification process is carried out before the aforementioned personalization registration process starts.

For example, in the case where a new patient P receives medical treatment in a certain medical facility F, a medical worker M (or a staff member) inputs a patient number in the said facility (which is different from the patient ID in the medical support system 30) into the system 30 using a receipt computer provided in the said facility, thereby issuing a provisional passcode. By doing so, the new patient user having this provisional passcode will be provisionally registered in the system 30 which is in cooperation with the said receipt computer. Thereafter, a "written registration form" on which the provisional passcode thus issued and the URL (and the QR code (which is a registered trademark)) for user registration in the system 30 have been printed is handed to the new patient P at the consulting or reception time. Moreover, to conduct user registration, the new patient P is asked to access the said URL on the patient terminal 10 of his/her own, and to input his/her patient number, name, birthdate, and the provisional passcode which is printed on the registration form, on the user registration screen displayed on the same terminal 10.

In response to this, the patient reality verification subsection 330 judges whether or not all of the patient number, name, birthdate, and provisional passcode which have been inputted on the user registration screen and transmitted are in accordance with those which have been registered provisionally in the medical support system 30. If they are in accordance with the provisionally registered ones, regular user registration is conducted; and if they are not in accordance with them, regular user registration is refused. In this way, whether or not the person who has applied user registration is the aforementioned new patient himself/herself can be verified according to whether or not the aforementioned provisionally registered user can be regularly registered.

This patient reality verification process may be performed using a NFC (Near Field Communication) terminal which is capable of short distance radio communication. For example, a NFC terminal is mounted at the window of a medical facility F in advance. The NFC terminal has been configured in such a way that if a patient P makes a contact of his/her patient terminal 10 with the NFC terminal, the terminal number of the NFC terminal will be read out by the patient terminal 10 automatically using infrared communication or the like. Thereafter, it is sufficient that the medical worker M or staff member (e.g., clerk) in the medical facility F asks the patient P "please make a contact of your patient terminal 10 with the NFC terminal placed at the window and then, access the user registration URL of the medical support system 30 which will be displayed on the patient terminal 10 to conduct user registration". By doing so, it is unnecessary to print the provisional passcode on the "written registration form" and to deliver the said form. In addition, the user registration process in this case is the same as the aforementioned case using the "written registration form".

An example of the NFC terminal table which is prepared for managing the NFC terminals is shown in FIG. 6D. This NFC terminal table comprises "medical facility ID" which is assigned to each medical facility F, "NFC terminal number" which is assigned to each NFC terminal, "medical facility patient ID" which is assigned to each patient P in each medical facility F and which is defined by the medical facility patient table of FIG. 5A, and "passcode" which is assigned to each patient P, as the items. The passcodes included in the item of "passcode" of the NFC terminal table are the same as those included in the item of "passcode" of the medical facility patient table of FIG. 5A.

The authentication subsection 331 is formed by software for controlling the operation of this subsection 331. This section 331 checks whether or not a patient P, a medical worker M, or a patient-related person R who has accessed a specific group G by way of his/her user terminal is a regular member of the said group G, in other words, whether or not the accessed person has an authority to access the timeline of the said group. If it is confirmed that the accessed person is a regular member, the authentication subsection 331 approves the access to the timeline of the group G. If it is confirmed that the accessed person is not a regular member, the subsection 331 refuses the access to the timeline of the group G.

Figure 8:
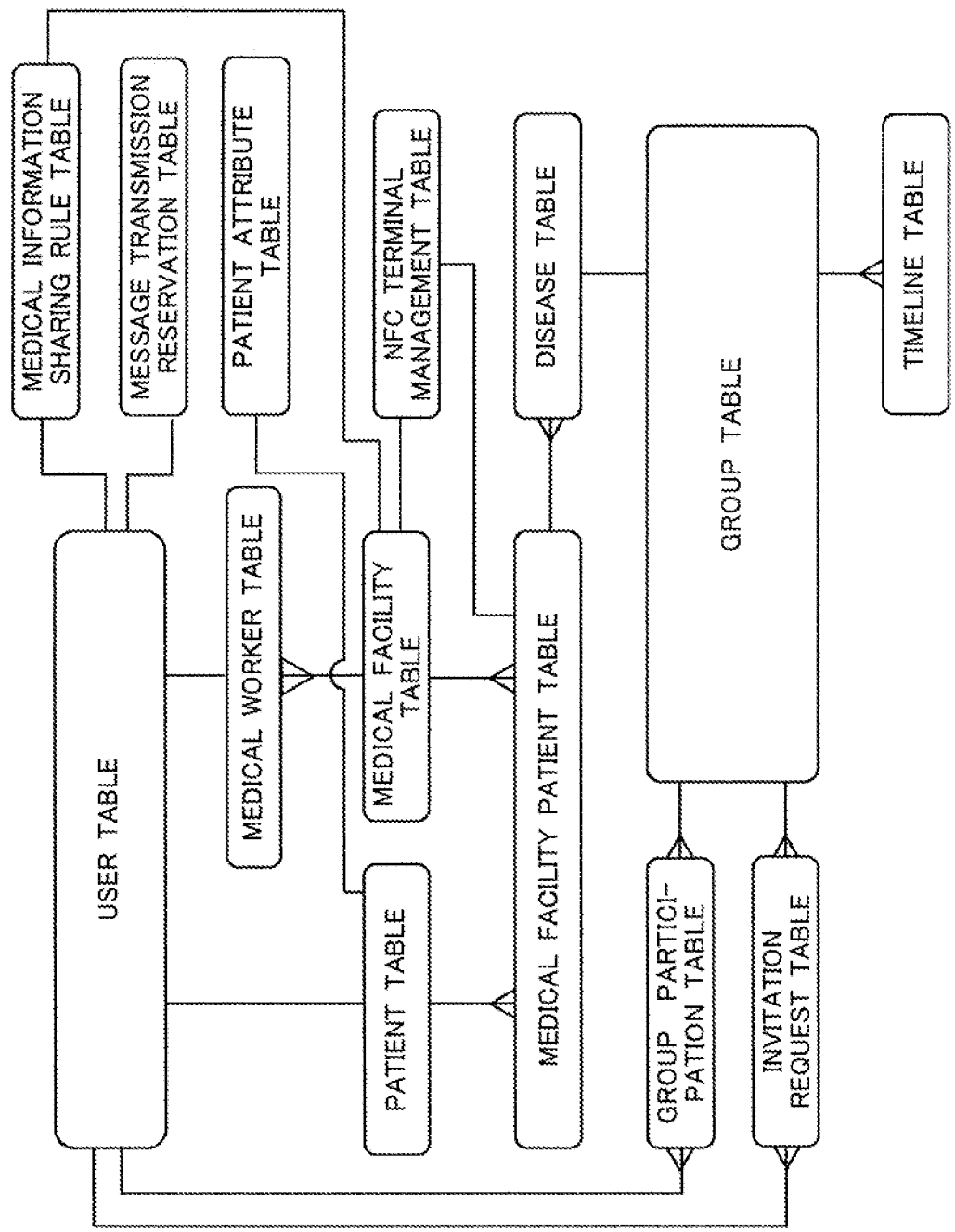
FIG. 8 is an explanatory diagram showing the relationships among all the tables used in the medical support system according to the embodiment of the present invention.

The aforementioned tables used in the medical support system 30 have relationships shown in FIG. 8. Specifically, the user table is associated with the patient table, the medical worker table, the medical information sharing table, the invitation request table, and the group table by way of the "user ID" (or the "inviting user ID", the "invited user ID", or the "sender user ID"). The patient table is further associated with the medical facility table and the medical facility patient table by way of the "patient ID". The medical worker table is further associated with the medical facility table by way of the "medical facility ID". The medical facility table is associated with the disease table, the medical information sharing table, and the NFC terminal management table by way of the "medical facility patient ID". The group table is associated with the group participation table, the invitation request table, the timeline table, and the disease table. The NFC terminal management table is associated with the medical facility table and the medical facility patient table. The patient attribute table is associated with the patient table.

[Operation of Medical Support System]

Next, the various operations of the medical support system 30 according to the embodiment having the aforementioned structure will be explained with reference to FIGS. 10 to 26.

[User Registration]

FIG. 10 is a flowchart showing a series of actions for new user registration by an applicant for utilizing the medical support service in the medical support system 30 according to the present embodiment.

The registration subsection 311 of the user management section 310 of the medical support system 30 waits continuously the access from an applicant for use, as shown in FIG. 10 (step S11). If the access from an applicant for use (concretely, a medical worker M, patient P, or patient-related person R) is received, the registration subsection 311 displays a prescribed "new user registration screen" on the applicant's terminal and urges the applicant to input and transmit his/her predetermined personal information (step S12). The "new user registration screen" is, for example, a screen shown in FIG. 16A, which urges the applicant to input and transmit, for example, his/her name and e-mail address. At that time, this screen urges the applicant to select whether to be registered as a "patient" or "medical worker" in the division of user registration. This is because the service to be provided and the viable things are largely different according to which division the applicant is registered in. Thereafter, the registration subsection 311 judges whether or not the personal information (name and e-mail address) transmitted from the said terminal is the predetermined one (step S13).

In the case where the personal information received is not the predetermined one, for example, if the e-mail address is not inputted in the correct notation, the registration subsection 311 displays the error-reinput screen on the applicant's terminal and urges the applicant to reinput his/her personal information (step S14). If the personal information received is the predetermined one, the registration subsection 311 assigns a user ID and a password (PW) to the personal information thus received and stores it in the user information storage subsection 312 (step S15). Thereafter, the section 311 transmits an e-mail for notifying the completion of user registration and informing the user ID and PW to the e-mail address thus received. In this way, the new user registration is completed.

[New Patient Registration]

The registration subsection 311 asks the applicant for use who has conducted the user registration (a new user) in the aforementioned manner to register his/her detailed personal information. Since the matters to be registered are different in the case where the applicant is registered as a patient (patient registration) and the case where the applicant is registered as a medical worker (medical worker registration), these two cases will be explained separately.

FIG. 11A is a flowchart showing a series of actions for new patient registration by a user of the medical support service in the medical support system 30.

First, the authentication section 340 of the medical support system 30 displays a prescribed "login screen" on the patient terminal 10 of the patient P who has accessed to the system 30 and urges to login, as shown in FIG. 11A (step S21). As the "login screen", for example, the screen shown in FIG. 16B is used. In response to this, the patient inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S22). If one or both of the user ID and PW is/are not in accordance with, the authentication section 340 displays the error screen to urge the reinput of them (step S23). If both of the user ID and PW are in accordance with, the registration subsection 311 of the user management section 311 displays a prescribed new patient registration screen on the patient terminal 10 to urge the applicant to input his/her detailed personal information (step S24).

As the new patient registration screen, for example, the screen shown in FIG. 17A is used. In this case, the name of the patient P is automatically inputted into the field of the patient's name by the registration subsection 311 and therefore, the patient P inputs his/her own address, birthdate, telephone number, and e-mail address, and selects, for example, "female", and thereafter, clicks the "transmission" button.

Subsequently, the registration subsection 311 judges whether or not the patient information transmitted from the patient terminal 10 is in accordance with a predetermined one (step S25). If the patient information received is not in accordance with the predetermined one, for example, in the case where the telephone number is not inputted or the e-mail address is not inputted in the correct notation, the registration subsection 311 displays the error-reinput screen on the patient terminal 10 and urges to reinput his/her medical information (step S26). If the medical information received is in accordance with the predetermined one, the registration subsection 311 assigns a patient ID to the user ID pertaining to the patient information thus received and stores it in the patient information storage subsection 313 (step S27). Thereafter, the subsection 311 transmits an e-mail for notifying the completion of patient registration and informing the assigned patient ID to the e-mail address thus received (step S28). In this way, the new patient registration is completed. In addition, needless to say, the notification of the completion of patient registration and advice of the patient ID may be carried out by another method, such as displaying them on the patient terminal 10 and handing a written form on which the patient ID is printed to the patient without using e-mail.

[New Medical Worker Registration]

Next, the case where the applicant is registered as a medical worker (medical worker registration) will be explained. FIG. 11B is a flowchart showing a series of actions to be performed when the same user conducts medical worker registration newly.

The process of new medical worker registration is the same as the aforementioned process of new patient registration except for the information to be registered. Specifically, first, the authentication section 340 of the medical support system 30 displays a prescribed "login screen" (see FIG. 16B) on the medical worker terminal 11 of the medical worker M who has accessed the system 30 and urges to login, as shown in FIG. 11B (step S31). In response to this, the medical worker M inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S32). If one or both of the user ID and PW is/are not in accordance with, the authentication section 340 displays the error screen to urge the reinput of them (step S33). If both of the user ID and PW are in accordance with, the registration subsection 311 of the user management section 311 displays a prescribed new medical worker registration screen on the medical worker terminal 11 to urge to input his/her detailed personal information (step S34).

As the new medical worker registration screen, for example, the screen shown in FIG. 17B is used. In this case, the name of the medical worker M is automatically inputted into the field of the medical worker's name by the registration subsection 311 and therefore, the medical worker M inputs his/her own birthdate, and the facility name, facility type, treatment subjects, facility address, telephone number, homepage (HP), consultation hour, and nearest station of the medical facility to which the said medical worker M belongs, and selects, for example, "male" as "gender" and "physician" as the occupation type, and thereafter, clicks the "transmission" button.

Subsequently, the registration subsection 311 judges whether or not the medical worker information transmitted from the medical worker terminal 11 is in accordance with a predetermined one (step S35). If the medical worker information received is not in accordance with the predetermined one, for example, in the case where the telephone number is not inputted or the address of the medical facility is not inputted in the correct notation, the registration subsection 311 displays the error-reinput screen on the medical worker's terminal 11 and urges to reinput his/her medical worker information (step S36). If the medical worker information received is the predetermined one, the registration subsection 311 assigns a medical worker ID to the user ID pertaining to the medical worker information thus received and stores it in the medical worker information storage subsection 314 (step S37). Moreover, the registration subsection 311 stores the medical worker information and the medical facility information in the medical worker information storage subsection 314 and the medical facility information storage subsection 315, respectively. Thereafter, the subsection 311 transmits an e-mail for notifying the completion of medical worker registration and informing the assigned medical worker ID to the e-mail address which has been registered as the login ID (step S38). In this way, the new medical worker registration is completed. In addition, needless to say, the notification of the completion of medical worker registration and advice of the medical worker ID may be carried out by another method, such as displaying them on the medical worker terminal 11 and handing a written form on which the medical worker ID is printed to the medical worker M without using e-mail.

When the new patient registration or new medical worker registration is completed in the aforementioned manner, the user will be able to utilize variety of services as the patient P or the medical worker M. The main menus which are displayed at those times are shown in FIGS. 30 and 31.

Figure 30:
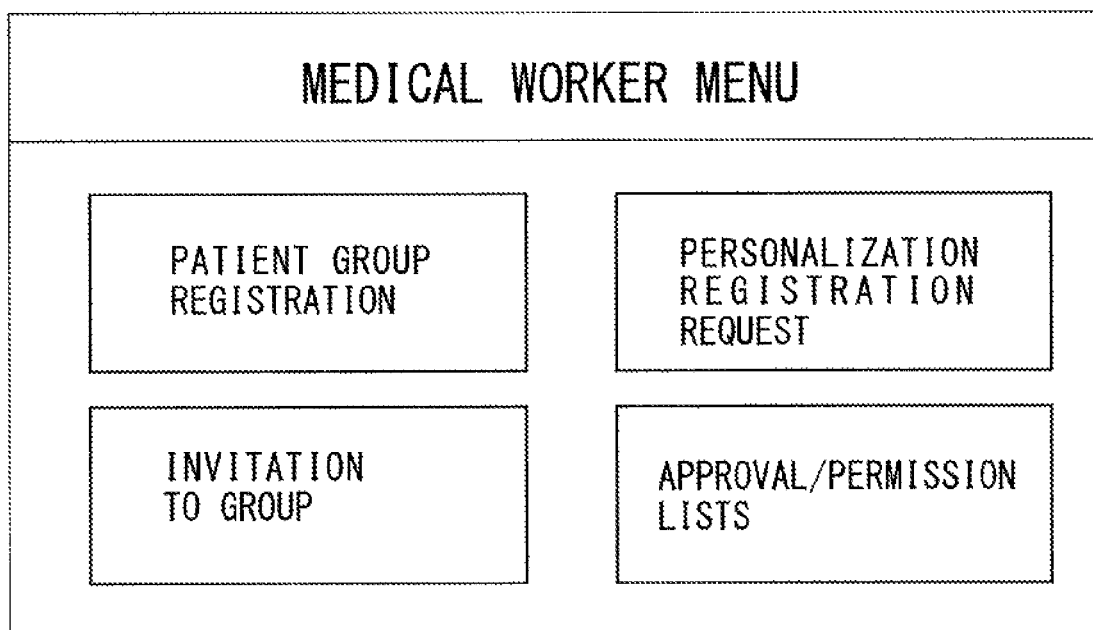
FIG. 30 is an explanatory diagram showing an example of a medical worker menu used in the medical support system according to the embodiment of the present invention.
Figure 31:
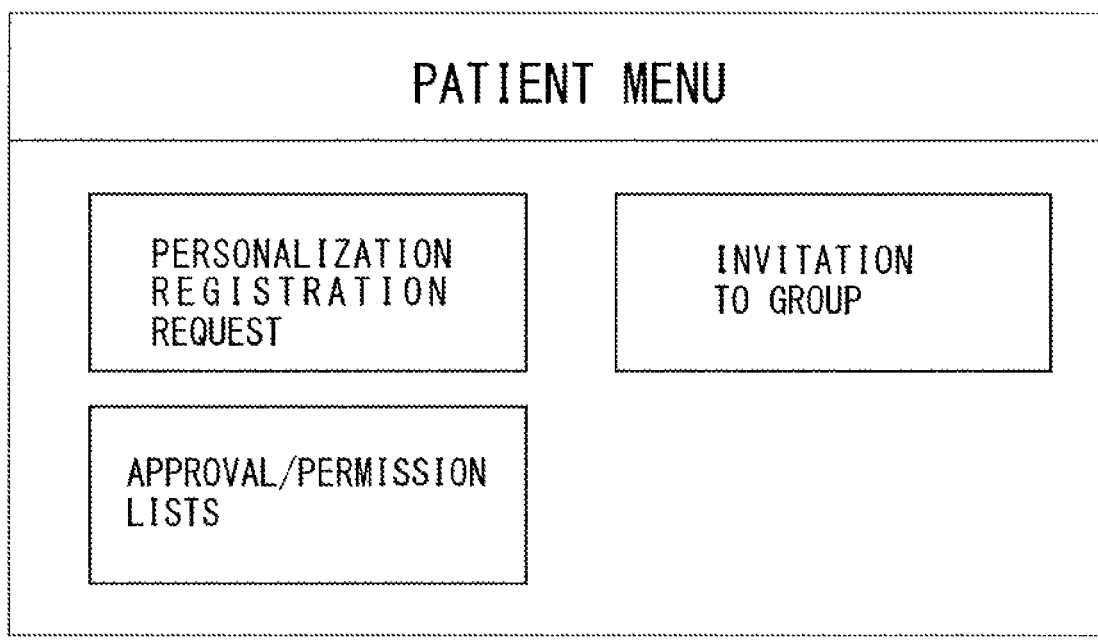
FIG. 31 is an explanatory diagram showing an example of a patient menu used in the medical support system according to the embodiment of the present invention.

FIG. 30 shows an example of the main menu for a medical worker M, in which four buttons termed "patient group registration", "personalization registration", "invitation to group" and "approval/permission lists" are displayed. FIG. 31 shows an example of the main menu for a patient P, in which three buttons termed "personalization registration", "invitation to group" and "approval/permission lists" are displayed. In addition, the "approval/permission lists" button is a button for selecting the functions, for example, approval for transmission of an invitation request and permission for an invitation request.

[Registration and Generation of Group]

In the medical support system 30 according to the present embodiment, a group is registered and generated for each disease of each patient P for the purpose of sharing the medical information and messages. The registration and generation are carried out in the patient group registration by a medical worker M or the personalization registration by a patient P. Therefore, the patient group registration will be explained first and thereafter, the personalization registration by a medical worker M will be explained. In the following explanation, a disease of a patient P is also registered in addition to the name of the patient P when conducting the patient group registration; however, the registration of a disease may be omitted. In this case, the medical support system 30 is configured in such a way that the number of groups to be generated for each patient P is limited to unity and thus, the operation of the system 30 will be made simple.

[Patient Group Registration by Medical Worker]

Figure 29:
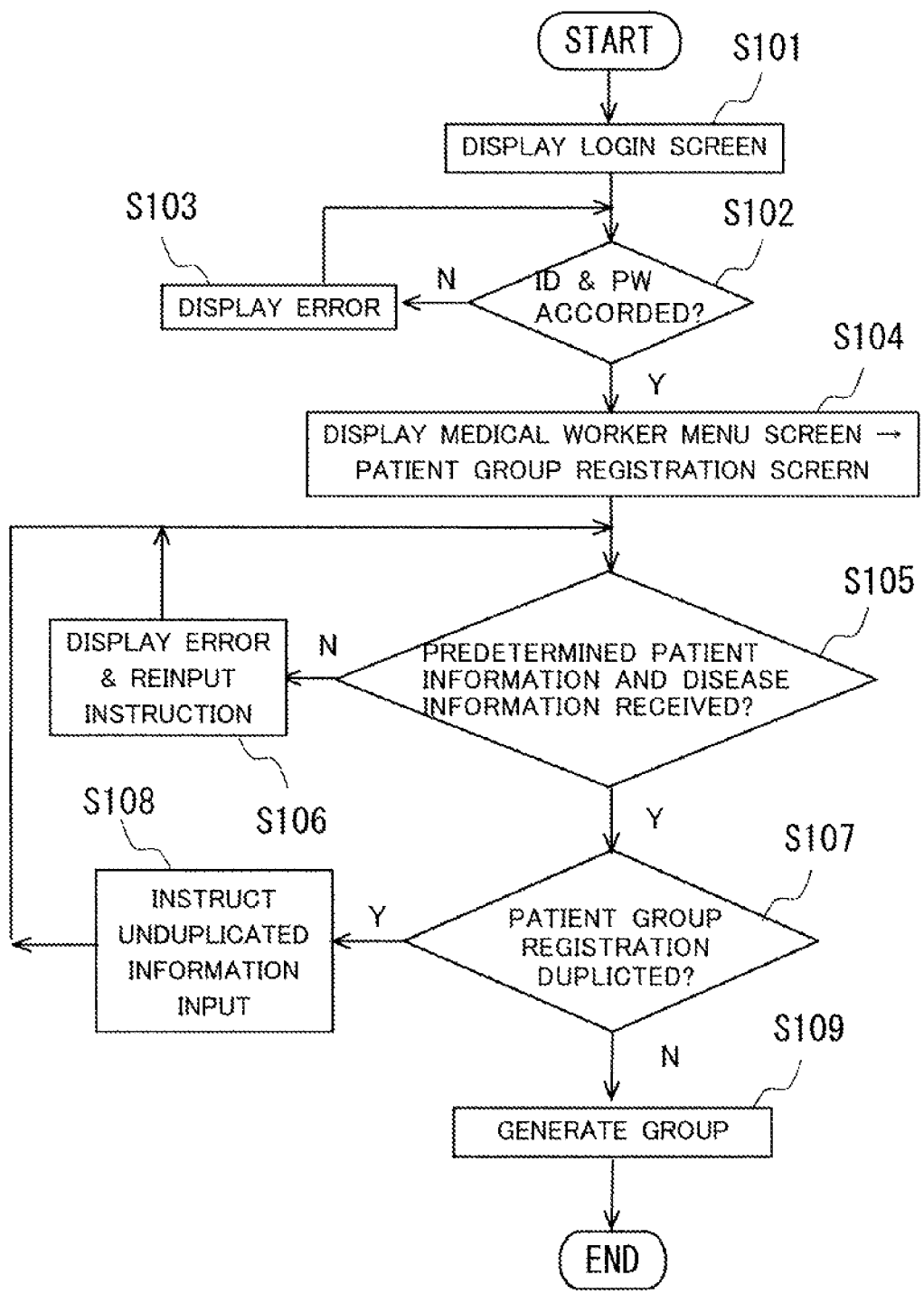
FIG. 29 is a flowchart showing a series of actions for patient group registration by a medical worker used in the medical support system according to the embodiment of the present invention.

FIG. 29 is a flowchart showing a series of actions for patient group registration by a medical worker M in the medical support system 30 according to the present embodiment. The "patient group registration" means that a medical worker M registers the patient P who receives medical treatment from the medical facility F to which the medical worker M belongs, and a disease of the said patient P, in the medical support system 30 to generate a group G.

First, the authentication section 340 of the medical support system 30 displays a prescribed "login screen" (see FIG. 16B) on the medical worker terminal 11 of the medical worker M who has accessed the system 30 and urges to login (step S101), as shown in FIG. 29. In response to this, the medical worker M inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S102). If one or both of the user ID and PW is/are not in accordance with, the authentication section 340 displays the error screen to urge the reinput of them (step S103).

If both of the user ID and PW are in accordance with, the registration subsection 321 of the group management section 320 displays a prescribed "medical worker registration screen" (see FIG. 30) on the medical worker terminal 11. Since the "patient group registration" in the "medical worker menu screen" is selected, the registration subsection 321 displays a prescribed "patient group registration screen" on the medical worker terminal 11 to urge the medical worker M to input prescribed patient information and prescribed disease information (step S105).

As the "patient group registration screen", for example, the screen shown in FIG. 34 is used. In this case, the medical worker M inputs the name of the patient P as the prescribed patient information and the disease name as the prescribed disease information, and thereafter, clicks the "transmission" button. In the case where the medical support system 30 is configured in such a way that "the number of groups to be generated for each patient P in one medical facility F is limited to unity", the registration of a disease is unnecessary.

Subsequently, the registration subsection 321 judges whether or not the information transmitted from the medical worker terminal 11 is in accordance with a predetermined one (step S105). If the information received is not in accordance with the predetermined patient information and the predetermined disease information, for example, in the case where the disease name is not inputted or the patient name is inputted in error, the registration subsection 321 displays the error-reinput screen on the medical worker terminal 11 and urges to reinput the required information (step S106). If the information received is in accordance with the predetermined one, the registration subsection 321 judges whether or not "patient group registration" pertaining to the information received has already been conducted, in other words, whether or not patient group registration is duplicated (step S107). If patient group registration is judged duplicated, input of unduplicated information is instructed (step S108) and the step S105 to S107 are repeated.

In the case where patient group registration is judged unduplicated in the step S107, the registration subsection 321 generates a group and register the same (step S109). Thus, a group G corresponding to the designated disease of the designated patient P is generated in the medical support system 30. At this time, the information about the medical facility F to which the medical worker M who has conducted login belongs (medical facility information) is also registered. Moreover, since the step S107 is provided, there is no anxiety that the same group is generated and registered in duplicate. No participant is included in the group G when it is generated and registered except that default members are registered, which means that the number of the participants in the group G is zero. However, in the case where there are candidates who are wanted to participate in the group G, such as the patient P himself/herself, other medical workers M who belong to the same facility F as that pertaining to the patient group registration, and other medical workers M who belong to other medical facilities F, by transmitting an invitation request to these candidates after receiving permission from both the medical worker-side administrator and the patient-side administrator and then, receiving approval from these candidates in response to the invitation request, group members can be added optionally. The group members other than the patient P will be supporters of the patient P.

Among the medical workers M who have become the group members, the medical information about the designated disease of the patient P pertaining to the group G can be shared under the condition that an agreement is obtained from the said patient P in a written form or the like.

[Supporter Invitation of Existing User]

Next, the operation for inviting the patient P or the medical workers M or the patient-related persons R who has/have already been registered as the user(s), as a supporter(s), by the medical worker M who has conducted the patient group registration in the aforementioned manner will be explained with reference to FIGS. 14A and 14B. This operation is similarly applied to the case where the patient P or the patient-related person R, instead of the medical worker M, conducts the supporter invitation.

Figure 14A:
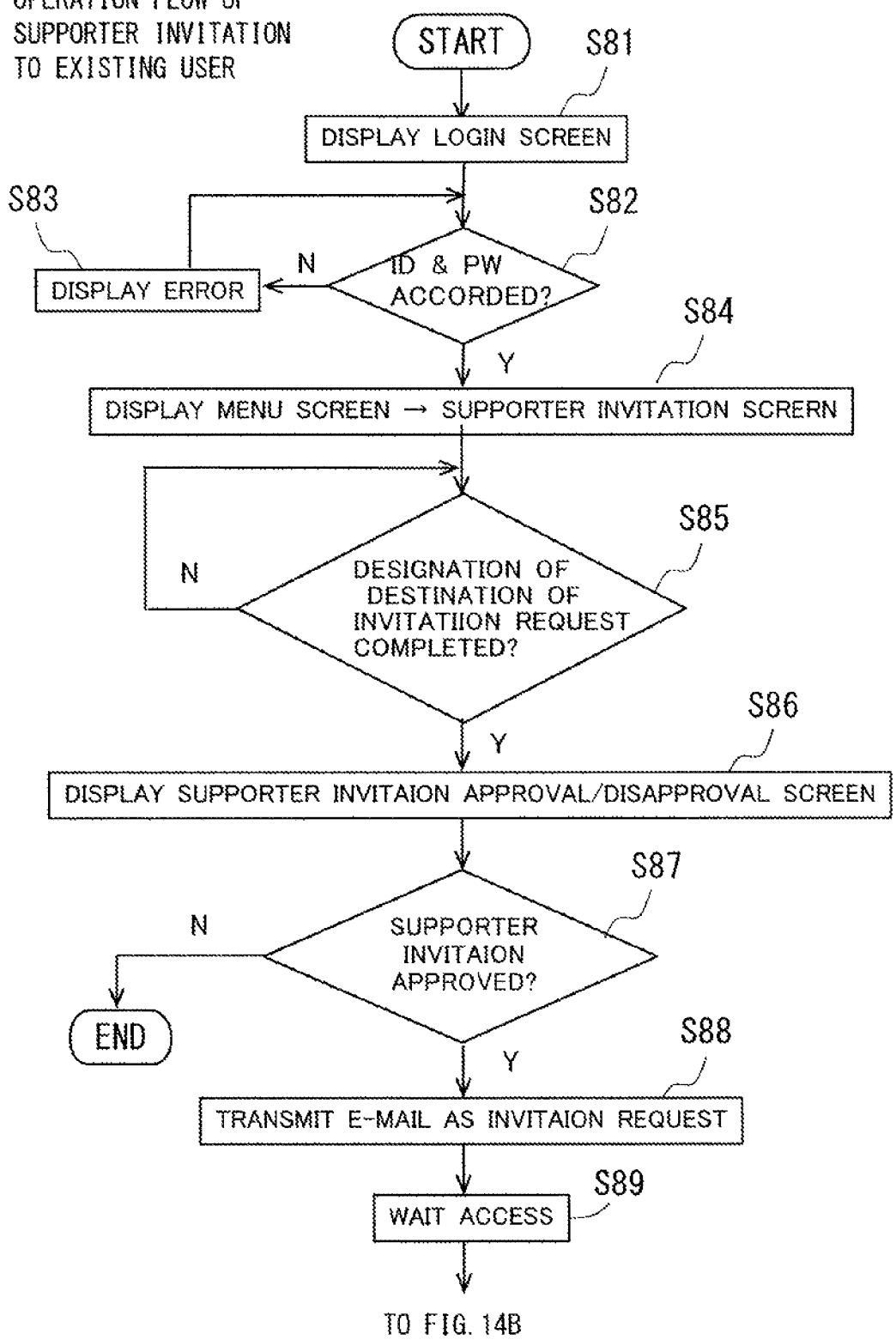
FIG. 14A is a flowchart showing a series of actions for supporter invitation of the existing users by a medical worker or patient in the medical support system according to the embodiment of the present invention.

FIGS. 14A and 14B show a flowchart showing a series of actions for supporter invitation of the existing users in the medical support system according to the present embodiment.

First, as shown in FIG. 14A, the authentication section 340 of the medical support system 30 displays a prescribed "login screen" (see FIG. 16B) on the medical worker terminal 11 of an inviting person (i.e., a medical worker M) who has accessed the system 30 and urges to login (step S81). In response to this, the inviting person inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S82). If one or both of the user ID and PW is/are not in accordance with, the authentication section 340 displays the error screen to urge the reinput of them (step S83).

If both of the user ID and PW are in accordance with, the registration subsection 311 of the user management section 311 displays a prescribed "medical worker menu screen" to urge the inviting person to select a desired function. As the "medical worker menu screen", a screen shown in FIG. 30 is used. Here, a supporter is newly invited and thus, the inviting person selects "invitation to group". In response to this, the invitation request control subsection 331 of the group management section 330 displays a prescribed "supporter invitation screen" on the terminal 11 of the inviting person and urges the same inviting person to designate the destinations of an invitation request (step S84). Since the persons to be invited as supporters (invited persons) have already been registered as the users, the names of the users who are selectable as the invited persons are displayed on the "supporter invitation screen" in the form of list. Therefore, it is sufficient for the inviting person to select desired persons from the list.

As the "supporter invitation screen" in the step S84, for example, the screen shown in FIG. 23 may be used. In this case, the names of the users who are selectable as the invited persons are displayed on the "supporter invitation screen" in the form of list. The inviting person can select and designate the desired invited persons by clicking the "invite" buttons attached to the respective names in this list.

The invitation request control subsection 331 judges whether or not the invited persons have been completed (step S85). If the designation of the invited persons is judged completed, the invitation request control subsection 331 displays the "supporter invitation approval/disapproval screen" on the medical worker-side administrator terminal and the patient-side administrator terminal and asks for permission of the transmission of the invitation request (step S86). Thereafter, the section 331 judges whether or not a reply of "permitted" has been received from each of the medical worker-side administrator terminal and the patient-side administrator terminal (step S87). If a reply of "permitted" has not been received from each of the medical worker-side administrator terminal and the patient-side administrator terminal, the supporter invitation process is completed without transmission of the e-mail as the invitation request.

As the "supporter invitation approval/disapproval screen" in the step S86, for example, the screen shown in FIG. 24 may be used. In this case, when the supporter invitation is to be permitted, each of the administrators clicks the "permit" button. When the supporter invitation is not to be permitted, each of the administrators clicks the "not permit" button.

If a reply of "permitted" has been received from each of the medical worker-side administrator terminal and the patient-side administrator terminal, the invitation request control subsection 331 transmits the e-mail as the invitation request to the designated destinations (step S88), and waits the access from the invited persons (the arrival of replies) (step S89).

If the access from the invited persons is found, the invitation request control subsection 331 displays a predetermined "supporter invitation approval screen" on the terminals of the invited persons (step S90), and judges whether or not each invited person has approved the invitation request (step S91).

In the case where the invited person has refused the invitation request, the invitation request control subsection 331 displays a screen notifying that participation to the group has been refused on the terminal of the inviting person (step S92) and completes the supporter invitation process. In the case where the invited person has approved the invitation request, the invitation request control subsection 331 adds the said invited person to the group as a supporter (step S93), and displays a screen notifying that the said invited person has been added to the group as a supporter on the terminal of the invited person (step S94), and thereafter, completes the supporter invitation process.

Figure 25:
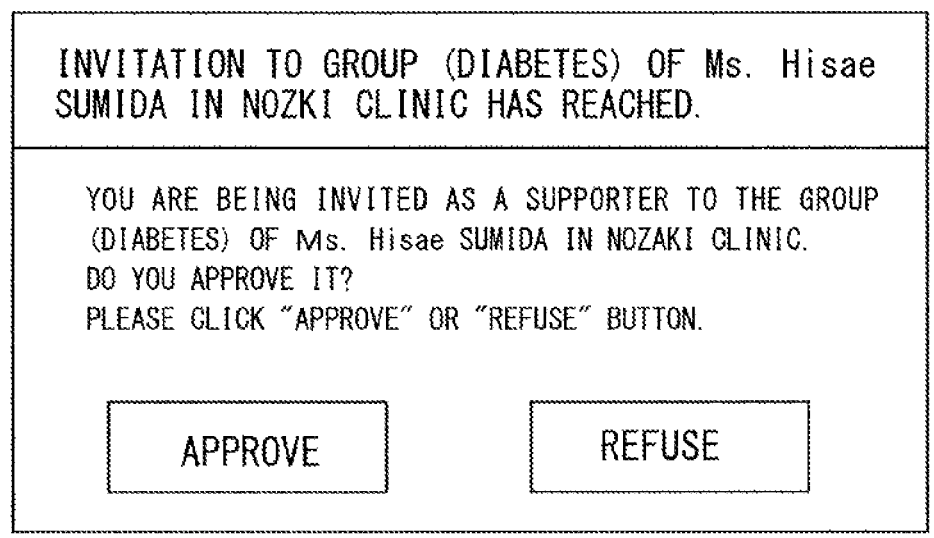
FIG. 25 is an explanatory diagram showing an example of a "supporter invitation permission screen" in the case of inviting an existing user used in the medical support system according to the embodiment of the present invention.

As the "invitation request approval screen" in the step S90, for example, the screen shown in FIG. 25 may be used. In this case, the invited person can approve the invitation request by simply clicking the "approve" button on this screen. In the case of refusing the invitation request, it is sufficient for the invited person to click the "refuse" button.

[Supporter Invitation for Non-User by Medical Worker/Patient]

Next, the operation in the case where the medical worker M who has conducted the patient group registration in the aforementioned manner invites as a supporter a patient P or a medical worker M or a patient-related person who is not yet registered as a user of this medical support service will be explained with reference to FIGS. 15A and 15B. This operation is similarly applied to the case where a patient P or a patient-related person R conducts the supporter invitation, instead of the medical worker M.

Figure 15A:
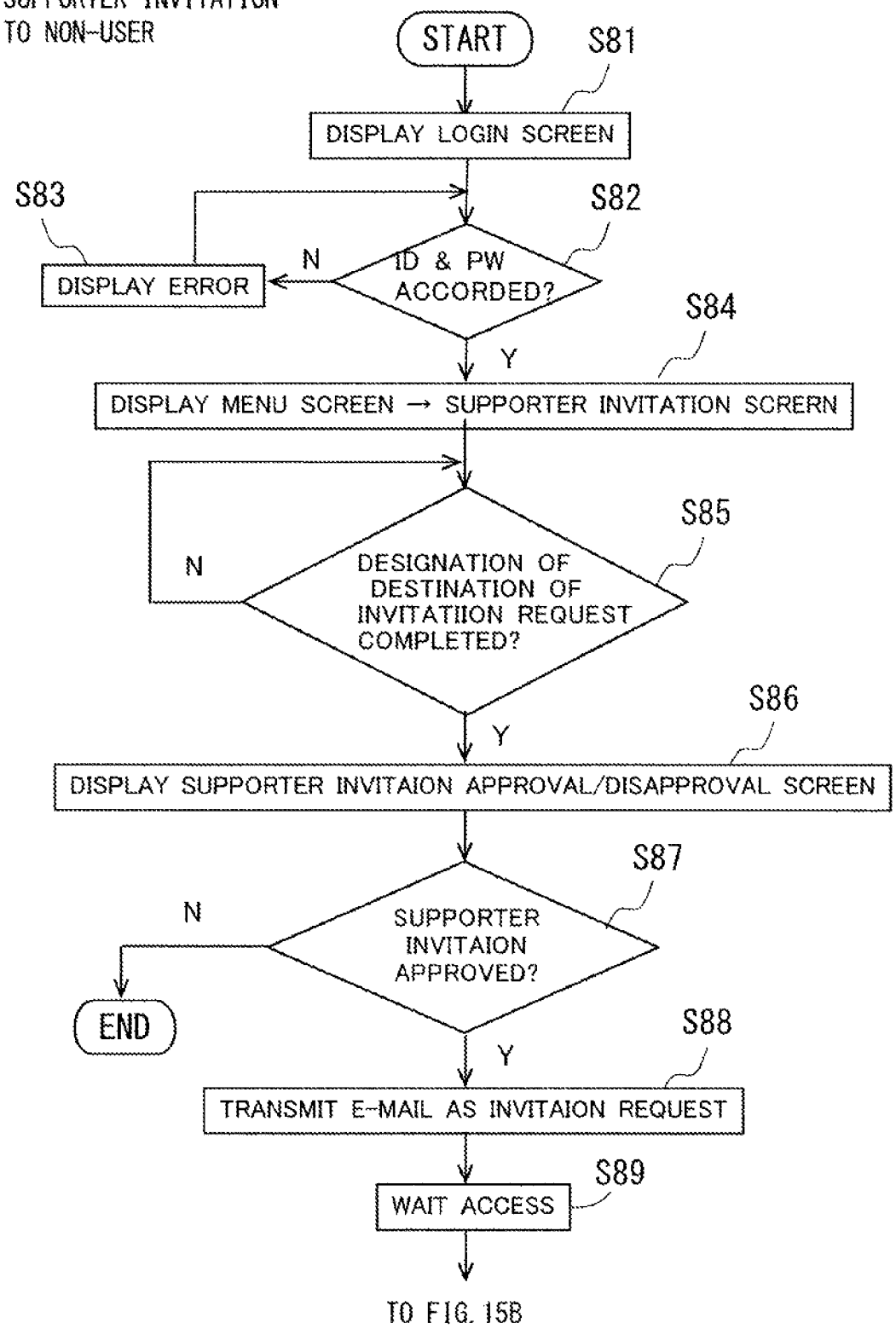
FIG. 15A is a flowchart showing a series of actions for supporter invitation of non-users by a medical worker or patient in the medical support system according to the embodiment of the present invention.

FIGS. 15A and 15B show a flowchart showing a series of actions for supporter invitation of the non-users in the medical support system 30 according to the present embodiment.

The operation for supporter invitation of the non-users is different from that for supporter invitation of the existing users described above in that the name and destination (e-mail address) of an invited person to whom an invitation request is transmitted are individually designated and that the new user registration process is conducted before displaying the "invitation request approval screen" on the terminal 11 of the inviting person (medical worker M).

Specifically, as shown in FIG. 15A, the authentication section 340 of the medical support system 30 carries out from the step S81 of displaying the prescribed "login screen" on the terminal 11 of the inviting person (i.e., the medical worker M) who has accessed the system 30 to the step S83 of judging whether or not the user ID and PW are in accordance with the registered ones. If both of the user ID and PW are in accordance with, the registration subsection 311 of the user management section 310 displays the "medical worker menu screen" to urge the inviting person to select a desired function.

As the "medical worker menu screen", a screen shown in FIG. 30 is used. Here, a supporter is newly invited and thus, the inviting person selects "invitation to group". In response to this, the invitation request control subsection 331 of the group management section 330 displays a prescribed "supporter invitation screen" on the terminal 11 of the inviting person and urges the same inviting person to designate the destinations of an invitation request (step S84). Since the persons to be invited as supporters (invited persons) have not yet been registered as the users, the destinations of the invitation request need to be designated individually.

As the "supporter invitation screen" in the step 84, a screen having the form of FIG. 26 may be used. In this case, the e-mail address and passphrase of the one to be designated as an invited person need to be inputted individually. In addition, only one set of the fields for the e-mail address and passphrase is provided in the example of FIG. 26; however, it is needless to say that a plurality of sets of the fields for the e-mail address and passphrase may be provided. If so, the e-mail address and passphrase of a plurality of invited persons can be inputted in a lump on the same screen. When the input is completed, the invitation request can be transmitted to the invited person by simply clicking the "invite" button.

The invitation request control subsection 331 judges whether or not the designation of the destinations of an invitation request has been completed (step S85). If the designation of the designations is judged completed, the invitation request control subsection 331 displays the "supporter invitation approval/disapproval screen" on the medical worker-side administrator terminal and the patient-side administrator terminal and then, asks for permission of the transmission of the invitation request (step S86). Thereafter, the section 331 judges whether or not a reply of "permitted" has been received from each of the medical worker-side administrator terminal and the patient-side administrator terminal (step S87). If a reply of "permitted" has not been received from each of the medical worker-side administrator terminal and the patient-side administrator terminal, the e-mail as the invitation request will not be transmitted and the supporter invitation process is completed. If a reply of "permitted" has been received from each of the medical worker-side administrator terminal and the patient-side administrator terminal, the invitation request control subsection 331 transmits the e-mail as the invitation request to the designated e-mail addresses (step S88), and waits the access from the invited persons (step S89). When the access from the invited persons is found, the invitation request control subsection 331 displays the prescribed "new user registration screen" on the terminals of the invited persons before displaying the predetermined "invitation request approval screen". Then, the subsection 331 conducts the user registration of the medical support system 30 for the invited persons and subsequently, urges the invited persons to approve the invitation request (step S95).

When the invited persons carry out the new user registration process and they are registered as the users of the medical support system 30, the invitation request control subsection 331 displays the predetermined "invitation request approval screen" on the terminals of the invited persons (step S90) and then, judges whether or not the invited persons have approved the invitation request (step S91).

In the case where the invited person has refused the invitation request, the invitation request control subsection 331 displays a screen notifying that participation to the group has been refused on the terminal of the inviting person (step S92), and completes the supporter invitation process.

In the case where the invited person has approved the invitation request, the supporter invitation is permitted and therefore, the invitation request control subsection 331 adds the invited person who has permitted the invitation to the group G as a supporter; as a result, the said invited person becomes one of the group members (step S93). Then, the subsection 331 displays a screen notifying that a supporter has been add to the group on the terminal of the invited person (step S94) and completes the supporter invitation process.

As the "invitation request approval screen" in the step S90, for example, the screen having a form shown in FIG. 27 may be used. In this case, when the invited person approves the invitation request, it is sufficient for the said invited person to simply click the "approve" button after inputting his/her name and e-mail address. When refusing the invitation request, it is sufficient for the invited person not to reply the invitation request (e-mail) and to ignore the same.

As the "supporter invitation approval/disapproval screen" in the step S86, for example, the screen having the form shown in FIG. 28 may be used. In this case, when the medical worker-side administrator or the patient-side administrator approves the supporter invitation, it is sufficient to simply click the "approve" button. When refusing the supporter invitation, it is sufficient to click the "not approve" button.

[Personalization Registration by Medical Worker]

Figure 12A:
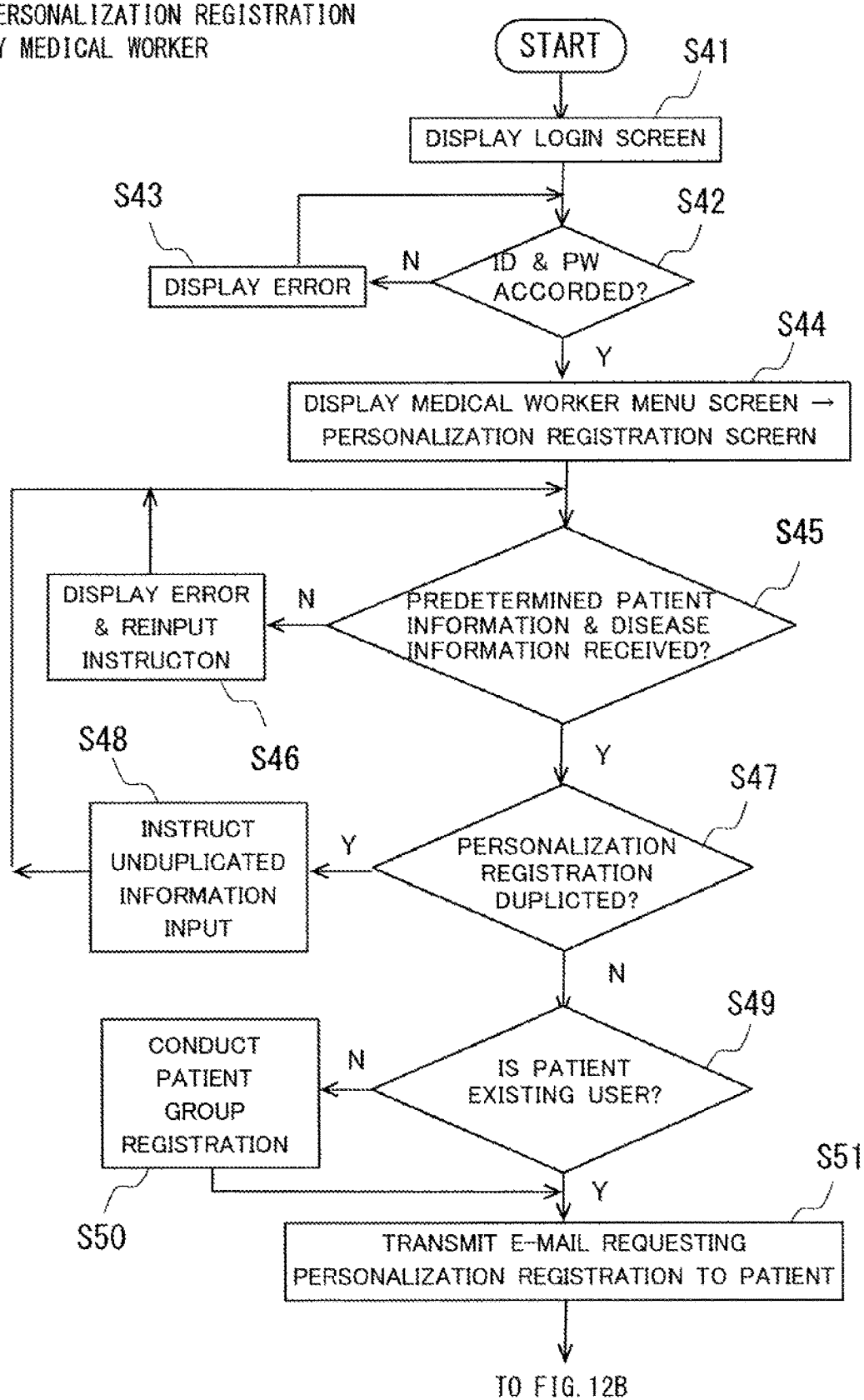
FIG. 12A is a flowchart showing a series of actions for personalization registration by a medical worker in the medical support system according to the embodiment of the present invention.
Figure 12B:
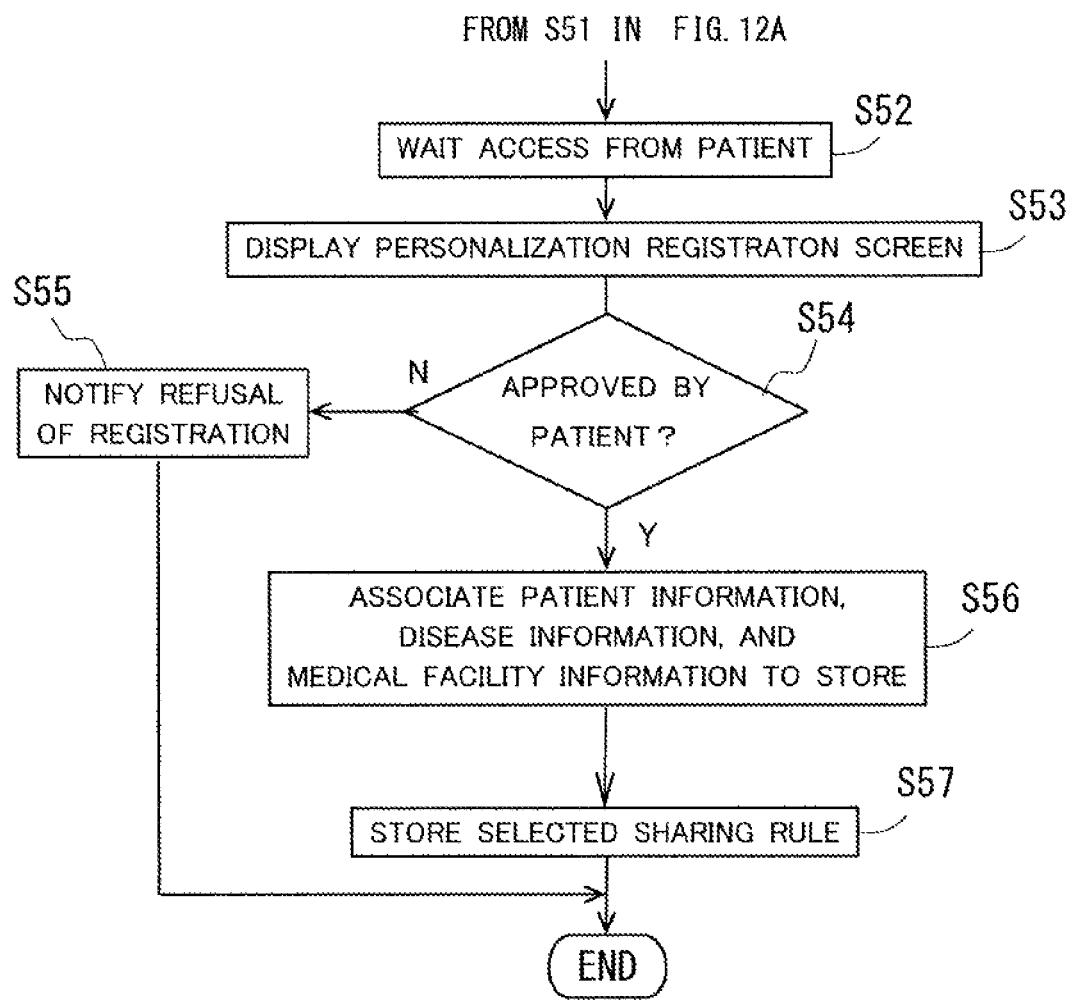
FIG. 12B is a flowchart showing the series of actions for personalization registration by a medical worker in the medical support system according to the embodiment of the present invention, which is subsequent to FIG. 12A.

Next, personalization registration by a medical worker will be explained with reference to FIGS. 12A and 12B. FIGS. 12A and 12B show a flowchart showing a series of actions for personalization registration by a medical worker in the medical support system 30 according to the present embodiment.

First, the authentication section 340 of the medical support system 30 displays the prescribed "login screen" on the medical worker terminal 11 of a medical worker M who has accessed the system 30 and urges to login, as shown in FIG.

12A (step S41). In response to this, the medical worker M inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S42). If one or both of the user ID and PW is/are not in accordance with, the authentication section 340 displays the error screen to urge the reinput of them (step S43).

If both of the user ID and PW are in accordance with, the registration subsection 311 of the user management section 310 displays a prescribed menu screen (see FIG. 30) to urge the said medical worker M to select a desired one of the functions. Here, personalization registration is newly conducted and thus, the said medical worker M selects "personalization registration request". Then, in response to this, the registration subsection 321 of the group management section 320 displays a prescribed "personalization registration request screen" on the medical worker terminal 11 and urges to input and transmit predetermined patient information (step S44).

As the "personalization registration request screen" in the step S44, for example, the screen having the form shown in in FIG. 18 may be used. In this case, the medical worker M inputs the e-mail address of a patient P and thereafter, clicks the transmission button. In this case, the following configuration may be taken. Specifically, the names of the patients P who can be personalization-registered are displayed in the form of list on the medical worker terminal 11 in such a way that the medical worker can select a desired patient P by clicking the name of the desired one of the patients P.

Next, the registration subsection 321 of the group management section 320 judges whether or not the information transmitted from the medical worker terminal 11 is in accordance with a predetermined one (step S45). If the information received is not in accordance with the predetermined one, for example, in the case where the e-mail address is not inputted in the correct notation, the registration subsection 321 displays the error-reinput screen on the medical worker terminal 11 and urges to reinput the information (step S46). If the information received is in accordance with the predetermined one, the registration subsection 321 judges whether or not "personalization registration" pertaining to the information received has already been conducted, in other words, whether or not "personalization registration" is duplicated (step S47). If personalization registration is judged duplicated, the registration subsection 321 instructs the medical worker M to input unduplicated information (step S48) and thereafter, repeats the step S45 to S47.

In the case where personalization registration is judged unduplicated in the step S47, the flow advances to the step S49 and the registration subsection 321 judges whether or not the patient P pertaining to personalization registration, in other words, the patient P who has been designated on the "personalization registration request screen" is an existing user of the medical support system 30. This is because there is a case where the patient P pertaining to personalization registration has not yet been a user of the medical support system 30. If the said patient P is judged not an existing user, the registration subsection 321 conducts the aforementioned patient group registration process (step S50). When the patient group registration process is completed in this way, the registration subsection 321 transmits an e-mail notifying that the "personalization registration request" is being made to the e-mail address of the patient P pertaining to the personalization registration (step S51). Since this e-mail includes the URL which is linked with the "personalization registration approval screen", the "personalization registration approval screen" can be opened on the patient terminal 10 by clicking the said URL by the patient P.

Next, the registration subsection 321 waits the access from the patient P pertaining to the personalization registration (step S52). When the access from the patient terminal 10 is found, the registration subsection 321 displays the predetermined "personalization registration approval screen" (step S53). Then, the registration subsection 321 judges whether or not the personalization registration has been approved (step S54). If the personalization registration is judged approved, the registration subsection 321 associates the patient information, the disease information, and the medical facility information which pertain to the personalization registration with each other and then, stores these associated information in the personalized facility information storage subsection 328 (step S56) and at the same time, stored the sharing rule selected by the patient P in the sharing agreement information storage subsection 329 (step S57); the subsection 321 complete the personalization registration process in this way. If the personalization registration is judged disapproved in the step S54, the registration subsection 321 notifies the medical worker terminal 11 that the personalization registration has been refused and completes the personalization registration process.

As the "personalization registration approval screen" in the step S53, for example, the screen having the form of FIG. 19 may be used. In this case, when approving the registration, the patient P inputs his/her passcode and then, selects "Rule 1 (share in facility)", "Rule 2 (share comprehensively) ", or "Rule 3 (refuse sharing)" and clicks the approve registration button. When disapproving the registration, it is sufficient for the patient P to input his/her passcode and to click the disapprove registration button. In the case of disapproving the registration, selection of the information sharing rules is unnecessary.

[Personalization Registration by Patient]

Figure 13B:
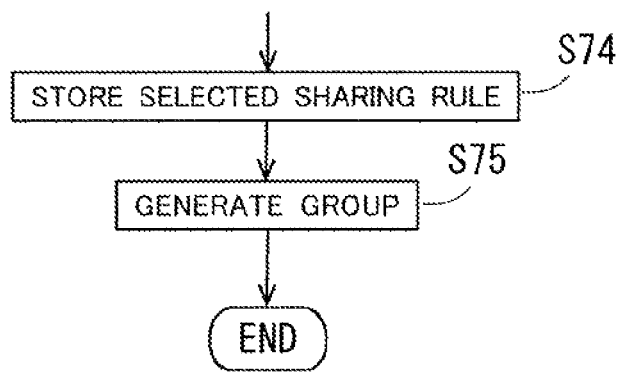
FIG. 13B is a flowchart showing the series of actions for personalization registration by a patient in the medical support system according to the embodiment of the present invention, which is subsequent to FIG. 13A.

Next, personalization registration by a patient P will be explained with reference to FIGS. 13A and 13B. FIGS. 13A and 13B show a flowchart showing a series of actions for personalization registration by a patient in the medical support system 30 according to the present embodiment.

First, the authentication section 340 of the medical support system 30 displays the prescribed "login screen" on the patient terminal 10 of a patient P who has accessed the system 30 and urges to login, as shown in FIG. 13A (step S61). In response to this, the patient P inputs his/her user ID and PW on the "login screen" and clicks the transmission button displayed on the same screen. The authentication section 340 judges whether or not the user ID and PW thus received are in accordance with the user ID and PW which have been registered in the user information storage subsection 312 of the user management section 310 (step S62). If one or both of the user ID and PW is/are not in accordance with, which means that the patient P has not yet been a user of the medical support system, the authentication section 340 displays the error screen (step S63) and conducts the new user registration process (step S64). The patient P conducts the new user registration process and the flow is returned to the step S61. Thereafter, the patient P inputs his/her user ID and PW on the displayed "login screen" and clicks the transmission button on the same screen.

If both of the user ID and PW are in accordance with, the registration subsection 311 of the user management section 310 displays a "menu screen" (see FIG. 31) to urge the patient P to select a desired one of the functions. Here, personalization registration is newly conducted and thus, the patient P selects "personalization registration request". Then, in response to this, the registration subsection 321 of the group management section 320 displays the prescribed "personalization registration request screen" on the patient terminal 10 and urges to retrieve and designate a medical facility which the patient P wants to conduct personal registration (step S65). Furthermore, the registration subsection 321 displays the prescribed "sharing rule selection screen" on the patient terminal 10 and to urge to select one of the sharing rules (step S66).

As the "personalization registration request screen" in the step S65, for example, the screen having the form shown in in FIG. 20 may be used. In this case, the system is configured in such a way that the patient P can retrieve and select a medical facility which the patient P wants to conduct personalization registration. An example of displaying the result of retrieval is shown in FIG. 21. In the example of FIG. 21, the patient P can designate a desired one from the medical facilities displayed in the form of list by simply clicking the "personalization registration" button displayed in the facility name field of the desired facility.

As the "sharing rule selection screen" in the step S66, for example, the "personalization registration confirmation screen" having the form of FIG. 22 may be used. In this case, when confirming the personalization registration, the patient P inputs his/her passcode and selects "Rule 1 (share in facility)", "Rule 2 (share comprehensively)", or "Rule 3 (refuse sharing)" from the pulled down list displayed in the field of the information sharing rule; thereafter, the patient P clicks the registration button. When discontinuing the personalization registration, it is sufficient for the patient P to simply click the cancel button. In the case of cancelling, input of the passcode and selection of the information sharing rules are unnecessary.

Then, the registration subsection 321 judges whether or not all the required information is transmitted from the patient terminal 10 (step S67). If all the required information is not received, for example, in the case where the disease name is not received, the registration subsection 321 displays the error-reinput screen on the patient terminal 10 and urges to reinput the information (step S68). If all the required information is received, the registration subsection 321 judges whether or not "personalization registration" pertaining to the information received has already been conducted, in other words, whether or not "personalization registration" is duplicated (step S69). If personalization registration is judged duplicated, the registration subsection 321 instructs the patient P to input unduplicated information (step S70) and thereafter, repeats the step S65 to S69.

In the case where personalization registration is judged unduplicated in the step S69, the flow advances to the step S71 and the registration subsection 321 judges whether or not the patient P who has requested personalization registration is registered as a patient in the medical facility F pertaining to the personalization registration, in other words, whether or not the patient P is included as a patient in the medical facility F which has been designated in the "personalization registration request screen". This is because there is a case where the said patient P has not yet been a patient of the medical facility F pertaining to personalization registration. If the said patient P is judged registered as a patient in the said medical facility F, the registration subsection 321 associates the patient information, the disease information, and the medical facility information which pertain to the personalization registration with each other and stores these associated information in the personalized facility information storage subsection 328 (step S73) and at the same time, stores the sharing rule selected by the patient P in the sharing agreement information storage subsection 329 (step S74), thereby registering and generating a group G (step S75). The personalization registration process is completed in this way.

As explained above, a group G for a designated disease of a designated patient P is generated by personalization registration by the patient P also. The number of initial group members of the group G thus generated is zero except that default members are registered. Moreover, in the case where candidates who are wanted to participate in the group G exists in the patient P himself/herself who has conducted the personalization registration, the medical workers M who belong to the medical facility F pertaining to the personalization registration, medical workers M who belong to other medical facilities F, or the patient-related persons R, the candidates can be optionally added to the group G as the group members by transmitting an invitation request to these candidates after receiving permission from both the medical worker-side administrator and the patient-side administrator and by receiving approval from these candidates in response to the invitation request. All the group members other than the patient P will become supporters of the patient P.

In the group G formed by the personal registration by the patient P, the medical information about the designated disease of the patient P pertaining to the group G can be shared among the medical workers M who have become the group members according to the sharing rule which the patient P has agreed. Therefore, the medical service to be provided to the patient P can be improved.

Figure 32:
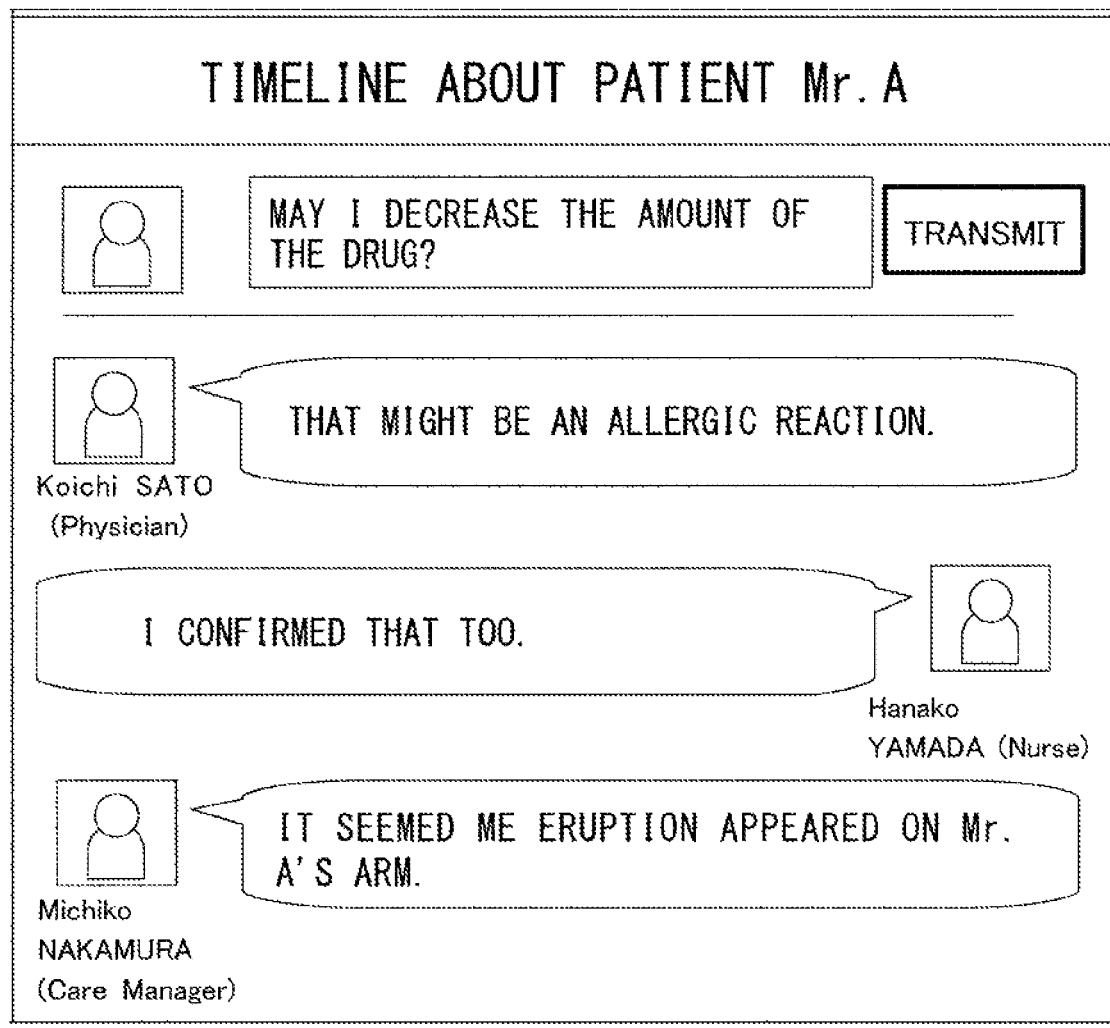
FIG. 32 is an explanatory diagram showing an example of a timeline about the patient A used in the medical support system according to the embodiment of the present invention.

An example of the timeline for the group G pertaining to the patient, Mr. A, is shown in FIG. 32. In this example, in response to an inquiry (message) from Mr. A, a reply (message) from Koichi SATO as a medical worker (physician), a reply (message) from Hanako YAMADA as a medical worker (nurse), and a reply (message) from Michiko NAKAMURA as a medical worker (care manager) are arranged in chronological order and therefore, the flow of the story in these messages can be easily grasped and the content of the story can be understood very easily. Since anyone of the members of this group G is accessible to the timeline, it is easy to view the messages in the timeline and to contribute messages to the timeline. Accordingly, communication is conducted smoothly and mutual understanding is acquired easily in this group G of Mr. A.

An example of the integrated medical information of Mr. A is shown in FIG. 33. As seen from this example, the medical information about diabetes which is accumulated and stored in the clinic X and the medical information about lung cancer which is accumulated and stored in the clinic Y are viewable in an integrated or combined state. For this reason, both of the medical workers M who belong to the clinic X and those who belong to the clinic Y can share the medical information of Mr. A about the different diseases. Therefore, the medical workers M who belong to the clinic X can make medical treatments taking the medical information in the clinic Y into consideration. The medical workers M who belong to the clinic Y also can make medical treatments taking the medical information in the clinic X into consideration. As a result, there is an advantage that more suitable medical treatments can be applied in accordance with the symptoms of a patient.

With the medical/care support system 30 according to the embodiment of the present invention, as explained above, the disease ID (disease identification information) is assigned to the disease of the patient P as the user to store the same by the disease information storage subsection 316 (disease identification information storage means), and the patient ID (service recipient identification information) is associated with the disease ID of the patient P corresponding to the said patient ID to thereby generate the group G having the unique group ID (group identification information) by the group management section 320 (group management means). Thus, the group G is generated for each disease of the patient P. Therefore, by adding the medical workers M who provide medical service for the disease pertaining to the group G to the group G as the group members thereof using the invitation request control subsection 324 and the invitation request information storage subsection 324 (invitation request management means), the medical workers M thus added can share the medical information about the disease of the group G which pertains to the patient P has by way of the user terminals 10, 11, or 12.

Accordingly, the medical information of each patient P can be shared while protecting the privacy of the patient P and at the same time, better-quality medical service can be provided to the patient P pertaining to the group G based on the medical information thus shared.

Moreover, in response to the sending of the invitation request which includes designation of the inviting person and the invited person and which is performed using the user terminal 10, 11, or 12, the invited person as the user is added to the group G as the group member thereof by the invitation request control subsection 324 and the invitation request information storage subsection 325 under the condition that the invitation request is approved by the invited person using the user terminal 10, 11, or 12 and that permission is obtained by the predetermined administrators using the user terminal 10, 11, or 12. Therefore, there arises no anxiety that someone is added to the group G as the group member without being contrary to the intention of the invited person and/or that of the administrators (e.g., the director of a hospital) and there arises no problem in the medical service for the patient P due to addition of the invited person as the group member to the group G.

In addition, the medical support method according to the present invention is carried out in the aforementioned medical support system 30. The medical support program according to the present invention is a program which is installed in a computer to realize the aforementioned medical support system 30.

[Variations]

The aforementioned embodiment is an embodied example of the present invention. Therefore, it is needless to say that the present invention is not limited to this embodiment and that a variety of modifications are possible without departing from the spirit of the invention.

For example, in the aforementioned embodiment, the groups G11, G12, and G13 are generated for the three diseases (here, diabetes, hyperlipemia, and gout) of the patient P1, and different medical facilities F (clinic F1, clinic F2, and hospital F3) are personalization-registered to each of the groups G11, G12, and G13 in such a way as to be in charge of the respective medical treatments. Moreover, the groups G21 and G22 are generated for the two diseases (here, Alzheimer's disease and hypertension) of the patient P2, and different medical facilities F (hospital F3 and home-visit nursing station F4) are personalization-registered to each of the groups G21 and G22 in such a way as to be in charge of the respective medical treatments. This means that different medical facilities F are in charge of medical treatments for the respective diseases of each patient P in the aforementioned embodiment. However, the present invention is not limited to this mode. The same medical facility F may be in charge of medical treatments for a plurality of diseases of each patient P. Concretely speaking, for example, the clinic F1 may be personalization-registered in common to both of the groups G11 and G12 generated for the two diseases (here, diabetes and hyperlipemia) of the patient P1. In this case, for example, the medical worker M1 or M2 who belongs to the clinic F1 is in charge of the medical service for the two diseases (here, diabetes and hyperlipemia).

Moreover, a medical facility F may be in correspondence to each patient P without considering the disease(s) of a patient P. In other words, a patient P and a medical facility F may have a one-to-one correspondence, and a plurality of medical facilities F may be in correspondence to each patient P.

Although the present invention is embodied as a medical support system that provides medical service in the aforementioned embodiment, the present invention is not limited to this. The present invention may be applied to a long-term care support service to be embodied as a care support system, or may be embodied as a medical and care support system that provides both of medical support service and care support service.

INDUSTRIAL APPLICABILITY

The present invention is applicable to the fields necessitating the cooperation of medical workers and/or care workers, concretely speaking, the fields necessitating the provision of better-quality medical service or care service through the cooperation of medical workers and/or care workers who belong to various occupation categories such as physicians, nurses, nutritionists, and care managers whose special fields are different from each other.

DESCRIPTION OF REFERENCE NUMERALS 10 patient terminal
11 medical worker terminal
12 patient-related person terminal
20 Internet
30 medical support system
51 timeline
51a all member sharing area
51b medical worker sharing area
310 user management section
311 registration section
312 user information storage section
313 patient information storage section
314 medical worker information storage section
315 medical-related facility information storage section
316 disease information storage section
320 personalization registration management section
321 registration section
322 personalized facility information storage section
323 sharing agreement information storage section
324 patient reality verification section
330 group management section
331 invitation request control section
332 invitation request information storage section
333 group information storage section
334 group member information storage section
335 timeline control section
336 message control section
337 authentication section 340 authentication section
350 communication control section
F medical facility
F1 clinic
F2 clinic
F3 hospital
F4 home-visit nursing station
G group
G11 diabetes-curing group of patient P1
G12 hyperlipemia-curing group of patient P1
G13 gout-curing group of patient P1
G21 Alzheimer's disease-curing group of patient P2
G22 hypertension-curing group of patient P2
M medical worker
M1, M2, M3, M4, M5, M6, M7, M8 medical worker
P patient
P1, P2 patient
R patient-related person
R1, R2, R3, R4, R5, R6, R7, R8 patient-related person

The invention claimed is:

1. A medical/care support method for supporting provision of medical/care service by making medical/care information about specific patients or care-needing persons viewable on user terminals by way of a network in response to requests from the user terminals using a medical/care support system, wherein the medical/care support system comprises a user management section and a group management section, the method comprises:

assigning user identification information to respective users utilizing the medical/care service by way of the user terminals to store the user identification information using the user management section;

assigning service recipient identification information to respective patients or care-needing persons as the users to store the service recipient identification information so as to be associated with the user identification information of the patients or care-needing persons using the user management section;

assigning service worker identification information to respective medical workers or care workers as the users to store the service worker identification information so as to be associated with the user identification information of the medical workers or care workers using the user management section;

assigning service-related facility identification information to respective service-related facilities to which the medical workers or care workers belong to store the service-related facility identification information so as to be associated with the service worker identification information of the medical workers or care workers using the user management section;

generating groups, each of which has a unique group identification information, to store the group identification information so as to be associated with the service recipient identification information of the patients or care-needing persons using the group management section; and adding, in response to sending of an invitation request which includes designation of an inviting person and an invited person who is designated from the users and which is performed using one of the user terminals, the invited person to a designated one of the groups as its group member, under a condition that the invitation request is approved by the invited person using one of the user terminals and that permission is obtained by at least one of a predetermined medical worker/care worker-side administrator and a predetermined patient/care-needing person-side administrator using one of the user terminals;

wherein each of the groups is associated with a designated one of the patients or care-needing persons and a designated one of one or more diseases of the designated patient or care-needing person by associating the group identification information of the said group with the service recipient identification information of the designated patient or care-needing person and with the disease identification information of the designated disease of the designated patient or care-needing person;

wherein when each of the groups includes the medical workers and/or care workers as its group members, the medical/care information of the designated patient or care-needing person about the designated disease thereof that corresponds to the said group is viewable to the medical workers and/or care workers as the group members of the said group on their user terminals by way of the network for sharing the said medical/care information, in which the medical/care information shared among the medical workers and/or care workers as the group members of the said group is displayed on their user terminals as a timeline which is generated for the said group, and the group members of the said group can contribute and view messages in the timeline;

wherein when the medical/care information shared among the medical workers and/or care workers as the group members of each of the groups is displayed on their user terminals, a part of the shared medical/care information is displayed in such a way that all the group members of the said group can view and a remainder of the shared medical/care information is displayed in such a way that only the medical workers and/or care workers as the group members of the said group can view;

wherein a number of the groups having the same service recipient identification information, which have different disease identification information, is n (n is an integer equal to 2 or greater), and the group identification information of each of the n groups is associated with the service-related facility identification information of one or more of the service-related facilities to which the medical workers and/or care workers as the group members of a corresponding one of the n groups belong; and wherein the medical/care information of the n groups having the same service recipient identification information, which is distributed among the service-related facilities to which the medical workers and/or care workers as the group members of the n groups belong, is sharable among the group members of the n groups while protecting privacy of the patient or care-needing person corresponding to the said n groups, and is viewable in a combined form to the group members of the said n groups by way of the user terminals of the group members of the n groups using different sharing rules to enable medical workers and/or care workers as the group members of the said n groups to use the medical/care information of the said n groups, which provides improved medical/care service to the patient or care-needing person corresponding to the said n groups.

2. The medical/care support method according to claim 1, wherein when a personalization registration request which has been sent by way of one of the user terminals is received, the service recipient identification information designated by the personalization registration request and the service-related facility identification information designated by the personalization registration request are stored so as to be associated with each other; and personalized facility information for the patient or care-needing person corresponding to the designated service recipient identification information is generated by associating the designated service recipient identification information and the designated service-related facility identification information with each other.

3. The medical/care support method according to claim 2, wherein whether or not the personalization registration request is approved is inquired to the patient or care-needing person corresponding to the service recipient identification information designated by the personalization registration request while encouraging selection of a sharing rule for the medical/care information of the patient or care-needing person; and when the personalization registration request is approved by the patient or care-needing person, the sharing rule selected is stored.

4. The medical/care support method according to claim 2, wherein identity verification for approving the personalization registration request by the patient or care-needing person corresponding to the service recipient identification information designated by the personalization registration request is performed using a passcode which is generated based on a service recipient number or an insured person number used in the service-related facility corresponding to the service-related facility identification information designated by the personalization registration request.

5. The medical/care support method according to claim 1, wherein identity verification of the user designated in the invitation request as the invited person is performed using a telephone number or a passphrase of the user designated in the invitation request as the invited person.

6. The medical/care support method according to claim 2, wherein when the patient or care-needing person corresponding to the service recipient identification information designated by the personalization registration request approves the personalization registration request, a short-distance wireless communication terminal in which a terminal number and Uniform Resource Locator (URL) information assigned to the service-related facility corresponding to the service-related facility identification information designated by the personalization registration request have been stored is used; and the URL information is transmitted to the user terminal for the patient or care-needing person corresponding to the designated service recipient identification information by contacting the short-distance wireless communication terminal with the user terminal, thereby displaying a personalization registration approval screen on the user terminal.

7. The medical/care support method according to claim 1, wherein when the medical/cam information of the designated patient or cam-needing person of each of the groups is displayed on the user terminals, the part of the medical/care information is displayed in a first region which all the group members of the group can view and the remainder of the medical/care information is displayed in a second region which only the medical workers and/or care workers as the group members of the group can view; and the first region and the second region are displayed on the same user terminal simultaneously or alternatively.

8. The medical/care support method according to claim 1, wherein when the medical/care information of the n groups having the same service recipient identification information and the different disease identification information is displayed on the user terminals of the group members of the n groups, the medical/care information of the n groups is displayed integratively on the same user terminal.

9. A medical/care support system for supporting provision of medical/care service by making medical/care information about specific patients or care-needing persons viewable on user terminals by way of a network in response to requests from the user terminals; which comprises:

(a) a user management section; comprising:

a user identification information storing subsection that is configured to assign user identification information to respective users utilizing the medical/care service by way of the user terminals to store the user identification information;

a service recipient identification information storing subsection that is configured to assign service recipient identification information to respective patients or care-needing persons as the users to store the service recipient identification information so as to be associated with the user identification information of the patients or care-needing persons;

a service worker identification information storing subsection that is configured to assign service worker identification information to respective medical workers or care workers as the users to store the service worker identification information so as to be associated with the user identification information of the medical workers or care workers; and a service-related facility identification information storing subsection that is configured to assign service-related facility identification information to respective service-related facilities to which the medical workers or care workers belong to store the service-related facility identification information so as to be associated with the service worker identification information of the medical workers or care workers; and (b) a group management section that is configured to generate groups, each of which has unique group identification information, to store the group identification information so as to be associated with the service recipient identification information of the patients or care-needing persons; and an invitation request management section that is configured to add, in response to sending of an invitation request which includes designation of an inviting person and an invited person who is designated from the users and which is performed using one of the user terminals, the invited person to a designated one of the groups as its group member, under a condition that the invitation request is approved by the invited person using one of the user terminals and that permission is obtained by at least one of a predetermined medical worker/care worker-side administrator and a predetermined patient/care-needing person-side administrator using one of the user terminals;

wherein each of the groups is associated with a designated one of the patients or care-needing persons and a designated one of one or more diseases of the designated patient or care-needing person by associating the group identification information of the said group with the service recipient identification information of the designated patient or care-needing person and with the disease identification information of the designated disease of the designated patient or care-needing person;

wherein when each of the groups includes the medical workers and/or care workers as its group members, the medical/care information of the designated patient or care-needing person about the designated disease thereof that corresponds to the said group is viewable to the medical workers and/or care workers as the group members of the said group on their user terminals by way of the network for sharing the said medical/care information, in which the medical/care information shared among the medical workers and/or care workers as the group members of the said group is displayed on their user terminals as a timeline which is generated for the said group, and the group members of the said group can contribute and view messages in the timeline;

wherein when the medical/care information shared among the medical workers and/or care workers as the group members of each of the groups is displayed on their user terminals, a part of the shared medical/care information is displayed in such a way that all the group members of the said group can view and a remainder of the shared medical/care information is displayed in such a way that only the medical workers and/or care workers as the group members of the said group can view;

wherein a number of the groups having the same service recipient identification information, which have different disease identification information, is n (n is an integer equal to 2 or greater), and the group identification information of each of the n groups is associated with the service-related facility identification information of one or more of the service-related facilities to which the medical workers and/or care workers as the group members of a corresponding one of the n groups belong; and wherein the medical/care information of the n groups having the same service recipient identification information, which is distributed among the service-related facilities to which the medical workers and/or care workers as the group members of the n groups belong, is sharable among the group members of the n groups while protecting privacy of the patient or care-needing person corresponding to the said n groups, and is viewable in a combined form to the group members of the said n groups by way of the user terminals of the group members of the n groups using different sharing rules to enable the medical workers and/or care workers as the group members of the said n groups to the medical/care information of the said n groups, which provides improved medical/care service to the patient or care-needing person corresponding to the said n groups.

10. The medical/care support system according to claim 9, wherein when a personalization registration request which has been sent by way of one of the user terminals is received, the service recipient identification information designated by the personalization registration request and the service-related facility identification information designated by the personalization registration request are stored so as to be associated with each other; and personalized facility information for the patient or care-needing person corresponding to the designated service recipient identification information is generated by associating the designated service recipient identification information and the designated service-related facility identification information with each other.

11. The medical/care support system according to claim 10, wherein whether or not the personalization registration request is approved is inquired to the patient or care-needing person corresponding to the service recipient identification information designated by the personalization registration request while encouraging selection of a sharing rule for the medical/care information of the patient or care-needing person; and when the personalization registration request is approved by the patient or care-needing person, the sharing rule selected is stored.

12. The medical/care support system according to claim 10, wherein identity verification for approving the personalization registration request by the patient or care-needing person corresponding to the service recipient identification information designated by the personalization registration request is performed using a passcode which is generated based on a service recipient number or an insured person number used in the service-related facility corresponding to the service-related facility identification information designated by the personalization registration request.

13. The medical/care support system according to claim 9, wherein identity verification of the user designated in the invitation request as the invited person is performed using a telephone number or a passphrase of the user designated in the invitation request as the invited person.

14. The medical/care support system according to claim 10, wherein when the patient or care-needing person corresponding to the service recipient identification information designated by the personalization registration request approves the personalization registration request, a short-distance wireless communication terminal in which a terminal number and Uniform Resource Locator (URL) information assigned to the service-related facility corresponding to the service-related facility identification information designated by the personalization registration request have been stored is used; and the URL information is transmitted to the user terminal for the patient or care-needing person corresponding to the designated service recipient identification information by contacting the short-distance wireless communication terminal with the user terminal, thereby displaying a personalization registration approval screen on the user terminal.

15. The medical/care support system according to claim 9, wherein when the medical/care information of the designated patient or care-needing person of each of the groups is displayed on the user terminals, the part of the medical/care information is displayed in a first region which all the group members of the group can view and the remainder of the medical/care information is displayed in a second region which only the medical workers and/or care workers as the group members of the group can view; and the first region and the second region are displayed on the same user terminal simultaneously or alternatively.

16. The medical/care support system according to claim 9, wherein when the medical/care information of the n groups having the same service recipient identification information and the different disease identification information is displayed on the user terminals of the group members of the n groups, the medical/care information of the n groups is displayed integratively on the same user terminal.

17. A non-transitory computer readable medium storing a medical/care support program for supporting provision of medical/care service by making medical/care information about specific patients or care-needing persons viewable on user terminals by way of a network in response to requests from the user terminals using a medical/care support system, wherein the medical/care support system comprises a user management section and a group management section; which comprises processes to be executed by a computer, the processes comprises:

assigning user identification information to respective users utilizing the medical/care service by way of the user terminals to store the user identification information using the user management section;

assigning service recipient identification information to respective patients or care-needing persons as the users to store the service recipient identification information so as to be associated with the user identification information of the patients or care-needing persons using the user management section;

assigning service worker identification information to respective medical workers or care workers as the users to store the service worker identification information so as to be associated with the user identification information of the medical workers or care workers using the user management section;

assigning service-related facility identification information to respective service-related facilities to which the medical workers or care workers belong to store the service-related facility identification information so as to be associated with the service worker identification information of the medical workers or care workers using the user management section;

generating groups, each of which has unique group identification information, to store the group identification information so as to be associated with the service recipient identification information of the patients or care-needing persons using the group management section; and adding, in response to sending of an invitation request which includes designation of an inviting person and an invited person who is designated from the users and which is performed using one of the user terminals, the invited person to a designated one of the groups as its group member, under a condition that the invitation request is approved by the invited person using one of the user terminals and that permission is obtained by at least one of a predetermined medical worker/care worker-side administrator and a predetermined patient/care-needing person-side administrator using one of the user terminals;

wherein each of the groups is associated with a designated one of the patients or care-needing persons and a designated one of one or more diseases of the designated patient or care-needing person by associating the group identification information of the said group with the service recipient identification information of the designated patient or care-needing person and with the disease identification information of the designated disease of the designated patient or care-needing person;

wherein when each of the groups includes the medical workers and/or care workers as its group members, the medical/care information of the designated patient or care-needing person about the designated disease thereof that corresponds to the said group is viewable to the medical workers and/or care workers as the group members of the said group on their user terminals by way of the network for sharing the said medical/care information, in which the medical/care information shared among the medical workers and/or care workers as the group members of the said group is displayed on their user terminals as a timeline which is generated for the said group, and the group members of the said group can contribute and view messages in the timeline;

wherein when the medical/care information shared among the medical workers and/or care workers as the group members of each of the groups is displayed on their user terminals, a part of the shared medical/care information is displayed in such a way that all the group members of the said group can view and a remainder of the shared medical/care information is displayed in such a way that only the medical workers and/or care workers as the group members of the said group can view;

wherein a number of the groups having the same service recipient identification information, which have different disease identification information, is n (n is an integer equal to 2 or greater), and the group identification information of each of the n groups is associated with the service-related facility identification information of one or more of the service-related facilities to which the medical workers and/or care workers as the group members of a corresponding one of the n groups belong; and wherein the medical/care information of the n groups having the same service recipient identification information, which is distributed among the service-related facilities to which the medical workers and/or care workers as the group members of the n groups belong, is sharable among the group members of the n groups while protecting privacy of the patient or care-needing person corresponding to the said n groups, and is viewable in a combined form to the group members of the said n groups by way of the user terminals of the group members of the n groups using different sharing rules to enable the medical workers and/or care workers as the group members of the said n groups to use the medical/care information of the said n groups, which provides improved medical/care service to the patient or care-needing person corresponding to the said n groups.

18. The non-transitory computer readable medium according to claim 17, wherein when a personalization registration request which has been sent by way of one of the user terminals is received, the service recipient identification information designated by the personalization registration request and the service-related facility identification information designated by the personalization registration request are stored so as to be associated with each other; and personalized facility information for the patient or care-needing person corresponding to the designated service recipient identification information is generated by associating the designated service recipient identification information and the designated service-related facility identification information with each other.

19. The non-transitory computer readable medium according to claim 18, wherein whether or not the personalization registration request is approved is inquired to the patient or care-needing person corresponding to the service recipient identification information designated by the personalization registration request while encouraging selection of a sharing rule for the medical/care information of the patient or care-needing person; and when the personalization registration request is approved by the patient or care-needing person, the sharing rule selected is stored.

20. The non-transitory computer readable medium according to claim 18, wherein identity verification for approving the personalization registration request by the patient or care-needing person corresponding to the service recipient identification information designated by the personalization registration request is performed using a passcode which is generated based on a service recipient number or an insured person number used in the service-related facility corresponding to the service-related facility identification information designated by the personalization registration request.

21. The non-transitory computer readable medium according to claim 17, wherein identity verification of the user designated in the invitation request as the invited person is performed using a telephone number or a passphrase of the user designated in the invitation request as the invited person.

22. The non-transitory computer readable medium according to claim 18, wherein when the patient or care-needing person corresponding to the service recipient identification information designated by the personalization registration request approves the personalization registration request, a short-distance wireless communication terminal in which a terminal number and Uniform Resource Locator (URL) information assigned to the service-related facility corresponding to the service-related facility identification information designated by the personalization registration request have been stored is used; and the URL information is transmitted to the user terminal for the patient or care-needing person corresponding to the designated service recipient identification information by contacting the short-distance wireless communication terminal with the user terminal, thereby displaying a personalization registration approval screen on the user terminal.

23. The non-transitory computer readable medium according to claim 17, wherein when the medical/care information of the designated patient or care-needing person of each of the groups is displayed on the user terminals, the part of the medical/care information is displayed in a first region which all the group members of the group can view and the remainder of the medical/care information is displayed in a second region which only the medical workers and/or care workers as the group members of the group can view; and the first region and the second region are displayed on the same user terminal simultaneously or alternatively.

24. The non-transitory computer readable medium according to claim 17, wherein when the medical/care information of the n groups having the same service recipient identification information and the different disease identification information is displayed on the user terminals of the group members of the n groups, the medical/care information of the n groups is displayed integratively on the same user terminal.

* * * * *